(12) United States Patent
Cink et al.

(10) Patent No.: US 9,809,576 B1
(45) Date of Patent: Nov. 7, 2017

(54) SYNTHETIC ROUTE TO ANTI-VIRAL AGENTS

(71) Applicant: AbbVie Inc., North Chicago, IL (US)

(72) Inventors: Russell D. Cink, Grayslake, IL (US); Kirill A. Lukin, Vernon Hills, IL (US); Marvin R. Leanna, Grayslake, IL (US); Matthew J. Pelc, Pleasant Prairie, WI (US); Timothy B. Towne, Lindenhurst, IL (US); Dennie S. Welch, Gurnee, IL (US); Kenneth M. Engstrom, Mundelein, IL (US); Matthew M. Ravn, Round Lake Beach, IL (US); Richard D. Bishop, Third Lake, IL (US); Gang Zhao, Northbrook, IL (US); Jianzhang Mei, Lake Forest, IL (US); Jeff M. Kallemeyn, Libertyville, IL (US); David R. Hill, Gurnee, IL (US); Michael J. Abrahamson, Chicago, IL (US); Westin H. Morrill, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/802,372

(22) Filed: Jul. 17, 2015

Related U.S. Application Data

(60) Provisional application No. 62/026,412, filed on Jul. 18, 2014.

(51) Int. Cl.
C07D 403/12 (2006.01)
C07C 69/74 (2006.01)
C07D 241/44 (2006.01)
C07D 405/06 (2006.01)
C07C 271/34 (2006.01)
C07C 67/08 (2006.01)
C07D 405/14 (2006.01)
C07D 487/04 (2006.01)
C07C 269/06 (2006.01)
C07C 269/04 (2006.01)
C07C 41/26 (2006.01)
C07C 43/196 (2006.01)

(52) U.S. Cl.
CPC ............ C07D 403/12 (2013.01); C07C 41/26 (2013.01); C07C 43/196 (2013.01); C07C 67/08 (2013.01); C07C 69/74 (2013.01); C07C 269/04 (2013.01); C07C 269/06 (2013.01); C07C 271/34 (2013.01); C07D 241/44 (2013.01); C07D 405/06 (2013.01); C07D 405/14 (2013.01); C07D 487/04 (2013.01)

(58) Field of Classification Search
CPC .. C07D 403/12; C07D 241/44; C07D 405/06; C07D 405/14; C07D 487/04; C07C 69/74; C07C 271/34; C07C 67/08; C07C 269/06; C07C 269/04; C07C 41/26; C07C 43/196
See application file for complete search history.

(56) References Cited

U.S. PATENT DOCUMENTS

2012/0070416 A1* 3/2012 Or ..................... C07K 5/06034
424/85.6
2015/0175626 A1 6/2015 Cagulada et al.

FOREIGN PATENT DOCUMENTS

WO WO-2012/040167 A1 3/2012

OTHER PUBLICATIONS

U.S. Appl. No. 14/802,392, Lukin et al.
U.S. Appl. No. 15/010,557, Abrahamson et al.

* cited by examiner

Primary Examiner — Matt Mauro
(74) Attorney, Agent, or Firm — Foley Hoag LLP

(57) ABSTRACT

The invention provides methods of synthesizing a viral protease inhibitor in high yield, without using expensive catalysts or challenging reaction conditions.

2 Claims, No Drawings

SYNTHETIC ROUTE TO ANTI-VIRAL AGENTS

RELATED APPLICATIONS

This application claims the benefit of priority to U.S. Provisional Patent Application Ser. No. 62/026,412, filed Jul. 18, 2014, the contents of which are hereby incorporated by reference.

BACKGROUND

Complex biologically active molecules are challenging, expensive, and time-consuming to synthesize. Synthesizing chiral, non-racemic compounds with good enantio- and diastereoselectivity is even more challenging. An example of such a molecule is Compound 1:

Compound 1

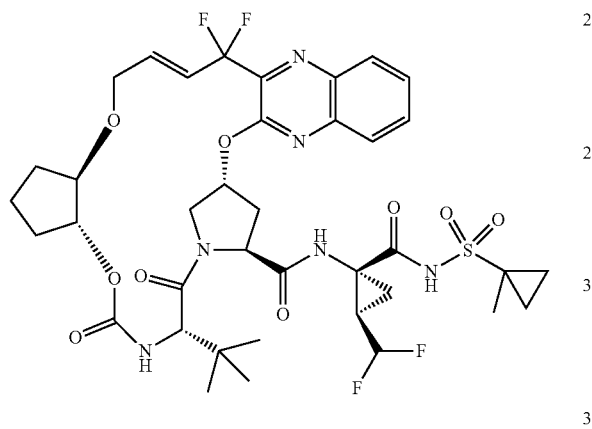

This compound is a potent inhibitor of the hepatitis C virus (HCV) NS3/4A protease; it shows broad genotype activity and substantially improved in vitro profile compared to earlier generation HCV NS3/4A protease inhibitors.

The original synthesis of this compound requires a ring closing metathesis (RCM) reaction for synthesis of the macrocycle (see WO 2012/040167). However, this RCM reaction involves high catalyst loading and expensive starting materials, resulting in low throughput due to dilute reaction conditions and increased costs.

There exists a need for new, efficient synthetic methods to construct Compound 1.

SUMMARY OF THE INVENTION

In certain embodiments, the invention relates to a compound selected from:

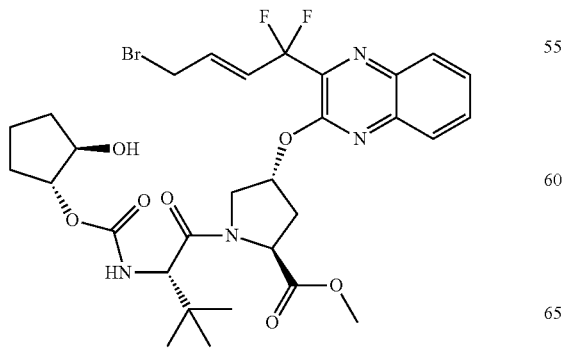

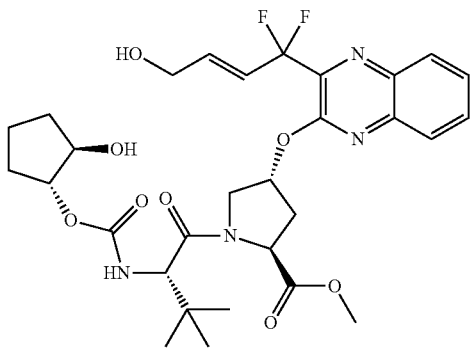

or a salt thereof.

In certain embodiments, the invention relates to a compound selected from:

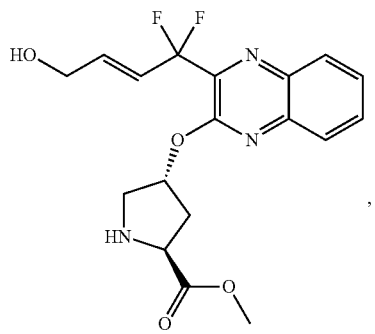

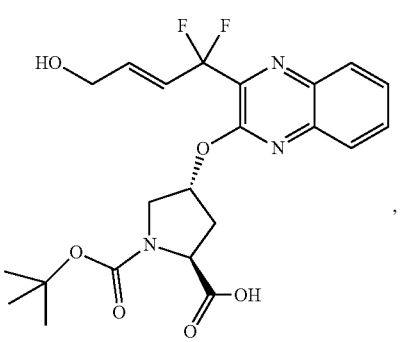

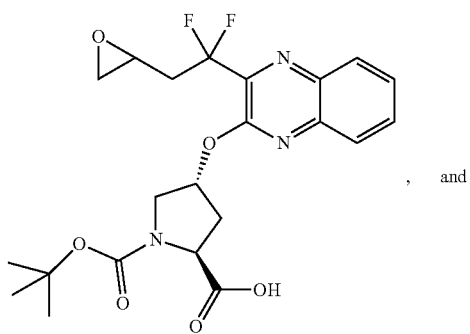

, and

-continued

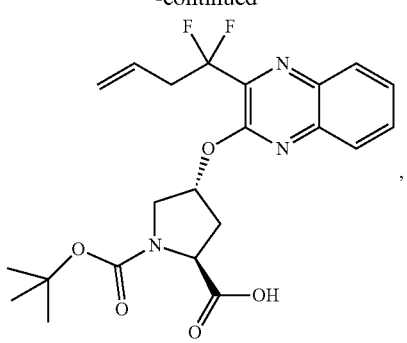

or a salt thereof.

In certain embodiments, the invention relates to a compound selected from:

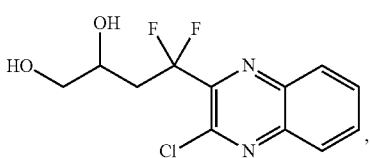

or a salt thereof.

In certain embodiments, the invention relates to a compound selected from:

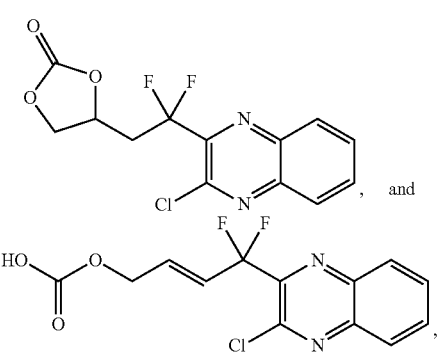

or a salt thereof.

In certain embodiments, the invention relates to a compound selected from:

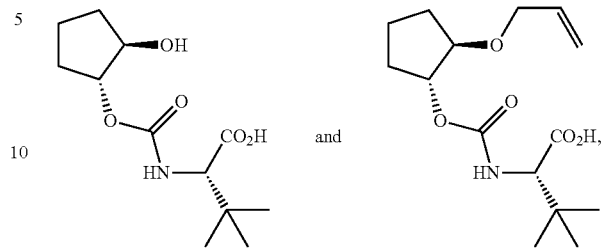

or a salt thereof.

In certain embodiments, the invention relates to a compound selected from:

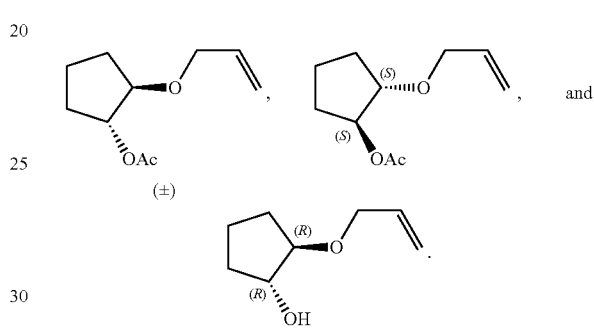

In certain embodiments, the invention relates to a method according to reaction scheme A:

Scheme A

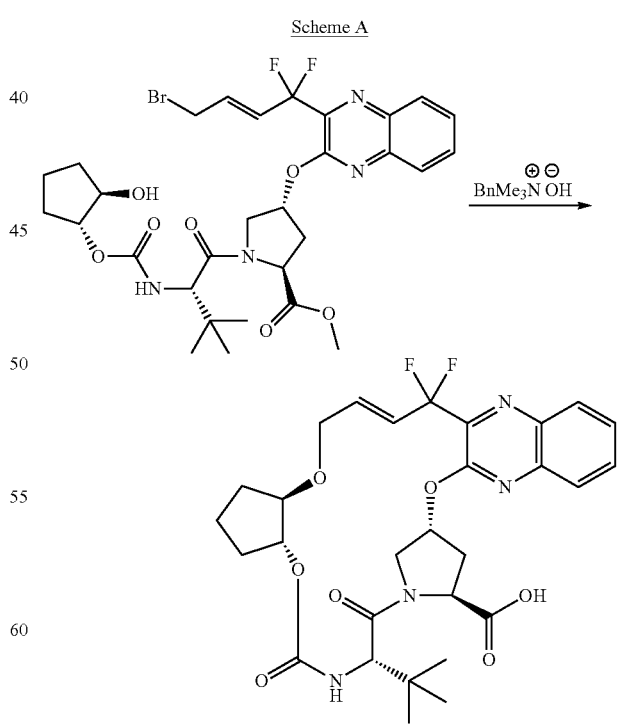

wherein the reaction takes place in a sixteenth solvent, thereby forming a thirteenth product mixture comprising

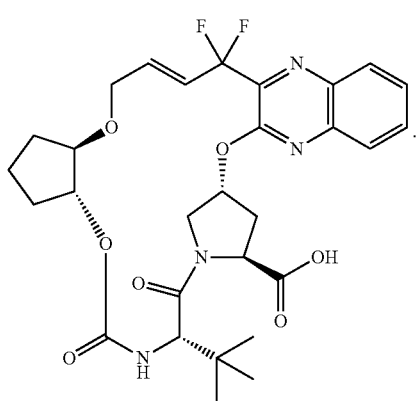 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)O)N(C2)C1=O]

In certain embodiments, the invention relates to a method according to reaction scheme B:

Scheme B

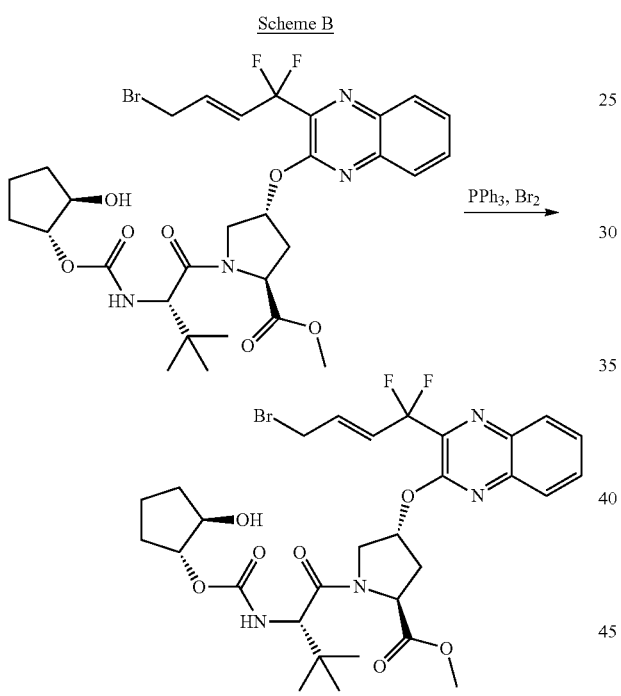

wherein the reaction takes place in a fifteenth solvent, thereby forming a twelfth product mixture comprising In certain embodiments, the invention relates to a method according to reaction scheme C:

Scheme C

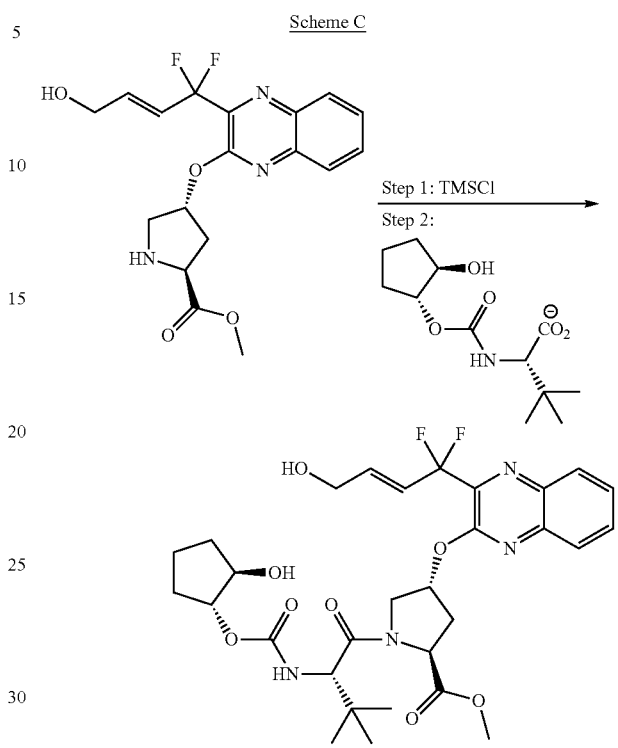

wherein Step 1 of the reaction takes place in a thirteenth solvent in the presence of a seventh base; and Step 2 of the reaction takes place in a fourteenth solvent, thereby forming an eleventh product mixture comprising

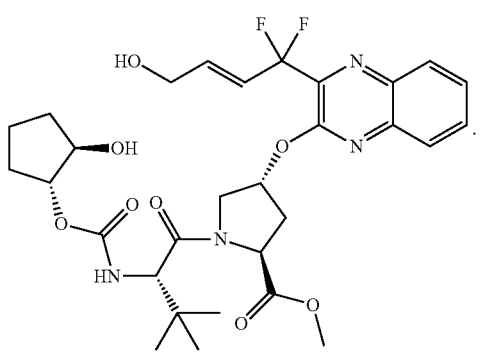 [SMILES: COC(=O)[C@@H]1C[C@@H](Oc2nc3ccccc3nc2C(F)(F)/C=C/CO)CN1C(=O)[C@@H](NC(=O)O[C@@H]1CCC[C@H]1O)C(C)(C)C]

In certain embodiments, the invention relates to a method according to reaction scheme D:

Scheme D

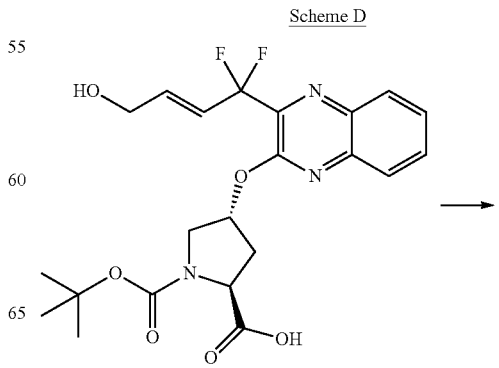

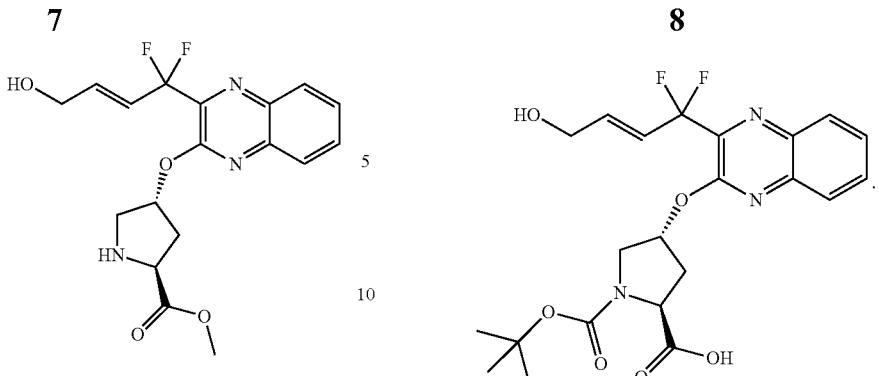

wherein the reaction takes place in a twelfth solvent in the presence of a second acid, thereby forming a tenth product mixture comprising

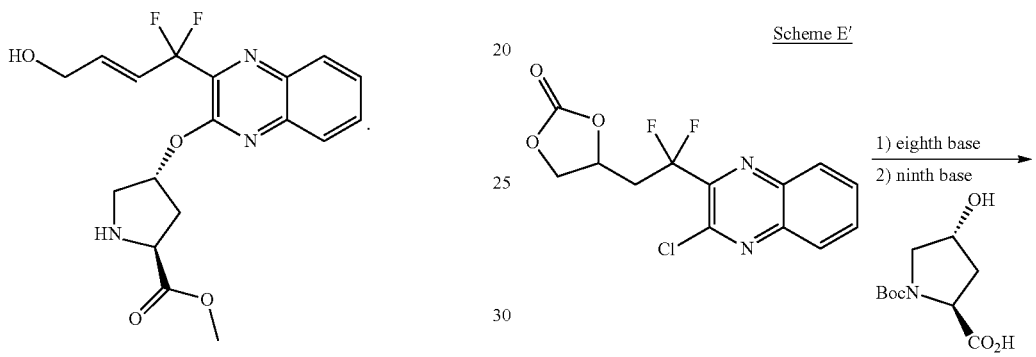

In certain embodiments, the invention relates to a method according to reaction scheme E:

Scheme E

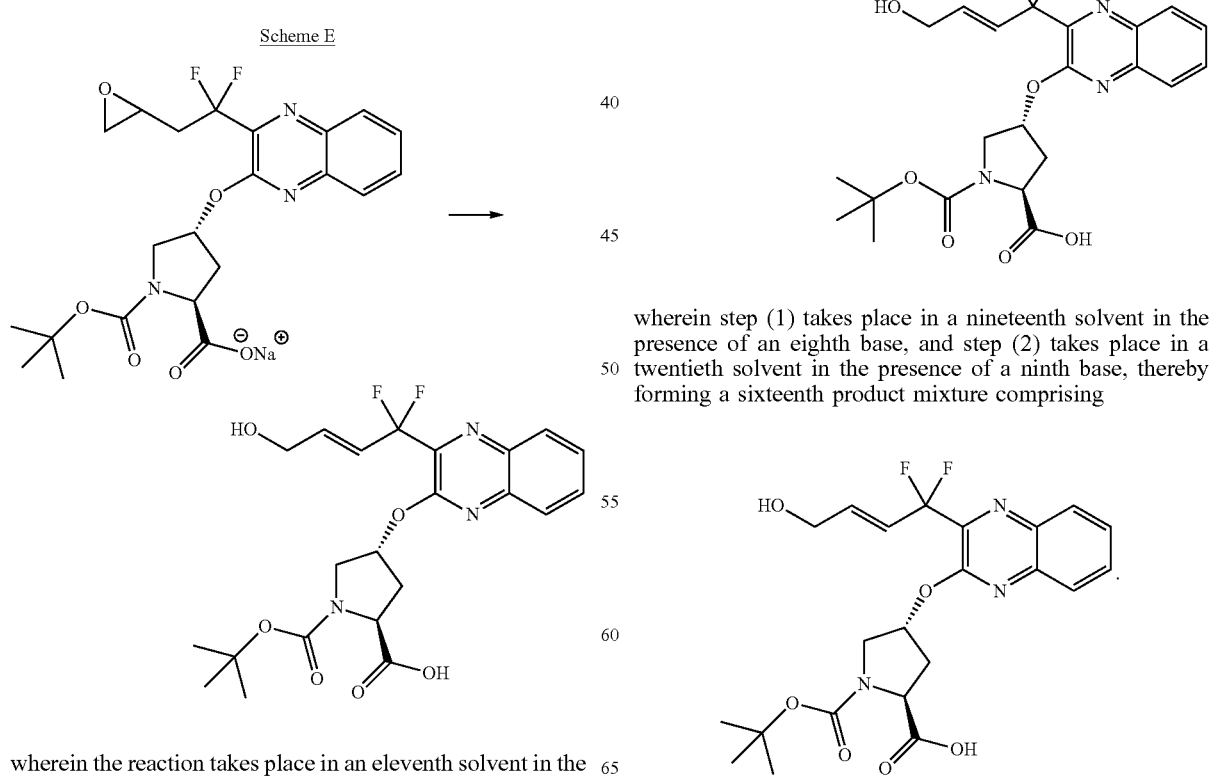

wherein the reaction takes place in an eleventh solvent in the presence of a sixth base, thereby forming a ninth product mixture comprising In certain embodiments, the invention relates to a method according to reaction scheme E':

Scheme E' wherein step (1) takes place in a nineteenth solvent in the presence of an eighth base, and step (2) takes place in a twentieth solvent in the presence of a ninth base, thereby forming a sixteenth product mixture comprising In certain embodiments, the invention relates to a method according to reaction scheme F:

Scheme F

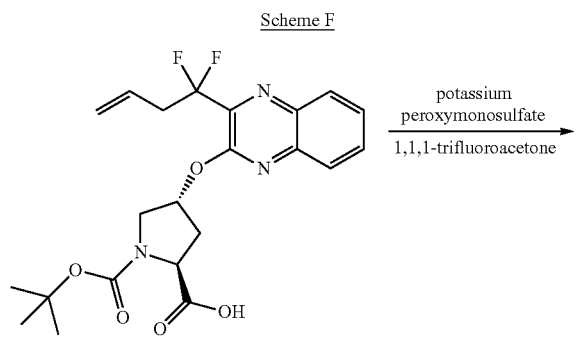
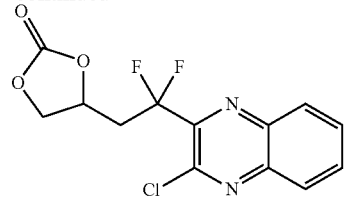

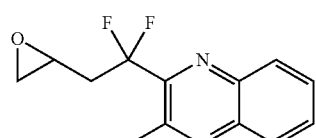

wherein the reaction takes place in a tenth solvent in the presence of a fifth base, thereby forming an eighth product mixture comprising

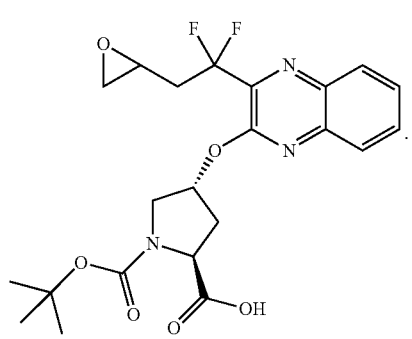 [SMILES: CC(C)(C)OC(=O)N1C[C@H](Oc2nc3ccccc3nc2C(F)(F)CC2CO2)C[C@H]1C(=O)O]

In certain embodiments, the invention relates to a method according to reaction scheme F':

Scheme F'

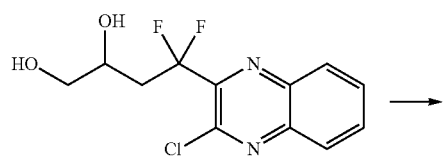

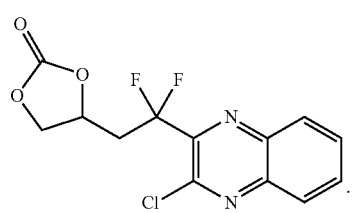 [SMILES: O=C1OCC(CC(F)(F)c2nc3ccccc3nc2Cl)O1]

wherein the reaction takes place in a eighteenth solvent in the presence of a reagent, thereby forming an fifteenth product mixture comprising

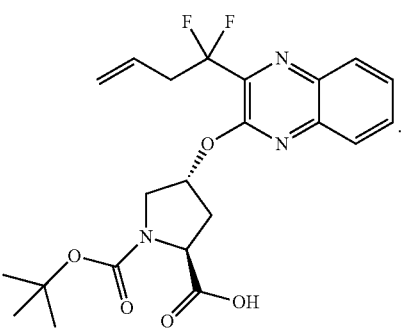 [SMILES: C=CCC(F)(F)c1nc2ccccc2nc1O[C@@H]1C[C@@H](C(=O)O)N(C(=O)OC(C)(C)C)C1]

In certain embodiments, the invention relates to a method according to reaction scheme G:

Scheme G

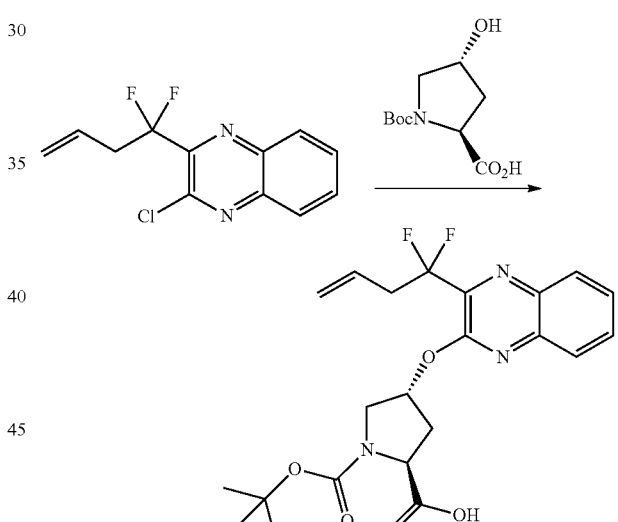

wherein the reaction takes place in a ninth solvent in the presence of a fourth base, thereby forming a seventh product mixture comprising In certain embodiments, the invention relates to a method according to reaction scheme G':

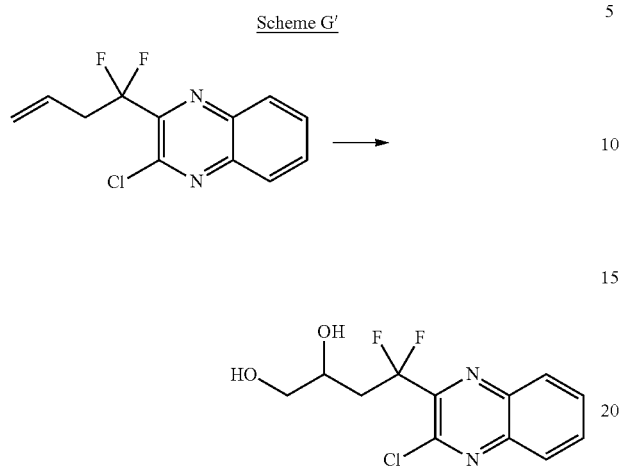

wherein the reaction takes place in a seventeenth solvent in the presence of an oxidant, thereby forming a fourteenth product mixture comprising

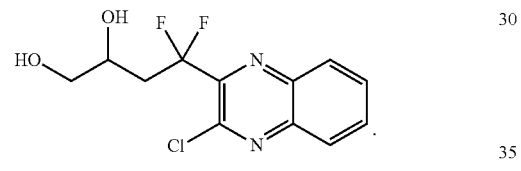

In certain embodiments, the invention relates to a method according to reaction scheme H:

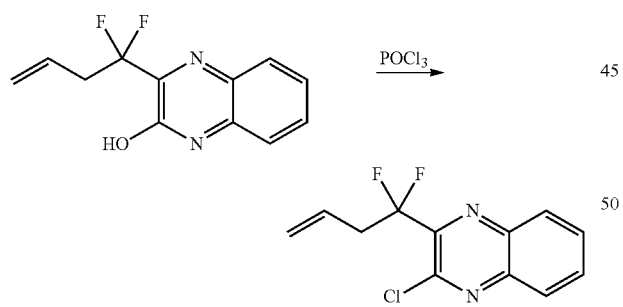

wherein the reaction takes place in an eighth solvent, thereby forming a sixth product mixture comprising

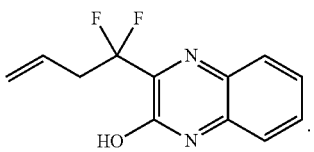 [SMILES: C=CCC(F)(F)c1nc2ccccc2nc1O]

In certain embodiments, the invention relates to a method according to reaction scheme I:

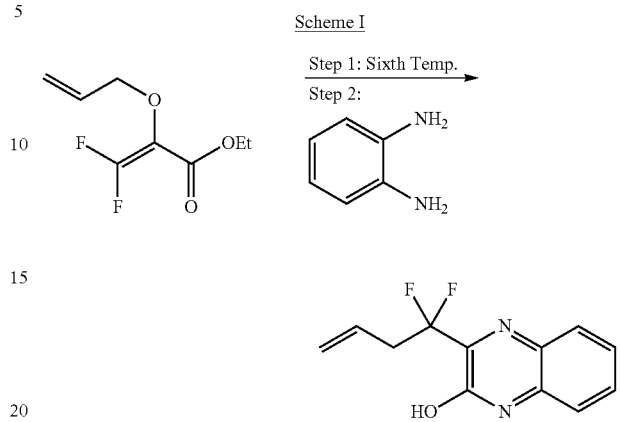

wherein Step 1 of the reaction takes place in a sixth solvent at a sixth temperature to effect a Claisen rearrangement, and Step 2 of the reaction takes place in a seventh solvent at a seventh temperature, thereby forming a fifth product mixture comprising In certain embodiments, the invention relates to a method according to reaction scheme J:

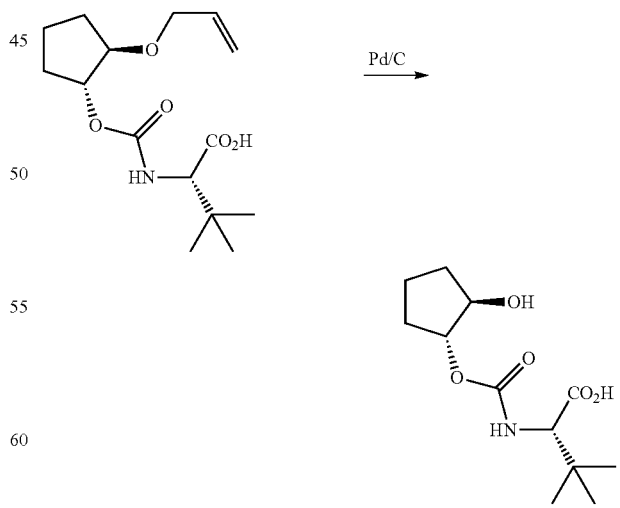

wherein the reaction takes place in a fifth solvent in the presence of a first acid and a hydrogen source, thereby forming a fourth product mixture comprising

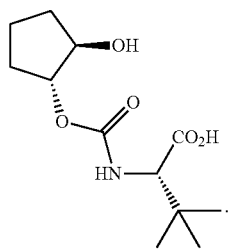 [SMILES: CC(C)(C)[C@H](NC(=O)O[C@@H]1CCC[C@H]1O)C(=O)O]

In certain embodiments, the invention relates to a method according to reaction scheme K:

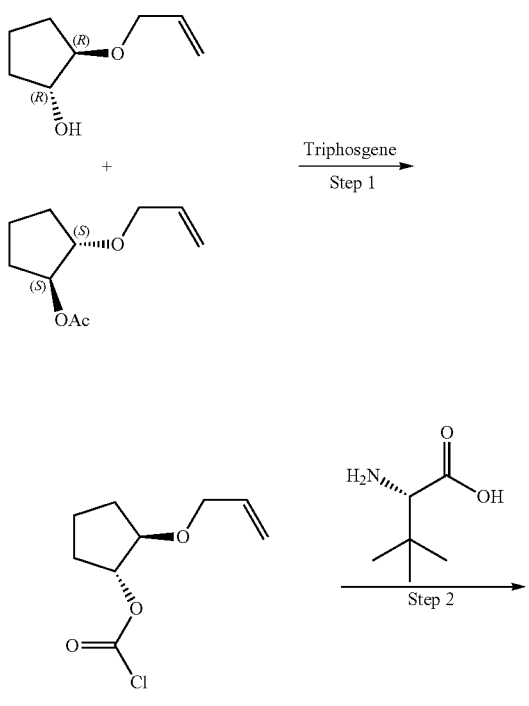

wherein Step 1 of the reaction takes place in a third solvent in the presence of a second base; and Step 2 of the reaction takes place in a fourth solvent in the presence of a third base, thereby forming a third product mixture comprising

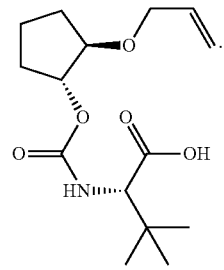 [SMILES: C=CCO[C@@H]1CCC[C@H]1OC(=O)N[C@H](C(=O)O)C(C)(C)C]

In certain embodiments, the invention relates to a method according to reaction scheme L:

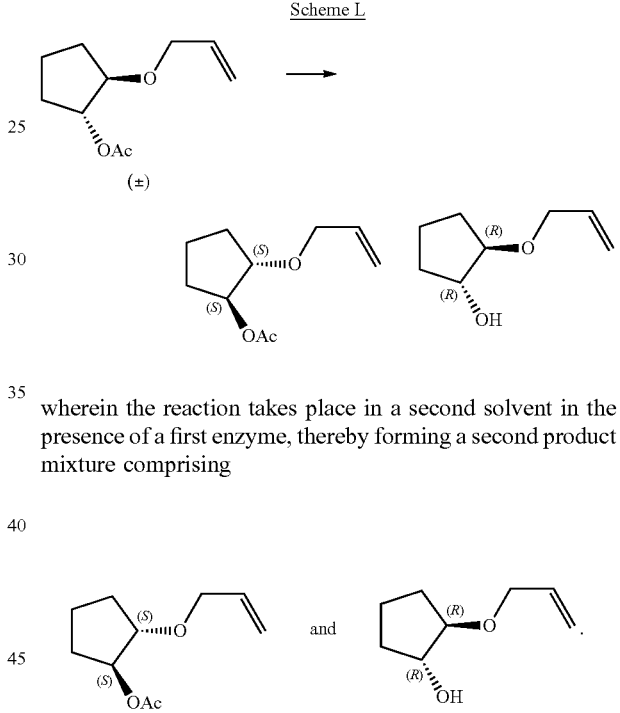

wherein the reaction takes place in a second solvent in the presence of a first enzyme, thereby forming a second product mixture comprising In certain embodiments, the invention relates to a method according to reaction scheme M:

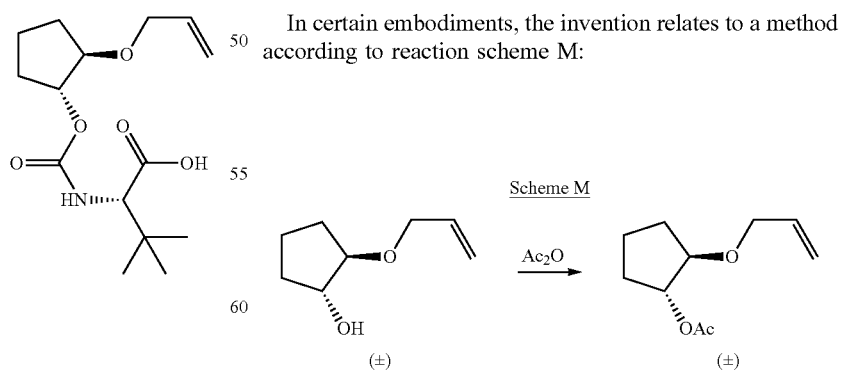

wherein the reaction takes place in a first solvent in the presence of a first base, thereby forming a first product mixture comprising

15

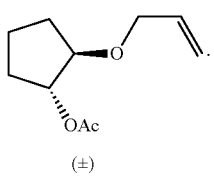

(±)

DETAILED DESCRIPTION OF THE INVENTION

I. Overview

In certain embodiments, the invention involves a method of synthesizing the macrocycle of Compound 1 based on an intramolecular etherification reaction to form compound 3 (see Scheme 1). In certain embodiments, the synthesis of 1 via compound 3 eliminates the need for expensive catalysts required in ring-closing metathesis reactions. In certain embodiments, the synthesis of 1 via compound 3 uses low-cost starting materials. In certain embodiments, the synthesis of 1 via compound 3 results in an overall high throughput.

In certain embodiments, the etherification route for the synthesis of 1, shown in Scheme 1, utilizes an intramolecular etherification reaction as the key step in the synthesis of the macrocycle 3. The synthesis of 1 may begin with the peptide coupling of amine 69 with carboxylic acid 70 wherein protection of the allylic alcohol in 69 may be accomplished in-situ with the trimethylsilyl (TMS) (or triethysilyl (TES), or similar) protecting group. The allylic alcohol of coupling product 71 may be activated by conversion to the allylic bromide 72, although alternate leaving groups can also be employed (for example, Cl, I, TsO, TfO, MsO, etc. instead of Br). The allylic bromide 72 may undergo intramolecular etherification and saponification to form the macrocycle acid 3. The coupling partner for the macrocycle may be the amine 4, which may be synthesized by coupling acid 54 with sulfonamide 55 to yield 56 which may be subjected to tert-butyloxycarbonyl (Boc) deprotection. The macrocycle acid 3 may be then coupled to amine 4 to yield 1. In certain embodiments, the synthesis of 1 is based on the construction of three key structural fragments of the molecule, in particular compounds 54, 69, and 70.

Scheme 1. Etherification Route for the Synthesis of 1

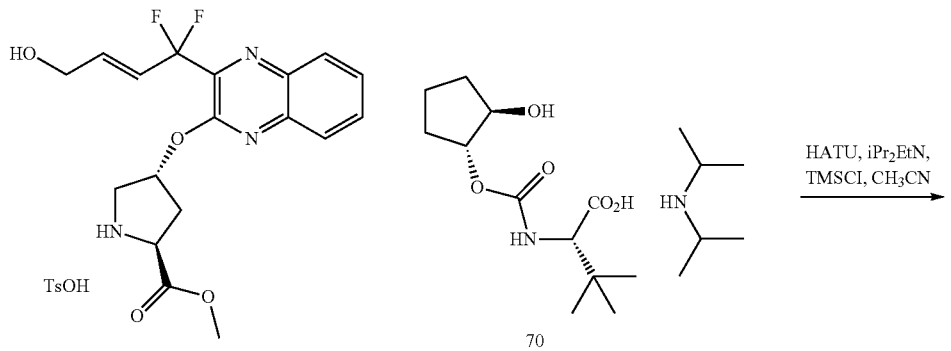

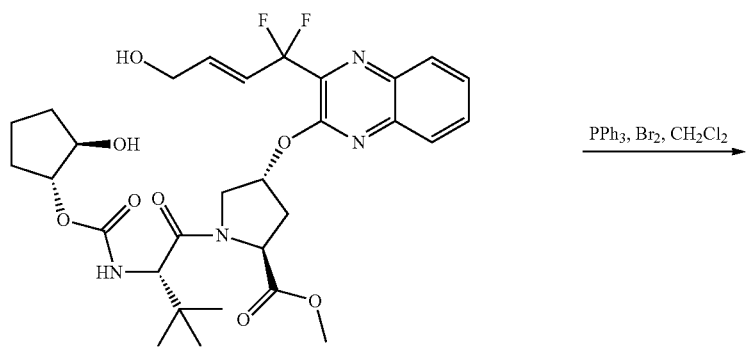

-continued
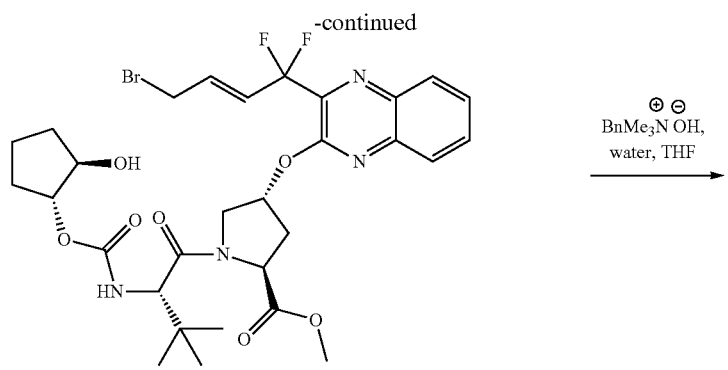
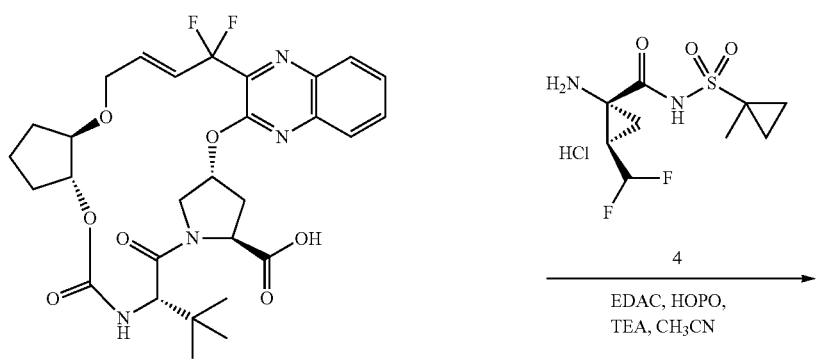
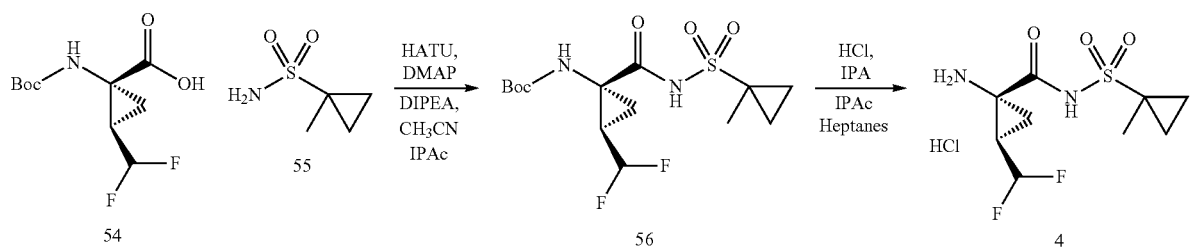
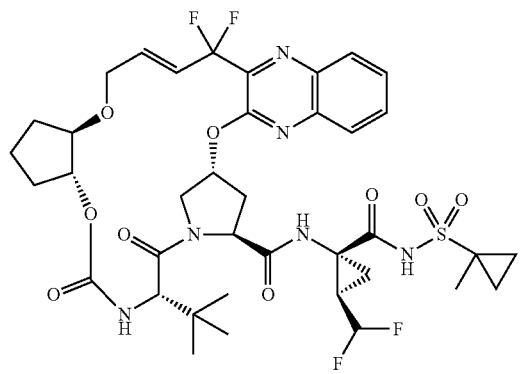

In certain embodiments, the invention relates to a method of synthesizing compound 23 (see Scheme 4).

II. Definitions

Listed below are definitions of various terms used to describe this invention. These definitions apply to the terms as they are used throughout this specification and claims, unless otherwise limited in specific instances, either individually or as part of a larger group. The number of carbon atoms in a hydrocarbyl substituent can be indicated by the prefix "$C_x$-$C_y$," where x is the minimum and y is the maximum number of carbon atoms in the substituent.

The term "alkyl" as used herein, refers to a saturated, straight- or branched-chain hydrocarbon radical typically containing from 1 to 20 carbon atoms. For example, "$C_1$-$C_6$ alkyl" or "$C_1$-$C_8$ alkyl" contains from one to six, or from one to eight, carbon atoms, respectively. Examples of alkyl radicals include, but are not limited to, methyl, ethyl, propyl, isopropyl, n-butyl, tert-butyl, neopentyl, n-hexyl, heptyl, octyl radicals and the like.

The term "cycloalkyl" denotes a monovalent group derived from a monocyclic or polycyclic saturated carbocyclic ring compound. Examples of cycloalkyl include, but are not limited to, cyclopropyl, cyclobutyl, cyclopentyl, cyclohexyl, bicyclo[2.2.1]heptyl, and bicyclo[2.2.2]octyl and the like.

The term "amino-protecting group," as used herein, refers to a labile chemical moiety that can protect an amino group against undesired reactions during synthetic procedures. After said synthetic procedure(s) the amino-protecting group as described herein may be selectively removed. Suitable amino-protecting groups are described generally in T. H. Greene and P. G. M. Wuts, Protective Groups in Organic Synthesis, 3rd edition, John Wiley & Sons, New York (1999). Examples of amino-protecting groups include, but are not limited to, t-butoxycarbonyl, 9-fluorenyl-methoxycarbonyl, benzyloxycarbonyl, and the like.

The term "protected amino," as used herein, refers to an amino group protected with an amino-protecting group as defined above.

As used herein, the term "salt" preferably refers to "pharmaceutically acceptable salts," which are, within the scope of sound medical judgment, suitable for use in contact with the tissues of humans and other vertebrates, preferably mammals, without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977). Such salts can be prepared in situ during isolation and purification of reaction products as described herein, or separately, such as by reacting a free base function with a suitable acid, such as an organic acid. Examples of pharmaceutically acceptable salts include, but are not limited to, hydrochloride, hydrobromide, phosphate, sulfate, perchlorate, acetate, maleate, tartrate, citrate, succinate, or malonate. Other pharmaceutically acceptable salts include, but are not limited to, adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, sulfate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, ammonium, quaternary ammonium, and amine cations associated with counterions such as halide, hydroxide, carboxylate, sulfate, phosphate, nitrate, $C_{1-6}$ alkyl sulfonate and aryl sulfonate.

As used herein, the term "enantioenriched" means a mixture of enantiomers in which one of the two enantiomers is present in a larger amount. This term also encompasses an enantiomerically pure compounds (i.e., a compound having an enantiomeric excess (ee) greater than about 90%, greater than about 95%, preferably greater than about 98%, most preferably greater than about 99%).

Various aspects of the invention are described in further detail herein.

III. Exemplary Compounds

In certain embodiments, the invention relates to a compound selected from:

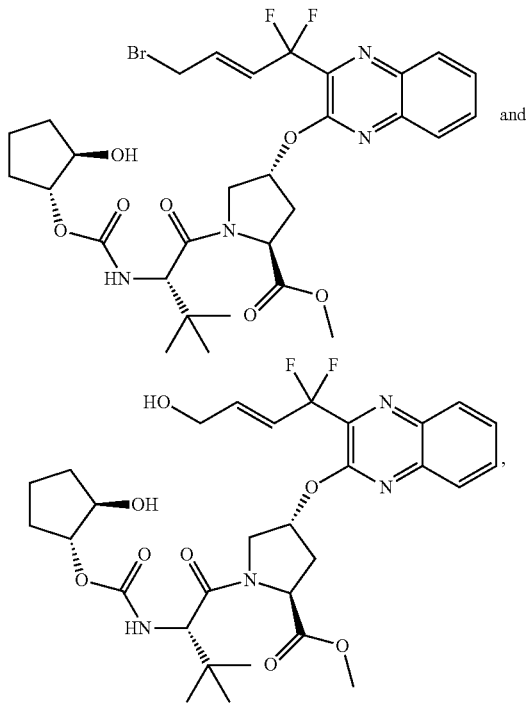

and or a salt thereof.

In certain embodiments, the invention relates to any one of the compounds described herein, wherein the compound is

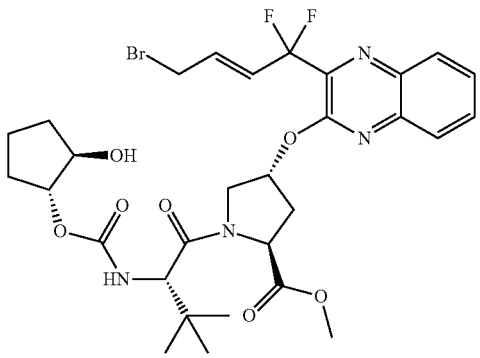 [SMILES: COC(=O)[C@@H]1C[C@@H](Oc2nc3ccccc3nc2C(F)(F)/C=C/CBr)CN1C(=O)[C@@H](NC(=O)O[C@@H]1CCC[C@H]1O)C(C)(C)C]

or a salt thereof.

In certain embodiments, the invention relates to any one of the compounds described herein, wherein the compound is

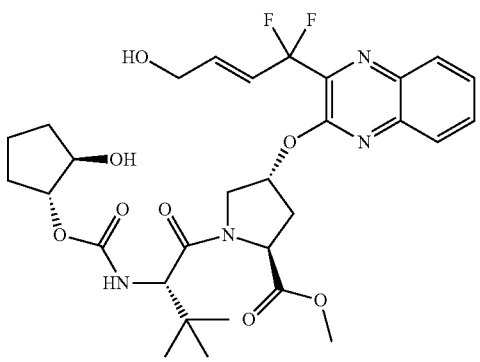

or a salt thereof.

In certain embodiments, the invention relates to a compound selected from:

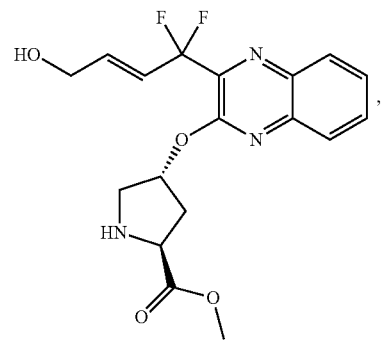 [SMILES: COC(=O)[C@@H]1C[C@@H](Oc2nc3ccccc3nc2C(F)(F)/C=C/CO)CN1]

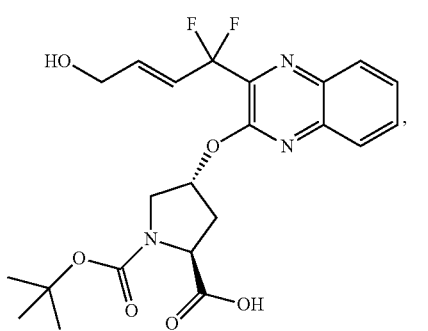 [SMILES: CC(C)(C)OC(=O)N1C[C@H](Oc2nc3ccccc3nc2C(F)(F)/C=C/CO)C[C@H]1C(=O)O]

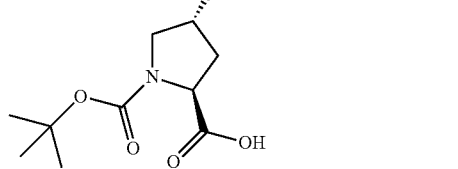, and

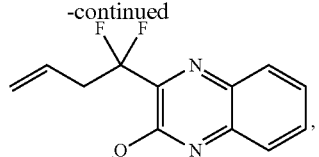, or a salt thereof.

In certain embodiments, the invention relates to any one of the compounds described herein, wherein the compound is

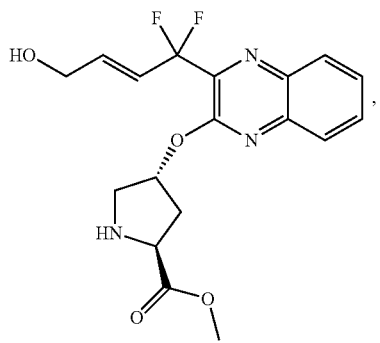

or a salt thereof.

In certain embodiments, the invention relates to any one of the compounds described herein, wherein the compound is

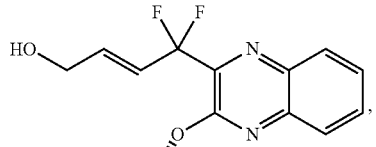

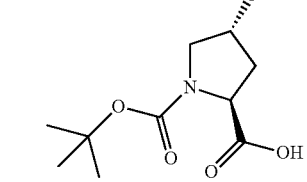, or a salt thereof.

In certain embodiments, the invention relates to any one of the compounds described herein, wherein the compound is

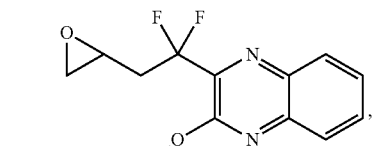

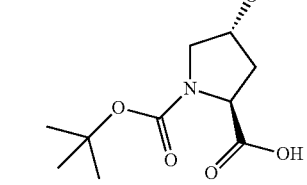

or a salt thereof.

In certain embodiments, the invention relates to any one of the compounds described herein, wherein the compound is

or a salt thereof.

In certain embodiments, the invention relates to any one of the compounds described herein, wherein the compound is

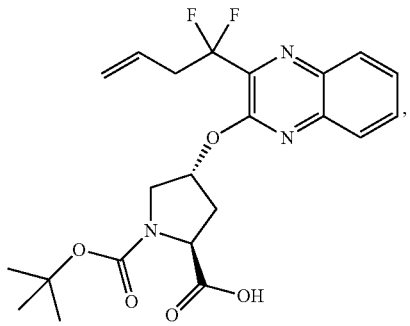 [SMILES: C=CCC(F)(F)c1nc2ccccc2nc1O[C@@H]1C[C@@H](C(=O)O)N(C(=O)OC(C)(C)C)C1]

or a salt thereof.

In certain embodiments, the invention relates to any one of the compounds described herein, wherein the compound is

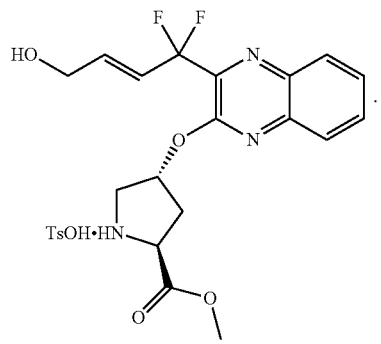

In certain embodiments, the invention relates to any one of the compounds described herein, wherein the compound is

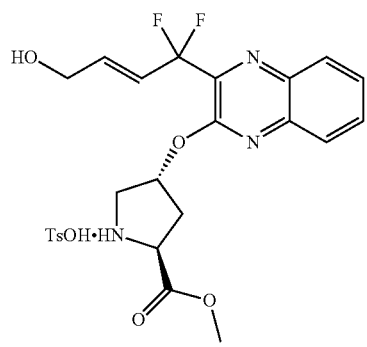

in crystalline form.

In certain embodiments, the invention relates to any one of the compounds described herein, wherein the compound is

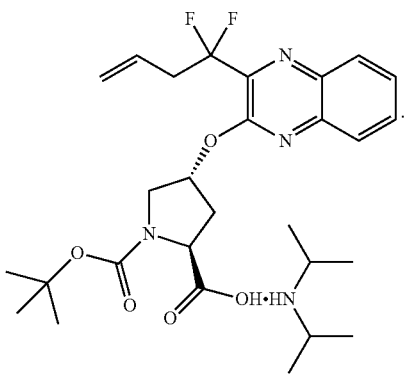

In certain embodiments, the invention relates to any one of the compounds described herein, wherein the compound is

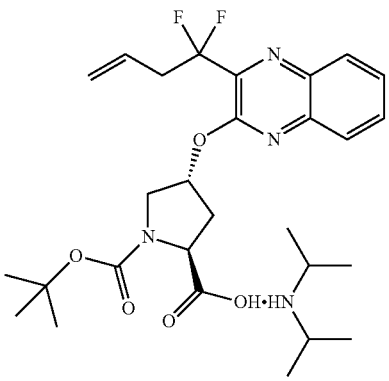

in crystalline form.

In certain embodiments, the invention relates to a compound selected from:

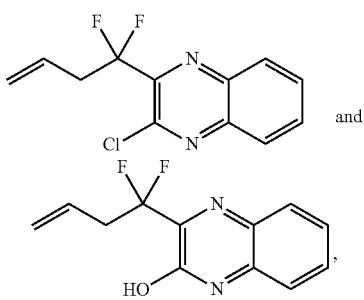

or a salt thereof.

In certain embodiments, the invention relates to any one of the compounds described herein, wherein the compound is

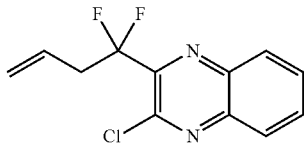 [SMILES: C=CCC(F)(F)c1nc2ccccc2nc1Cl]

or a salt thereof. In certain embodiments, the invention relates to any one of the compounds described herein, wherein the compound is

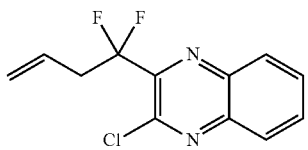 [SMILES: C=CCC(F)(F)c1nc2ccccc2nc1Cl]

in crystalline form.

In certain embodiments, the invention relates to any one of the compounds described herein, wherein the compound is

or a salt thereof. In certain embodiments, the invention relates to any one of the compounds described herein, wherein the compound is

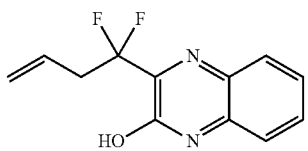 [SMILES: C=CCC(F)(F)c1nc2ccccc2nc1O]

in crystalline form.

In certain embodiments, the invention relates to a compound selected from:

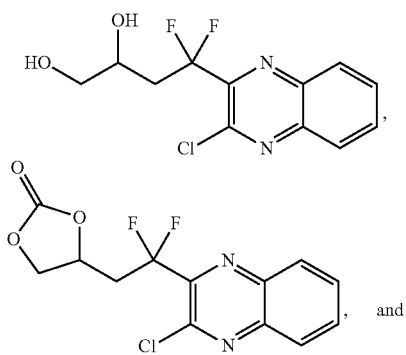

and

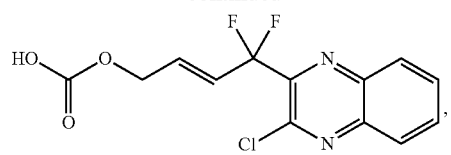

or a salt thereof.

In certain embodiments, the invention relates to any one of the compounds described herein, wherein the compound is

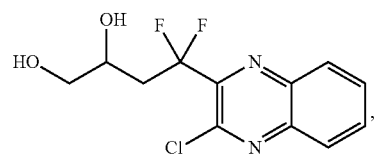 [SMILES: OCC(O)CC(F)(F)c1nc2ccccc2nc1Cl]

or a salt thereof. In certain embodiments, the invention relates to any one of the compounds described herein, wherein the compound is

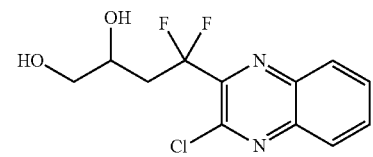 [SMILES: OCC(O)CC(F)(F)c1nc2ccccc2nc1Cl]

in crystalline form.

In certain embodiments, the invention relates to any one of the compounds described herein, wherein the compound is

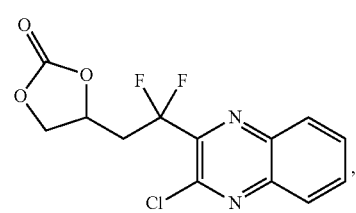 [SMILES: O=C1OCC(CC(F)(F)c2nc3ccccc3nc2Cl)O1]

or a salt thereof. In certain embodiments, the invention relates to any one of the compounds described herein, wherein the compound is

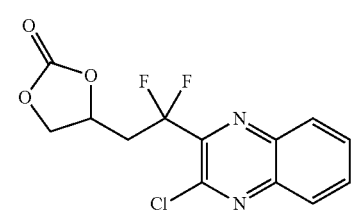 [SMILES: O=C1OCC(CC(F)(F)c2nc3ccccc3nc2Cl)O1]

in crystalline form.

In certain embodiments, the invention relates to any one of the compounds described herein, wherein the compound is

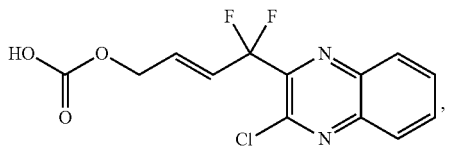 [SMILES: O=C(O)OC/C=C/C(F)(F)c1nc2ccccc2nc1Cl]

or a salt thereof. In certain embodiments, the invention relates to any one of the compounds described herein, wherein the compound is

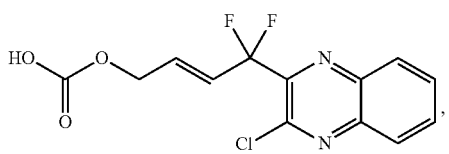 [SMILES: O=C(O)OC/C=C/C(F)(F)c1nc2ccccc2nc1Cl]

or a salt thereof, in crystalline form.

In certain embodiments, the invention relates to any one of the compounds described herein, wherein the compound is

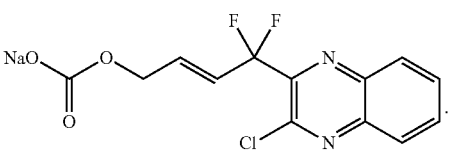

In certain embodiments, the invention relates to any one of the compounds described herein, wherein the compound is

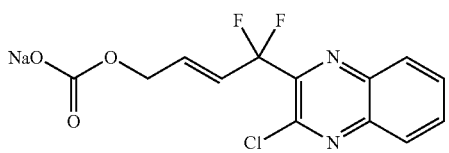

in crystalline form.

In certain embodiments, the invention relates to a compound selected from:

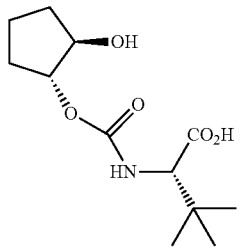 [SMILES: CC(C)(C)[C@H](NC(=O)O[C@@H]1CCC[C@H]1O)C(=O)O] and 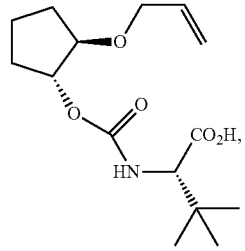

or a salt thereof.

In certain embodiments, the invention relates to any one of the compounds described herein, wherein the compound is

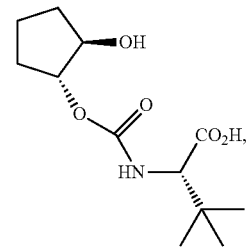

or a salt thereof.

In certain embodiments, the invention relates to any one of the compounds described herein, wherein the compound is

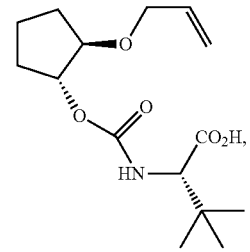 [SMILES: C=CCO[C@@H]1CCC[C@H]1OC(=O)N[C@H](C(=O)O)C(C)(C)C]

or a salt thereof.

In certain embodiments, the invention relates to any one of the compounds described herein, wherein the compound is

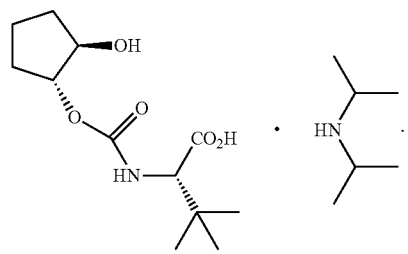

In certain embodiments, the invention relates to any one of the compounds described herein, wherein the compound is

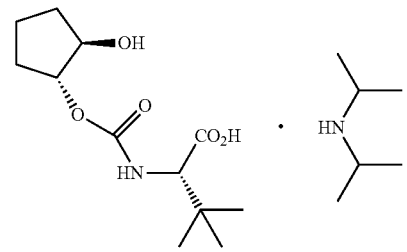

in crystalline form.

In certain embodiments, the invention relates to any one of the compounds described herein, wherein the compound is

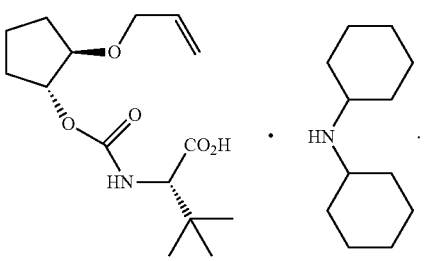

In certain embodiments, the invention relates to any one of the compounds described herein, wherein the compound is

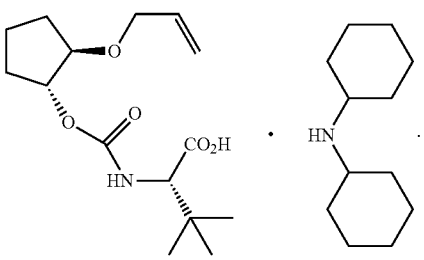

in crystalline form.

In certain embodiments, the invention relates to a compound selected from:

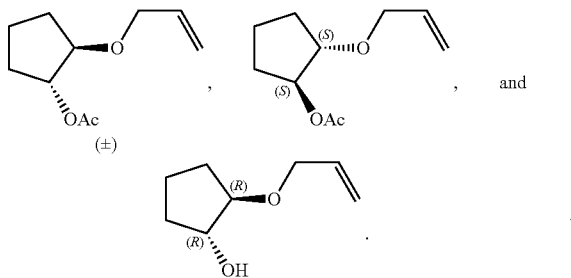

In certain embodiments, the invention relates to any one of the compounds described herein, wherein the compound is

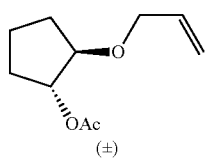

In certain embodiments, the invention relates to any one of the compounds described herein, wherein the compound is

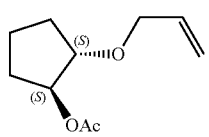

In certain embodiments, the invention relates to any one of the compounds described herein, wherein the compound is

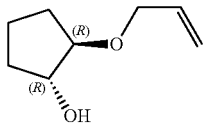

IV. Exemplary Methods and Uses

The compounds and processes of the present invention will be better understood in connection with the following illustrative methods by which the compounds of the invention may be prepared. It will be understood that any of the reactions described herein, in any of its variations, can be combined with one or more of the other reactions, in any of their respective variations, substantially in analogy with Scheme 1 above.

In certain embodiments, the invention relates to a method according to reaction scheme A:

Scheme A

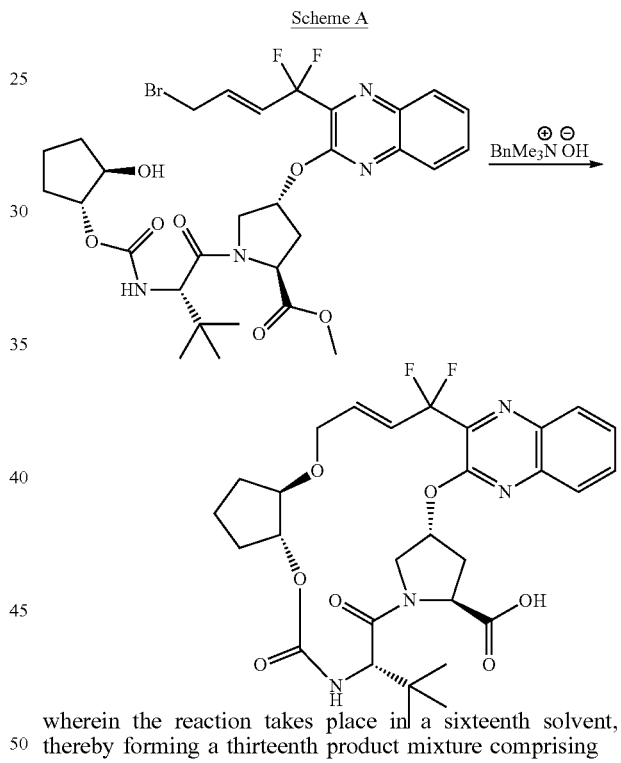

wherein the reaction takes place in a sixteenth solvent, thereby forming a thirteenth product mixture comprising

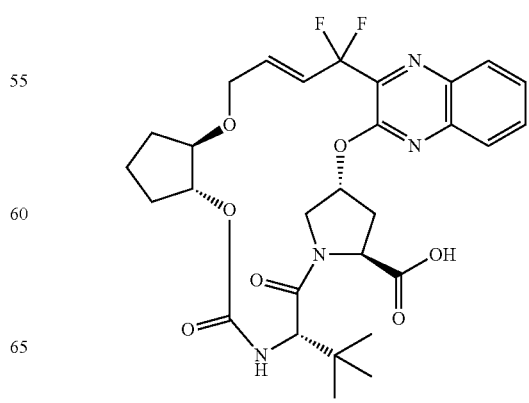

In certain such embodiments, the quaternary ammonium hydroxide can be replaced with a different base, such as LiOH, NaOH, KOH, or another quaternary ammonium hydroxide, or a mixture thereof.

In certain such embodiments, the quaternary ammonium hydroxide can be replaced with another organic-soluble base, such as another quaternary ammonium hydroxide.

In certain embodiments, the invention relates to any one of the methods described herein including the reaction of scheme A, wherein the sixteenth solvent comprises dimethylacetamide (DMA), toluene, xylenes, THF, H₂O, dimethylformamide (DMF), methyl tert-butyl ether, ethyl acetate, dioxane, acetonitrile, or DMSO, or a mixture thereof, preferably THF or H₂O or a mixture thereof, or acetonitrile or H₂O or a mixture thereof.

In certain embodiments, the invention relates to any one of the methods described herein including the reaction of scheme A, wherein the reaction of scheme A takes place at a sixteenth temperature, such as wherein the sixteenth temperature is from about −20° C. to about 30° C., or from about −20° C. to about 10° C., for example about −20° C., about −15° C., about −10° C., about −5° C., about 0° C., about 5° C., about 10° C., about 15° C., about 20° C., or about 25° C., preferably from −5° C. to 5° C., most preferably about 0° C.

In certain embodiments, the invention relates to any one of the methods described herein including the reaction of scheme A, wherein the reaction of scheme A takes place over a ninth period of time, such as wherein the ninth period of time is from about 1 h to about 40 h, for example, about 1 h, about 5 h, about 10 h, about 15 h, about 20 h, about 25 h, about 30 h, about 35 h, or about 40 h, preferably about 10 h to about 30 h, most preferably about 20 h.

In certain embodiments, the invention relates to any one of the methods described herein that include the reaction of scheme A, further comprising isolating

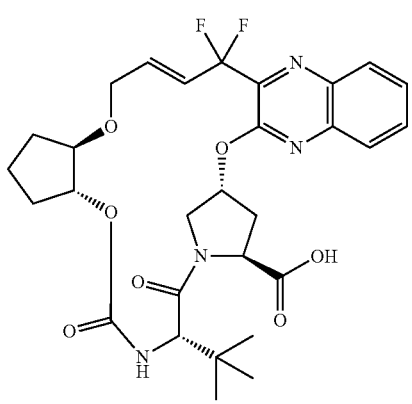 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)O)N(C2)C1=O]

or a salt thereof from the thirteenth product mixture, thereby obtaining substantially pure

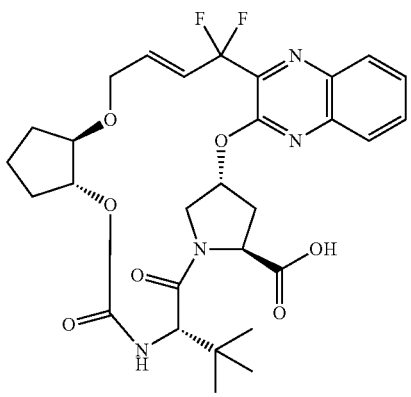 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)O)N(C2)C1=O]

or a salt thereof.

In certain embodiments, the invention relates to any one of the methods described herein, further comprising recrystallizing

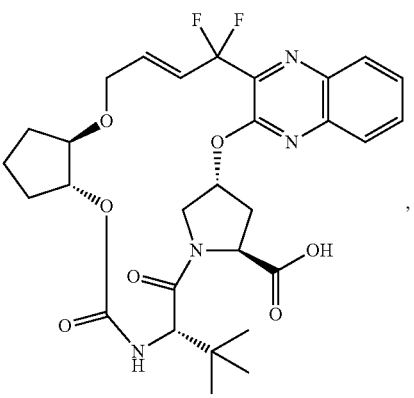 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)O)N(C2)C1=O]

or a salt thereof, to obtain the compound in a crystalline form.

In certain embodiments, the invention relates to a method according to reaction scheme B:

Scheme B

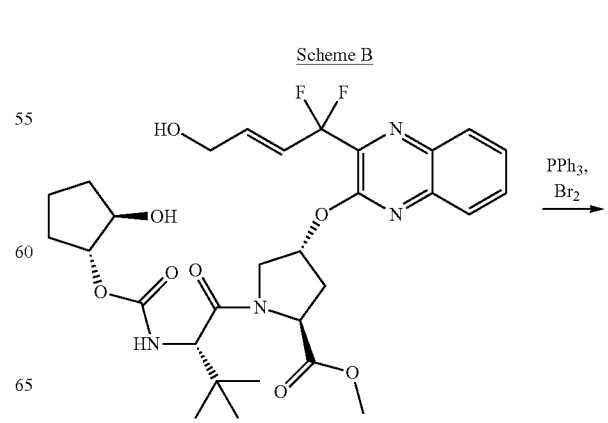

-continued

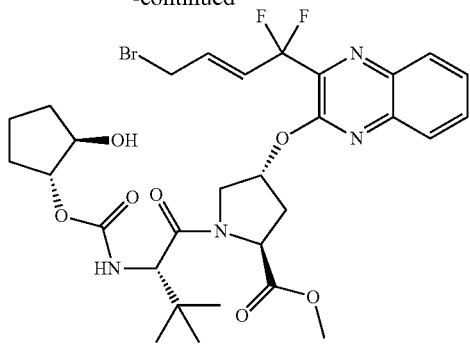

wherein the reaction takes place in a fifteenth solvent, thereby forming a twelfth product mixture comprising

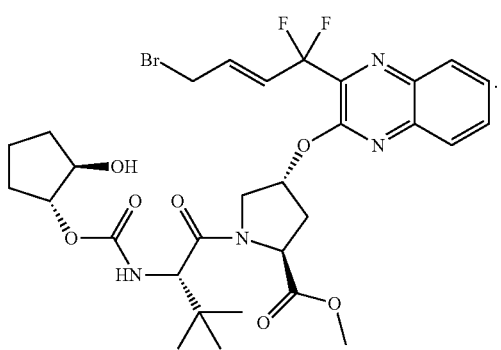 [SMILES: COC(=O)[C@@H]1C[C@@H](Oc2nc3ccccc3nc2C(F)(F)/C=C/CBr)CN1C(=O)[C@@H](NC(=O)O[C@@H]1CCC[C@H]1O)C(C)(C)C]

In certain embodiments, the invention relates to any one of the methods described herein including the reaction of scheme B, wherein the fifteenth solvent comprises toluene, dichloromethane, THF, acetone, heptane, hexane, methyl tert-butyl ether, ethyl acetate, dioxane, DMF, DMA, acetonitrile, or DMSO, or a mixture thereof, preferably toluene, acetonitrile, or dichloromethane or a mixture thereof.

In certain embodiments, the invention relates to any one of the methods described herein including the reaction of scheme B, wherein the reaction of scheme B takes place at a fifteenth temperature, such as from about −20° C. to about 10° C., for example about −20° C., about −15° C., about −10° C., about −5° C., about 0° C., about 5° C., or about 10° C., preferably about −10° C. to about 10° C., most preferably about 0° C.

In certain embodiments, the invention relates to any one of the methods described herein, further comprising isolating

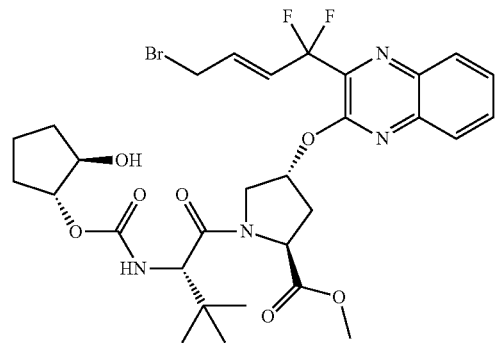 [SMILES: COC(=O)[C@@H]1C[C@@H](Oc2nc3ccccc3nc2C(F)(F)/C=C/CBr)CN1C(=O)[C@@H](NC(=O)O[C@@H]1CCC[C@H]1O)C(C)(C)C]

from the twelfth product mixture, thereby obtaining substantially pure

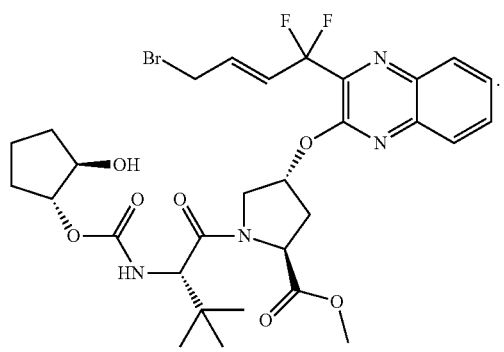 [SMILES: COC(=O)[C@@H]1C[C@@H](Oc2nc3ccccc3nc2C(F)(F)/C=C/CBr)CN1C(=O)[C@@H](NC(=O)O[C@@H]1CCC[C@H]1O)C(C)(C)C]

In certain embodiments, the invention relates to a method according to reaction scheme C:

Scheme C

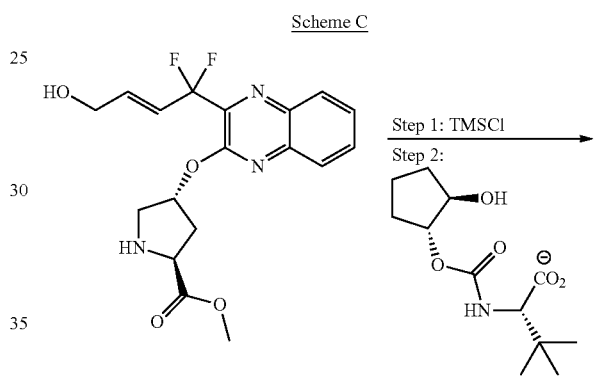

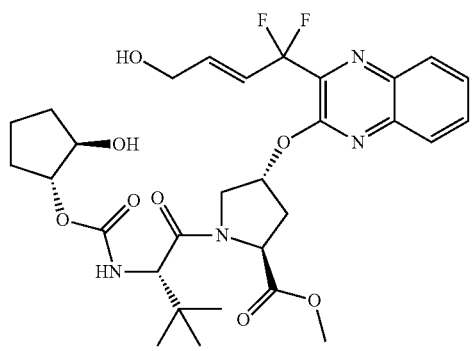

wherein Step 1 of the reaction takes place in a thirteenth solvent in the presence of a seventh base; and Step 2 of the reaction takes place in a fourteenth solvent, thereby forming an eleventh product mixture comprising

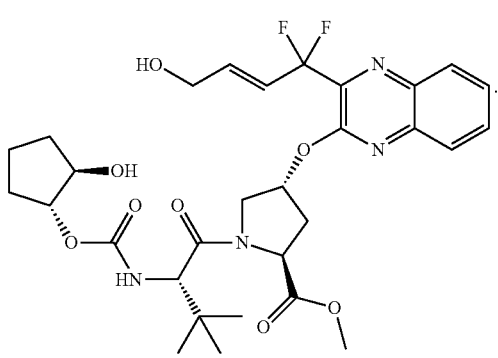 [SMILES: COC(=O)[C@@H]1C[C@@H](Oc2nc3ccccc3nc2C(F)(F)/C=C/CO)CN1C(=O)[C@@H](NC(=O)O[C@@H]1CCC[C@H]1O)C(C)(C)C]

In certain such embodiments, the TMSCl is replaced by another silylating reagent, such as TESCl, TMSOTf, TMSBr, TMSI, or any other suitable silylating reagent.

In certain such embodiments, the TMSCl is replaced by another source of TMS, such as TMSOTf, TMSBr, TMSI, or any other suitable trimethylsilylating reagent.

In certain embodiments, the invention relates to any one of the methods described herein including reaction scheme C, wherein the thirteenth solvent is DMA, toluene, dichloromethane, THF, acetone, heptane, methyl tert-butyl ether, ethyl acetate, dioxane, DMF, acetonitrile, or DMSO or a mixture thereof, preferably acetonitrile or DMA.

In certain embodiments, the invention relates to any one of the methods described herein including reaction scheme C, wherein the seventh base is N-methylmorpholine, triethylamine, $Et_2NH$, $(iPr)_2EtN$, or $(iPr)_2NH$ or a mixture thereof, preferably $(iPr)_2EtN$.

In certain embodiments, the invention relates to any one of the methods described herein including reaction scheme C, wherein the seventh base is N-methylmorpholine, triethylamine, or $(iPr)_2EtN$, preferably $(iPr)_2EtN$.

In certain embodiments, the invention relates to any one of the methods described herein including reaction scheme C, wherein Step 1 of reaction scheme C takes place at a thirteenth temperature, such as from about −10° C. to about 20° C., for example about −10° C., about −5° C., about 0° C., about 5° C., about 10° C., about 15° C., or about 20° C., preferably about −10° C. to about 10° C., most preferably about 0° C.

In certain embodiments, the invention relates to any one of the methods described herein including reaction scheme C, wherein the fourteenth solvent is DMA, toluene, dichloromethane, THF, acetone, heptane, methyl tert-butyl ether, ethyl acetate, dioxane, DMF, acetonitrile, or DMSO or a mixture thereof, preferably acetonitrile or DMA.

In certain embodiments, the invention relates to any one of the methods described herein including reaction scheme C, wherein Step 2 of reaction scheme C takes place at a fourteenth temperature, such as from about 0° C. to about 40° C., for example, about 0° C., about 5° C., about 10° C., about 15° C., about 20° C., about 25° C., about 30° C., about 35° C., or about 40° C., preferably about 10° C. to about 30° C., most preferably about 20° C.

In certain embodiments, the invention relates to any one of the methods described herein including reaction scheme C, wherein Step 2 of the reaction takes place over an eighth period of time, such as from about 1 h to about 40 h, for example, about 1 h, about 5 h, about 10 h, about 15 h, about 20 h, about 25 h, about 30 h, about 35 h, or about 40 h, preferably about 15 h.

In certain embodiments, the invention relates to any one of the methods described herein, further comprising isolating

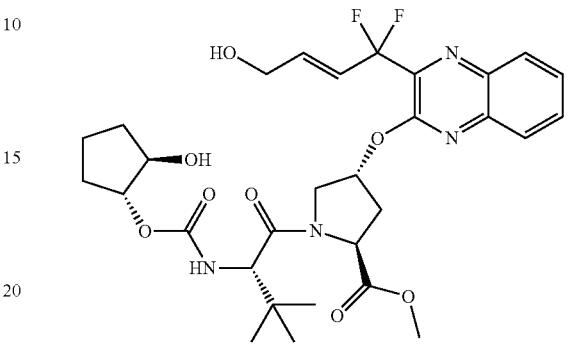

from the eleventh product mixture, thereby obtaining substantially pure

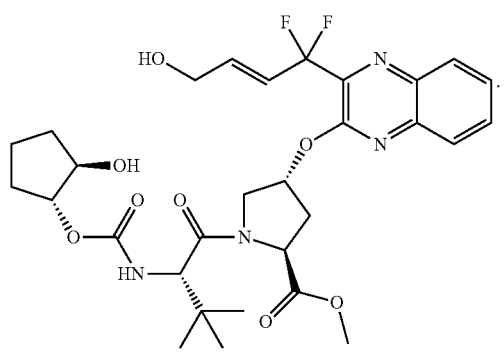 [SMILES: COC(=O)[C@@H]1C[C@@H](Oc2nc3ccccc3nc2C(F)(F)/C=C/CO)CN1C(=O)[C@@H](NC(=O)O[C@@H]1CCC[C@H]1O)C(C)(C)C]

In certain embodiments, the invention relates to a method according to reaction scheme D:

Scheme D

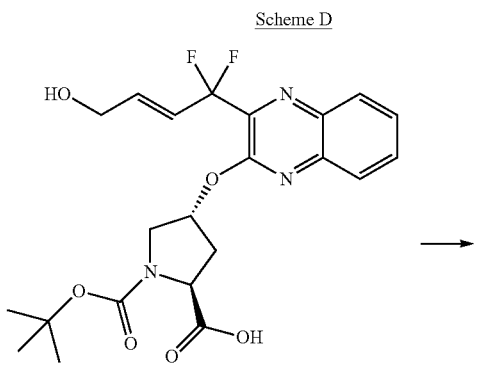

-continued

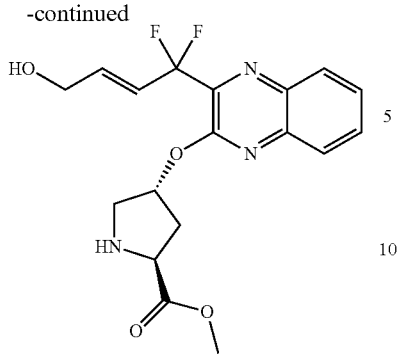

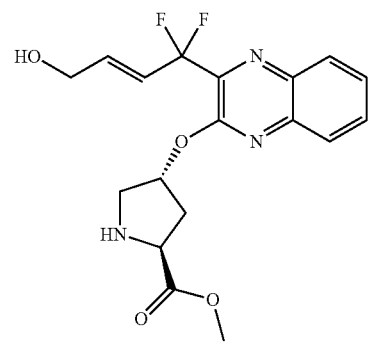

wherein the reaction takes place in a twelfth solvent in the presence of a second acid, thereby forming a tenth product mixture comprising

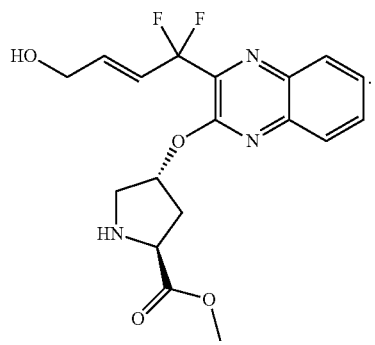 [SMILES: COC(=O)[C@@H]1C[C@@H](Oc2nc3ccccc3nc2C(F)(F)/C=C/CO)CN1]

In certain embodiments, the invention relates to any one of the methods described herein including reaction scheme D, wherein the twelfth solvent is dioxane, acetonitrile, cyclopentylmethyl ether (CPME), methanol, ethanol, isopropanol, n-propanol, water, formic acid, acetic acid, or n-butanol or a mixture thereof, preferably methanol or CPME or a mixture thereof.

In certain embodiments, the invention relates to any one of the methods described herein including reaction scheme D, wherein the second acid is HCl (e.g., HCl generated from thionyl chloride), HBr, $H_2SO_4$, $CH_3SO_3H$, or $CF_3SO_3H$, preferably HCl.

In certain embodiments, the invention relates to any one of the methods described herein including reaction scheme D, wherein the reaction of scheme D takes place at a twelfth temperature, such as from about 10° C. to about 40° C., for example, about 10° C., about 15° C., about 20° C., about 25° C., about 30° C., about 35° C., or about 40° C., preferably from about 15° C. to about 30° C., most preferably about 23° C.

In certain embodiments, the invention relates to any one of the methods described herein including reaction scheme D, wherein the reaction of scheme D takes place over a seventh period of time, such as from about 1 h to about 40 h, for example, about 1 h, about 5 h, about 10 h, about 15 h, about 20 h, about 25 h, about 30 h, about 35 h, or about 40 h, preferably about 5 h to about 25 h, most preferably about 15 h.

In certain embodiments, the invention relates to any one of the methods described herein, further comprising contacting with an acid, thereby forming a salt, wherein preferably the acid is TsOH or HCl.

In certain embodiments, the invention relates to a method according to reaction scheme E:

Scheme E

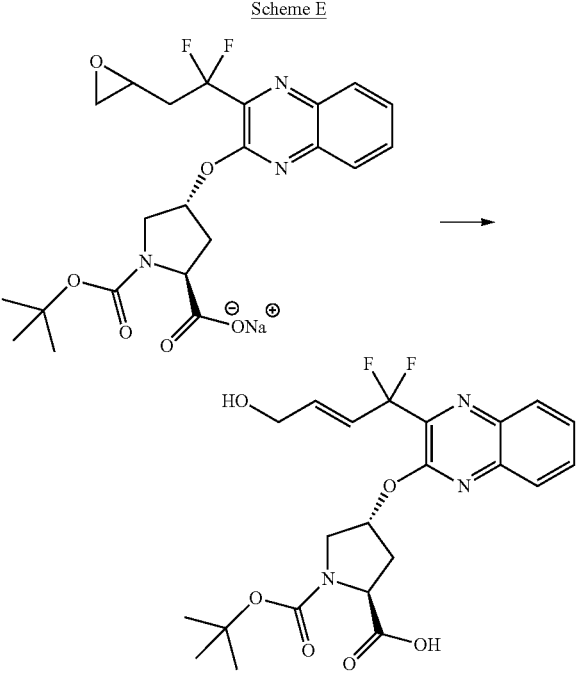

wherein the reaction takes place in an eleventh solvent in the presence of a sixth base, thereby forming a ninth product mixture comprising

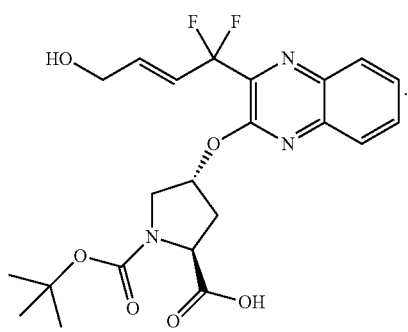 [SMILES: CC(C)(C)OC(=O)N1C[C@H](Oc2nc3ccccc3nc2C(F)(F)/C=C/CO)C[C@H]1C(=O)O]

In certain embodiments, the invention relates to any one of the methods described herein including reaction scheme E, wherein the eleventh solvent is toluene, DMA, THF, DMF, methyl tert-butyl ether, ethyl acetate, dioxane, acetonitrile, or DMSO or a mixture thereof, preferably THF or toluene.

In certain embodiments, the invention relates to any one of the methods described herein including reaction scheme E, wherein the sixth base is LiOtBu, NaOtBu, KOtBu, potassium t-amylate, LiHMDS, NaHMDS, KHMDS, or lithium diisopropylamide, preferably LiHMDS.

In certain embodiments, the invention relates to any one of the methods described herein including reaction scheme E, wherein the reaction of scheme E takes place at an eleventh temperature, such as from about −20° C. to about 20° C. or from about −10° C. to about 20° C., for example about −10° C., about −5° C., about 0° C., about 5° C., about 10° C., about 15° C., or about 20° C., preferably about −5° C. to about 15° C., most preferably about 5° C.

In certain embodiments, the invention relates to any one of the methods described herein including reaction scheme E, wherein the reaction of scheme E takes place over a sixth period of time, such as from about 1 h to about 40 h, for example, about 1 h, about 5 h, about 10 h, about 15 h, about 20 h, about 25 h, about 30 h, about 35 h, or about 40 h, preferably about 1 h to about 30 h or about 10 h to about 30 h, most preferably about 20 h.

In certain embodiments, the invention relates to any one of the methods described herein, further comprising isolating

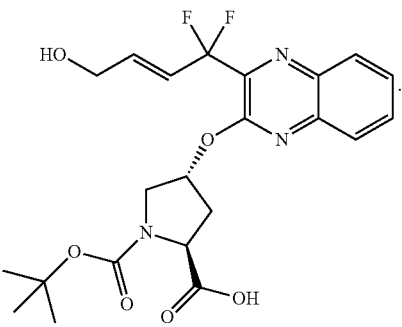 [SMILES: CC(C)(C)OC(=O)N1C[C@H](Oc2nc3ccccc3nc2C(F)(F)/C=C/CO)C[C@H]1C(=O)O]

from the ninth product mixture, thereby obtaining substantially pure

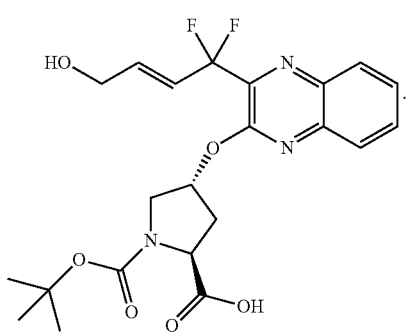 [SMILES: CC(C)(C)OC(=O)N1C[C@H](Oc2nc3ccccc3nc2C(F)(F)/C=C/CO)C[C@H]1C(=O)O]

In certain embodiments, the invention relates to a method according to reaction scheme E':

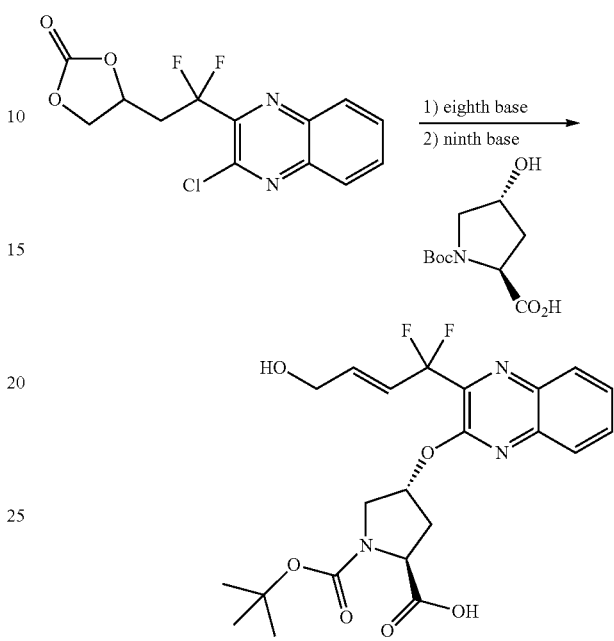

wherein step (1) takes place in a nineteenth solvent in the presence of an eighth base, and step (2) takes place in a twentieth solvent in the presence of a ninth base, thereby forming a sixteenth product mixture comprising In certain embodiments, the invention relates to any one of the methods described herein including reaction scheme E', wherein the nineteenth solvent is DMA, THF, DMF, methyl tert-butyl ether, ethyl acetate, dioxane, acetonitrile, or DMSO or a mixture thereof, preferably THF.

In certain embodiments, the invention relates to any one of the methods described herein including reaction scheme E', wherein the eighth base is LiOtBu, NaOtBu, KOtBu, potassium t-amylate, LiHMDS, NaHMDS, KHMDS, or lithium diisopropylamide, preferably NaHMDS.

In certain embodiments, the invention relates to any one of the methods described herein including reaction scheme E', wherein the twentieth solvent is water DMA, THF, DMF, methyl tert-butyl ether, ethyl acetate, dioxane, acetonitrile, or DMSO or a mixture thereof, preferably THF or water or a mixture thereof.

In certain embodiments, the invention relates to any one of the methods described herein including reaction scheme E', wherein the ninth base is NaOtBu, LiOtBu, KOtBu, NaOH, LiOH, KOH, NaH, LiH, or KH, preferably KOtBu.

In certain embodiments, the invention relates to any one of the methods described herein, further comprising contacting

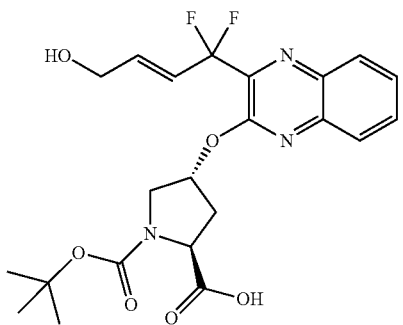 [SMILES: CC(C)(C)OC(=O)N1C[C@H](Oc2nc3ccccc3nc2C(F)(F)/C=C/CO)C[C@H]1C(=O)O]

with a base, preferably an amine base such as benzhydrylamine, thereby forming a salt.

In certain embodiments, the invention relates to any one of the methods described herein, further comprising crystallizing

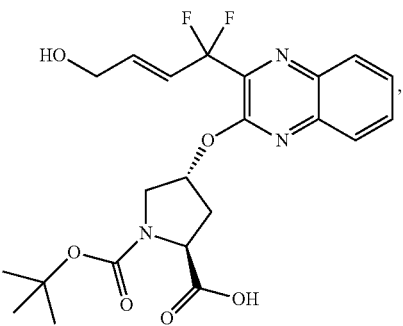 [SMILES: CC(C)(C)OC(=O)N1C[C@H](Oc2nc3ccccc3nc2C(F)(F)/C=C/CO)C[C@H]1C(=O)O]

or a salt thereof, to obtain the compound in a crystalline form.

In certain embodiments, the invention relates to a method according to reaction scheme F:

Scheme F

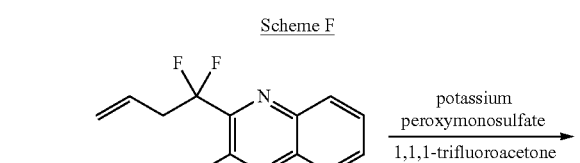

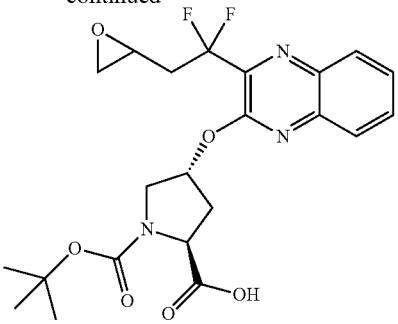

wherein the reaction takes place in a tenth solvent in the presence of a fifth base, thereby forming an eighth product mixture comprising

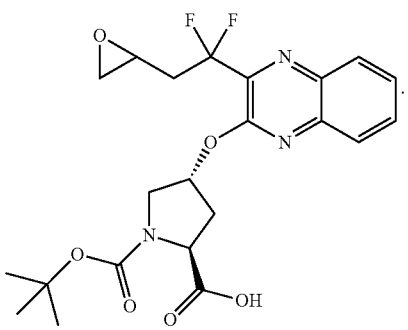 [SMILES: CC(C)(C)OC(=O)N1C[C@H](Oc2nc3ccccc3nc2C(F)(F)CC2CO2)C[C@H]1C(=O)O]

In certain embodiments, the invention relates to any one of the methods described herein including reaction scheme F, wherein the tenth solvent comprises $H_2O$, DMA, toluene, dichloromethane, THF, acetone, heptane, methyl tert-butyl ether, ethyl acetate, dioxane, DMF, acetonitrile, or DMSO, preferably $H_2O$, acetonitrile, or ethyl acetate, or a mixture thereof.

In certain embodiments, the invention relates to any one of the methods described herein including reaction scheme F, wherein the fifth base is $NaHCO_3$, $NaHSO_3$, $NaH_2PO_4$, $KHCO_3$, $KHSO_3$, $KH_2PO_4$, $LiHCO_3$, $LiHSO_3$, $LiH_2PO_4$, or sodium acetate, preferably $NaHCO_3$.

In certain embodiments, the invention relates to any one of the methods described herein including reaction scheme F, wherein the reaction takes place at a tenth temperature; and the tenth temperature is from about $-10°$ C. to about $20°$ C., for example about $-10°$ C., about $-5°$ C., about $0°$ C., about $5°$ C., about $10°$ C., about $15°$ C., or about $20°$ C., preferably from about $-10°$ C. to about $10°$ C., most preferably about $0°$ C.

In certain embodiments, the invention relates to any one of the methods described herein, further comprising contacting

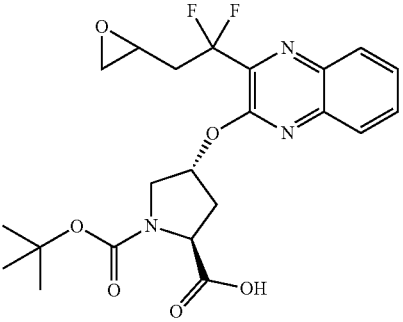 [SMILES: CC(C)(C)OC(=O)N1C[C@H](Oc2nc3ccccc3nc2C(F)(F)CC2CO2)C[C@H]1C(=O)O]

with a base, thereby forming a salt.

In certain embodiments, the invention relates to a method according to reaction scheme F':

Scheme F'

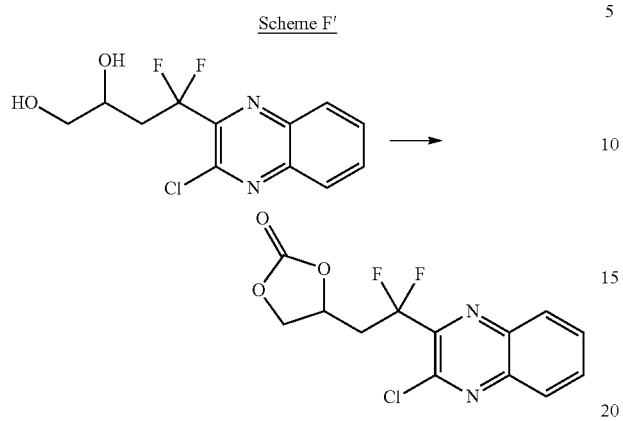

wherein the reaction takes place in a eighteenth solvent in the presence of a reagent, thereby forming an fifteenth product mixture comprising

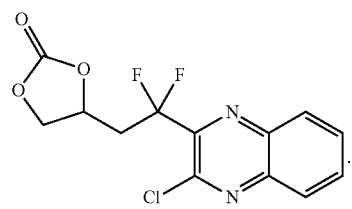

In certain embodiments, the invention relates to any one of the methods described herein including reaction scheme F', wherein the eighteenth solvent is DMA, THF, DMF, methyl tert-butyl ether, ethyl acetate, dioxane, acetonitrile, or DMSO or a mixture thereof, preferably acetonitrile or ethyl acetate or a mixture thereof.

In certain embodiments, the invention relates to any one of the methods described herein including reaction scheme F', wherein the reagent is triphosgene, phosgene gas, carbonyl diimidazole, or another doubly activated analog of carbonic acid, preferably carbonyl diimidazole.

In certain embodiments, the invention relates to any one of the methods described herein, further comprising crystallizing

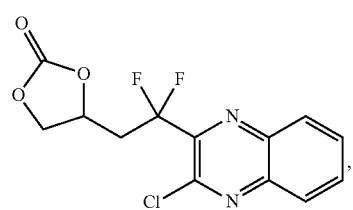 [SMILES: O=C1OCC(CC(F)(F)c2nc3ccccc3nc2Cl)O1]

or a salt thereof, to obtain the compound in a crystalline form.

In certain embodiments, the invention relates to a method according to reaction scheme G:

Scheme G

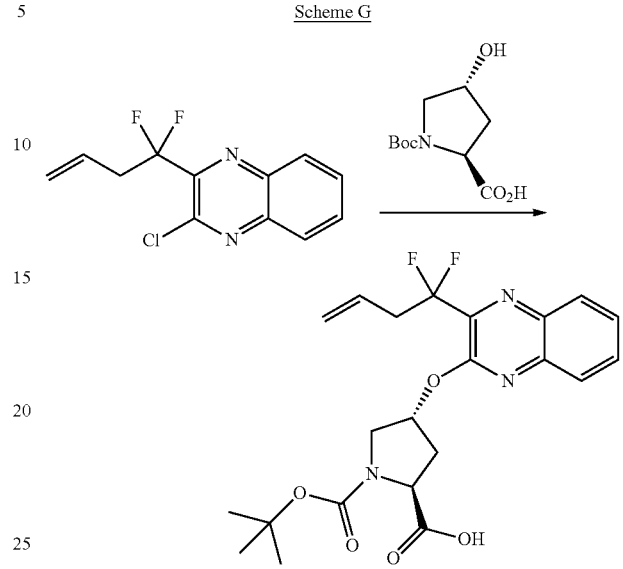

wherein the reaction takes place in a ninth solvent in the presence of a fourth base, thereby forming a seventh product mixture comprising

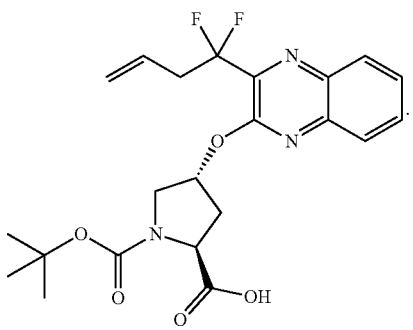 [SMILES: C=CCC(F)(F)c1nc2ccccc2nc1O[C@@H]1C[C@@H](C(=O)O)N(C(=O)OC(C)(C)C)C1]

In certain embodiments, the invention relates to any one of the methods described herein including reaction scheme G, wherein the ninth solvent is DMA, THF, DMF, methyl tert-butyl ether, ethyl acetate, dioxane, acetonitrile, or DMSO or a mixture thereof, preferably THF.

In certain embodiments, the invention relates to any one of the methods described herein including reaction scheme G, wherein the fourth base is NaOtBu, LiOtBu, KOtBu, NaOH, LiOH, KOH, NaH, LiH, or KH, preferably NaH.

In certain embodiments, the invention relates to any one of the methods described herein including reaction scheme G, wherein the reaction of scheme G takes place at a ninth temperature, such as from about −10° C. to about 30° C., for example about −10° C., about −5° C., about 0° C., about 5° C., about 10° C., about 15° C., about 20° C., about 25° C., or about 30° C., preferably from about 0° C. to about 25° C. or from about 0° C. to about 20° C., most preferably about 10° C. or about 20° C.

In certain embodiments, the invention relates to any one of the methods described herein, further comprising contacting

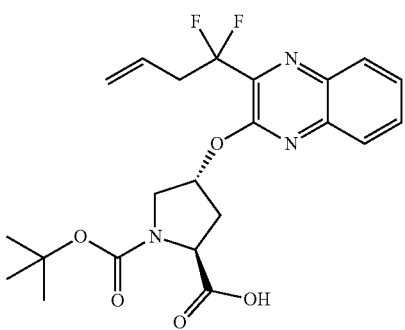 [SMILES: C=CCC(F)(F)c1nc2ccccc2nc1O[C@@H]1C[C@@H](C(=O)O)N(C(=O)OC(C)(C)C)C1]

with a base, thereby forming a salt, wherein preferably the base is diisopropylamine.

In certain embodiments, the invention relates to any one of the methods described herein, further comprising crystallizing

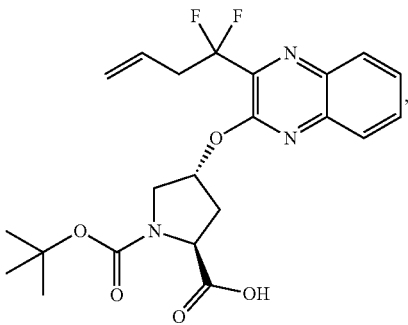 [SMILES: C=CCC(F)(F)c1nc2ccccc2nc1O[C@@H]1C[C@@H](C(=O)O)N(C(=O)OC(C)(C)C)C1]

or a salt thereof, to obtain the compound in a crystalline form.

In certain embodiments, the invention relates to a method according to reaction scheme G':

Scheme G'

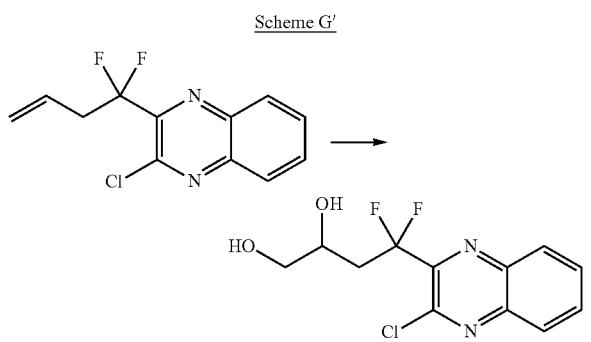

wherein the reaction takes place in a seventeenth solvent in the presence of an oxidant, thereby forming a fourteenth product mixture comprising

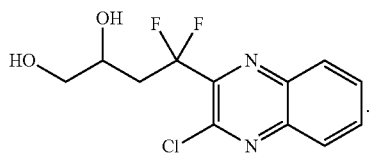 [SMILES: OCC(O)CC(F)(F)c1nc2ccccc2nc1Cl]

In certain embodiments, the invention relates to any one of the methods described herein including reaction scheme G', wherein the oxidant comprises an oxidation catalyst.

In certain embodiments, the invention relates to any one of the methods described herein including reaction scheme G', wherein the oxidant comprises a stoichiometric oxidant.

In certain embodiments, the invention relates to any one of the methods described herein including reaction scheme G', wherein the oxidant comprises an oxidation catalyst and a stoichiometric oxidant.

In certain embodiments, the invention relates to any one of the methods described herein including reaction scheme G', wherein the oxidation catalyst is a source of osmium tetroxide.

In certain embodiments, the invention relates to any one of the methods described herein including reaction scheme G', wherein the source of osmium tetroxide is preferably $K_2OsO_4$.

In certain embodiments, the invention relates to any one of the methods described herein including reaction scheme G', wherein the stoichiometric oxidant is a trialkylammonium N-oxide, for example, N-methylmorpholine-N-oxide (NMO) or trimethylamine N-oxide, preferably N-methylmorpholine N-oxide.

In certain embodiments, the invention relates to any one of the methods described herein including reaction scheme G', wherein the oxidant is a stoichiometric oxidant, for example or preferably potassium permanganate.

In certain embodiments, the invention relates to any one of the methods described herein including reaction scheme G', wherein the seventeenth solvent is water, DMA, toluene, THF, acetone, heptane, hexane, methyl tert-butyl ether, ethyl acetate, dioxane, DMF, acetonitrile, or DMSO or a mixture thereof, preferably ethyl acetate or water or a mixture thereof.

In certain embodiments, the invention relates to any one of the methods described herein, further comprising crystallizing

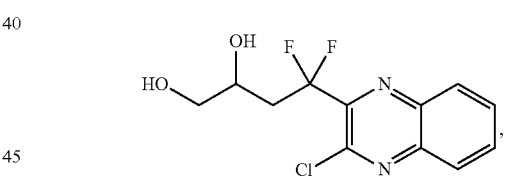

or a salt thereof, to obtain the compound in a crystalline form.

In certain embodiments, the invention relates to a method according to reaction scheme H:

Scheme H

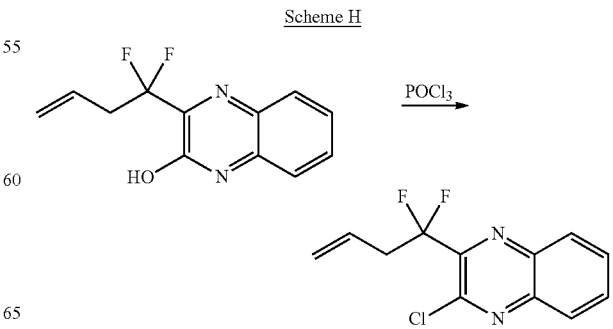

wherein the reaction takes place in an eighth solvent, thereby forming a sixth product mixture comprising

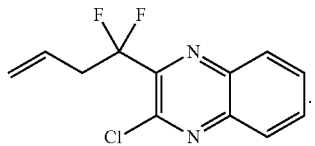 [SMILES: C=CCC(F)(F)c1nc2ccccc2nc1Cl]

In certain embodiments, the invention relates to any one of the methods described herein including reaction scheme H, wherein the eighth solvent is DMA, toluene, THF, acetone, heptane, hexane, methyl tert-butyl ether, ethyl acetate, dioxane, DMF, acetonitrile, or DMSO or a mixture thereof, preferably toluene or DMF or a mixture thereof.

In certain embodiments, the invention relates to any one of the methods described herein including reaction scheme H, wherein the reaction of scheme H takes place at an eighth temperature, such as from about 30° C. to about 60° C., for example, about 30° C., about 35° C., about 40° C., about 45° C., about 50° C., about 55° C., or about 60° C., preferably about 35° C. to about 55° C., most preferably about 45° C.

In certain embodiments, the invention relates to any one of the methods described herein, further comprising isolating

from the sixth product mixture, thereby obtaining substantially pure

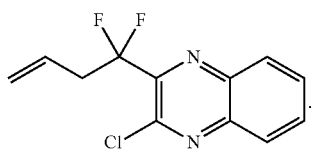

In certain embodiments, the invention relates to any one of the methods described herein, further comprising crystallizing

to obtain the compound in a crystalline form.

In certain embodiments, the invention relates to a method according to reaction scheme I:

Scheme I

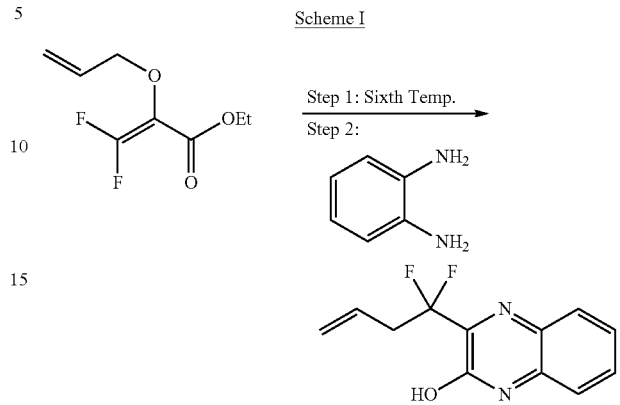

wherein Step 1 of the reaction takes place in a sixth solvent at a sixth temperature to effect a Claisen rearrangement, and Step 2 of the reaction takes place in a seventh solvent at a seventh temperature, thereby forming a fifth product mixture comprising

In certain embodiments, the invention relates to any one of the methods described herein including a reaction of scheme I, wherein the sixth solvent is DMA, toluene, dichloromethane, THF, heptane, methyl tert-butyl ether, ethyl acetate, dioxane, DMF, acetonitrile, or DMSO or a mixture thereof, preferably DMF.

In certain embodiments, the invention relates to any one of the methods described herein including a reaction of scheme I, wherein the sixth temperature is from about 60° C. to about 100° C., for example about 60° C., about 65° C., about 70° C., about 75° C., about 80° C., about 85° C., about 90° C., about 95° C., or about 100° C., preferably about 70° C. to about 90° C., most preferably about 80° C.

In certain embodiments, the invention relates to any one of the methods described herein including a reaction of scheme I, wherein the seventh solvent is DMA, toluene, dichloromethane, THF, acetone, heptane, methyl tert-butyl ether, ethyl acetate, dioxane, DMF, acetonitrile, or DMSO or a mixture thereof, preferably DMF.

In certain embodiments, the invention relates to any one of the methods described herein including a reaction of scheme I, wherein the seventh temperature is from about 0° C. to about 40° C., for example, about 0° C., about 5° C., about 10° C., about 15° C., about 20° C., about 25° C., about 30° C., about 35° C., or about 40° C., preferably about 10° C. to about 30° C., most preferably about 20° C.

In certain embodiments, the invention relates to any one of the methods described herein, further comprising isolating

from the fifth product mixture, thereby obtaining substantially pure

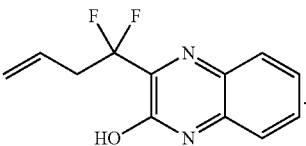 [SMILES: C=CCC(F)(F)c1nc2ccccc2nc1O]

In certain embodiments, the invention relates to any one of the methods described herein, further comprising recrystallizing

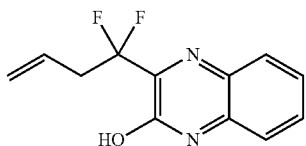 [SMILES: C=CCC(F)(F)c1nc2ccccc2nc1O]

to obtain the compound in a crystalline form.

In certain embodiments, the invention relates to a method according to reaction scheme J:

Scheme J

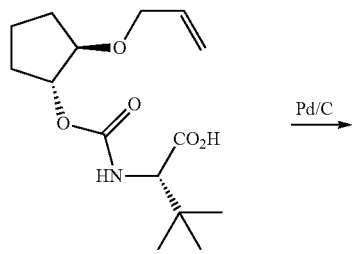 Pd/C →

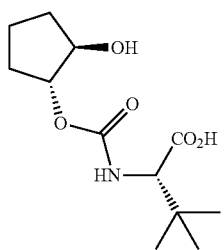

wherein the reaction takes place in a fifth solvent in the presence of a first acid and a hydrogen source, thereby forming a fourth product mixture comprising

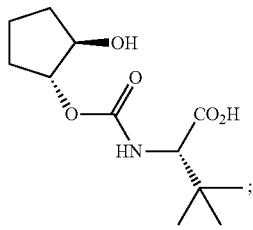 [SMILES: CC(C)(C)[C@H](NC(=O)O[C@@H]1CCC[C@H]1O)C(=O)O]

In certain such embodiments, the Pd/C can be replaced with another suitable hydrogenation catalyst. The hydrogen source is preferably $H_2$, but can be any suitable hydrogen source, such as formic acid or a secondary alcohol, such as isopropanol.

In certain embodiments, the invention relates to any one of the methods described herein including reaction scheme J, wherein the fifth solvent is methanol, ethanol, isopropanol, n-propanol, water, formic acid, acetic acid, or n-butanol or a mixture thereof, preferably methanol or water or a mixture thereof.

In certain embodiments, the invention relates to any one of the methods described herein including reaction scheme J, wherein the first acid is HCl, HBr, $H_2SO_4$, $CH_3SO_3H$, or $CF_3SO_3H$, preferably HCl.

In certain embodiments, the invention relates to any one of the methods described herein including reaction scheme J, wherein the reaction of scheme J takes place at a fifth temperature, such as from about 30° C. to about 90° C., for example, about 30° C., about 35° C., about 40° C., about 45° C., about 50° C., about 55° C., about 60° C., about 65° C., about 70° C., about 75° C., about 80° C., about 85° C., or about 90° C., preferably about 50° C. to about 70° C., most preferably about 60° C.

In certain embodiments, the invention relates to any one of the methods described herein including reaction scheme J, wherein the reaction takes place over a fifth period of time, such as about 1 h to about 12 h, for example, about 1 h, about 2 h, about 3 h, about 4 h, about 5 h, about 6 h, about 7 h, about 8 h, about 9 h, about 10 h, about 11 h, or about 12 h, preferably about 6 h to about 10 h, most preferably about 8 h.

In certain embodiments, the invention relates to any one of the methods described herein, further comprising isolating

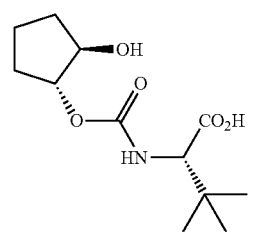

from the fourth product mixture, thereby obtaining substantially pure

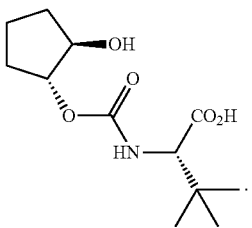 [SMILES: CC(C)(C)[C@H](NC(=O)O[C@@H]1CCC[C@H]1O)C(=O)O]

In certain embodiments, the invention relates to any one of the methods described herein, further comprising contacting

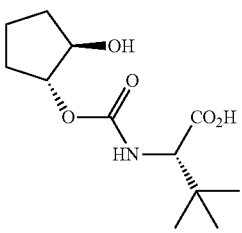 [SMILES: CC(C)(C)[C@H](NC(=O)O[C@@H]1CCC[C@H]1O)C(=O)O]

with a base, thereby forming a salt.

In certain embodiments, the invention relates to any one of the methods described herein, further comprising crystallizing

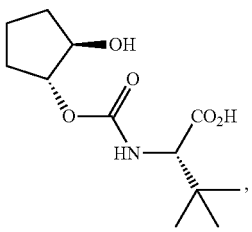 [SMILES: CC(C)(C)[C@H](NC(=O)O[C@@H]1CCC[C@H]1O)C(=O)O]

or a salt thereof, to obtain the compound in a crystalline form.

In certain embodiments, the invention relates to a method according to reaction scheme K:

Scheme K

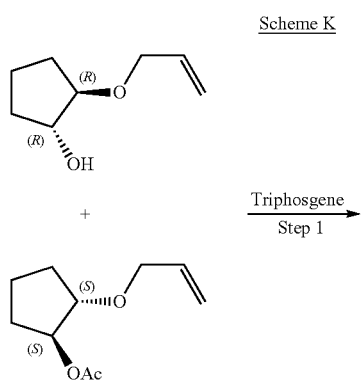

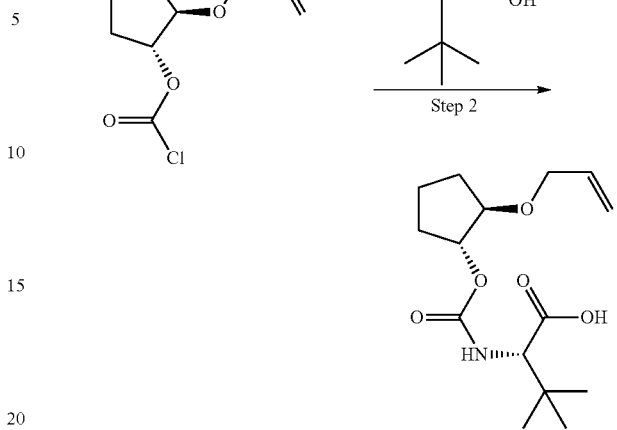

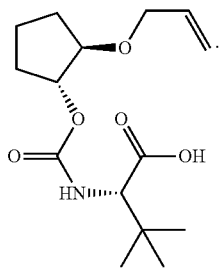 [SMILES: C=CCO[C@@H]1CCC[C@H]1OC(=O)N[C@H](C(=O)O)C(C)(C)C]

wherein Step 1 of the reaction takes place in a third solvent in the presence of a second base; and Step 2 of the reaction takes place in a fourth solvent in the presence of a third base, thereby forming a third product mixture comprising In certain such embodiments, triphosgene can be replaced with phosgene gas, carbonyl diimidazole, or another doubly activated analog of carbonic acid.

In certain such embodiments, the acid of the t-butyl glycine can be esterified (e.g., as a lower alkyl ester) during the carbamation, and subsequently deprotected under suitable deesterifying conditions (e.g., acid for t-butyl esters, acid or base for methyl/ethyl esters, and fluoride for 2-trimethylsilyl ethyl esters), with or without isolation or purification of the intermediate carbamate-ester, to reveal the carboxylic acid.

In certain embodiments, the invention relates to any one of the methods described herein including reaction scheme K, wherein the third solvent is DMA, toluene, dichloromethane, THF, acetone, heptane, hexane, methyl tert-butyl ether, ethyl acetate, dioxane, DMF, acetonitrile, or DMSO or a mixture thereof, preferably toluene.

In certain embodiments, the invention relates to any one of the methods described herein including reaction scheme K, wherein the second base is pyridine, $Et_3N$, $(iPr)_2EtN$, 2,6-lutidine, 1,8-diazabicyclo[5.4.0]undec-7-ene (DBU), 4-dimethylaminopyridine (DMAP), or 2,6-di-tert-butylpyridine, preferably 2,6-lutidine.

In certain embodiments, the invention relates to any one of the methods described herein including reaction scheme K, wherein Step 1 of the reaction of scheme K takes place at a third temperature, such as about −10° C. to about 20° C., for example about −10° C., about −5° C., about 0° C., about 5° C., about 10° C., about 15° C., or about 20° C., preferably about −10° C. to about 10° C., most preferably about 0° C.

In certain embodiments, the invention relates to any one of the methods described herein including reaction scheme K, wherein Step 1 of the reaction of scheme K takes place over a third period of time, such as about 10 min to about 40 min, for example, about 10 min, about 15 min, about 20 min, about 25 min, about 30 min, about 35 min, or about 40 min, preferably about 15 min to about 25 min, most preferably about 25 min.

In certain embodiments, the invention relates to any one of the methods described herein including reaction scheme K, wherein the fourth solvent comprises DMA, water, toluene, dichloromethane, THF, acetone, heptane, methyl tert-butyl ether, ethyl acetate, dioxane, DMF, acetonitrile, or DMSO or a mixture thereof, preferably toluene or water.

In certain embodiments, the invention relates to any one of the methods described herein including reaction scheme K, wherein the third base is K$_2$HPO$_4$, K$_3$PO$_4$, or a mixture thereof, Na$_2$HPO$_4$, Na$_3$PO$_4$, KOH, NaOH, or LiOH or a mixture thereof, preferably NaOH.

In certain embodiments, the invention relates to any one of the methods described herein including reaction scheme K, wherein Step 2 of the reaction of scheme K takes place at a fourth temperature, such as from about 0° C. to about 40° C., for example, about 0° C., about 5° C., about 10° C., about 15° C., about 20° C., about 25° C., about 30° C., about 35° C., or about 40° C., preferably about 10° C. to about 30° C., most preferably about 20° C.

In certain embodiments, the invention relates to any one of the methods described herein including reaction scheme K, wherein Step 2 of the reaction of scheme K takes place over a fourth period of time, such as about 1 h to about 30 h, for example, about 1 h, about 5 h, about 10 h, about 15 h, about 20 h, about 25 h, or about 30 h, preferably about 10 h to about 20 h, most preferably about 16 h.

In certain embodiments, the invention relates to any one of the methods described herein, further comprising isolating

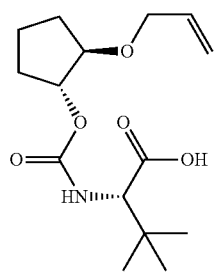 [SMILES: C=CCO[C@@H]1CCC[C@H]1OC(=O)N[C@H](C(=O)O)C(C)(C)C]

from the third product mixture, thereby obtaining substantially pure

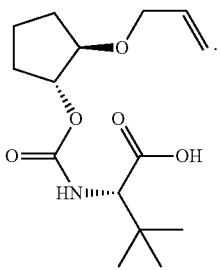

In certain embodiments, the invention relates to any one of the methods described herein, further comprising contacting

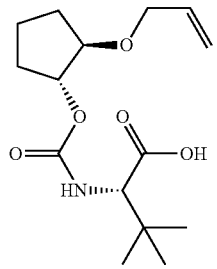

with a base, thereby forming a salt.

In certain embodiments, the invention relates to any one of the methods described herein, further comprising crystallizing

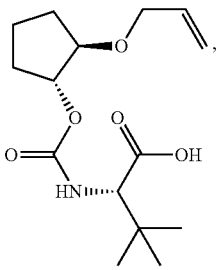 [SMILES: C=CCO[C@@H]1CCC[C@H]1OC(=O)N[C@H](C(=O)O)C(C)(C)C]

or a salt thereof, to obtain the compound in a crystalline form.

In certain embodiments, the invention relates to a method according to reaction scheme L:

Scheme L

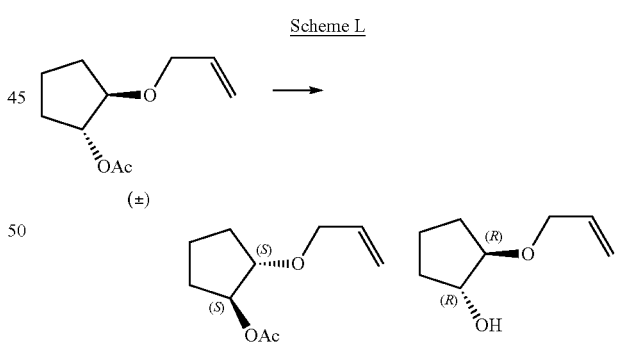

wherein the reaction takes place in a second solvent in the presence of a first enzyme, thereby forming a second product mixture comprising

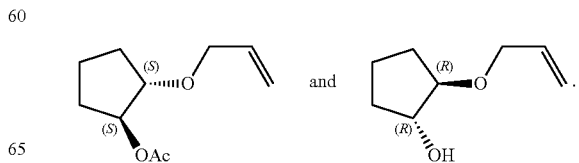

In certain embodiments, the invention relates to any one of the methods described herein including reaction scheme L, wherein the second solvent is an aqueous phosphate buffer.

In certain embodiments, the invention relates to any one of the methods described herein including reaction scheme L, wherein the second solvent is an aqueous buffer having pH about 6 to about 8, for example, about 6, about 6.5, about 7, about 7.5, or about 8, preferably about 7.

In certain embodiments, the invention relates to any one of the methods described herein including reaction scheme L, wherein the second solvent comprises $K_2HPO_4$, $KH_2PO_4$, $Na_2HPO_4$, $NaH_2PO_4$, or a mixture thereof, preferably $K_2HPO_4$ or $KH_2PO_4$ or a mixture thereof.

In certain embodiments, the invention relates to any one of the methods described herein including reaction scheme L, wherein the first enzyme is a lipase.

In certain embodiments, the invention relates to any one of the methods described herein including reaction scheme L, wherein the first enzyme is lipase from *Candida antartica*.

In certain embodiments, the invention relates to any one of the methods described herein including reaction scheme L, wherein the first enzyme is on a solid support.

In certain embodiments, the invention relates to any one of the methods described herein including reaction scheme L, wherein the first enzyme is lipase acrylic resin.

In certain embodiments, the invention relates to any one of the methods described herein including reaction scheme L, wherein the first enzyme is lipase acrylic resin from *Candida antartica*.

In certain embodiments, the invention relates to any one of the methods described herein including reaction scheme L, wherein the reaction of scheme L takes place at a second temperature, such as about 0° C. to about 40° C., for example, about 0° C., about 5° C., about 10° C., about 15° C., about 20° C., about 25° C., about 30° C., about 35° C., or about 40° C., preferably about 10° C. to about 30° C., most preferably about 20° C.

In certain embodiments, the invention relates to any one of the methods described herein including reaction scheme L, wherein the reaction of scheme L takes place over a second period of time, such as from about 1 h to about 50 h, for example, about 1 h, about 5 h, about 10 h, about 15 h, about 20 h, about 25 h, about 30 h, about 35 h, about 40 h, about 45 h, or about 50 h, preferably about 15 h to about 35 h, most preferably about 25 h.

In certain embodiments, the invention relates to a method according to reaction scheme M:

Scheme M

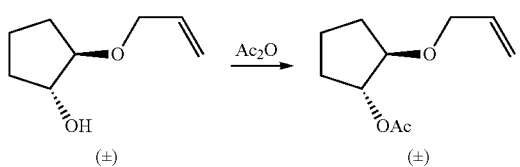

wherein the reaction takes place in a first solvent in the presence of a first base, thereby forming a first product mixture comprising

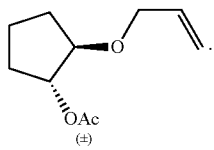

In certain embodiments, the invention relates to any one of the methods described herein including reaction scheme M, wherein the first solvent is toluene, dichloromethane, THF, acetone, heptane, hexane, methyl tert-butyl ether, ethyl acetate, dioxane, DMF, acetonitrile, or DMSO or a mixture thereof, preferably heptane.

In certain embodiments, the invention relates to any one of the methods described herein including reaction scheme M, wherein the first base is triethylamine, $(iPr)_2EtN$, or N-methylmorpholine, preferably $(iPr)_2EtN$.

In certain embodiments, the invention relates to any one of the methods described herein including reaction scheme M, wherein the first base is triethylamine, $(iPr)_2EtN$, $Et_2NH$, or $(iPr)_2NH$, preferably $(iPr)_2EtN$.

In certain embodiments, the invention relates to any one of the methods described herein including reaction scheme M, further comprising adding a first catalyst.

In certain embodiments, the invention relates to any one of the methods described herein including reaction scheme M, wherein the first catalyst is DMAP.

In certain embodiments, the invention relates to any one of the methods described herein including reaction scheme M, wherein the reaction of scheme M takes place at a first temperature, such as about −10° C. to about 20° C., for example about −10° C., about −5° C., about 0° C., about 5° C., about 10° C., about 15° C., or about 20° C., preferably about −10° C. to about 10° C., most preferably about 0° C.

In certain embodiments, the invention relates to any one of the methods described herein including reaction scheme M, wherein the reaction of scheme M takes place over a first period of time, such as about 5 h to about 15 h, for example about 5 h, about 6 h, about 7 h, about 8 h, about 9 h, about 10 h, about 11 h, about 12 h, about 13 h, about 14 h, about 15 h, preferably about 8 h to about 14 h, most preferably about 11 h.

In certain embodiments, the invention relates to any one of the methods described herein, further comprising isolating

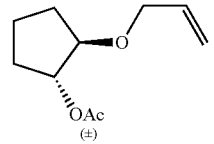

from the first product mixture, thereby obtaining substantially pure

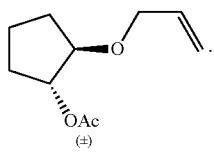

In certain embodiments, the invention relates to any one of the methods described herein, further comprising the steps outlined in any other method described herein.

In certain embodiments, the invention relates to the use of any one of the compounds described herein in the manufacture of a medicament.

Definitions of variables in the structures in the schemes herein are commensurate with those of corresponding positions in the formulae delineated herein.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers. Racemates, and Resolutions (John Wiley & Sons, 1981).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P.G.M. Wuts, Protective Groups in Organic Synthesis, 2d. Ed., John Wiley and Sons (1991): L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXEMPLIFICATION

The present invention is further illustrated by the following Examples, which should not be construed as limiting in any way. The Examples and discoveries described herein are representative. As such, the studies and results described in the Examples section herein may be used as a guideline.

Example 1—Synthesis of 70

The synthesis of compound 70 is shown in the scheme below. Allyl alcohol 25 is used in the opening of cyclopentenoxide 24 to give racemic alcohol 26. The allyl group serves as a protecting group in the synthesis of 70, so the epoxide opening could alternatively be conducted using other alcohols, such as benzyl alcohol, 4-methoxylbenzyl alcohol, etc. The free alcohol in 26 is acetylated to give 27 which is then subjected to enzymatic resolution to yield the (R,R) alcohol 13. The resolved alcohol 13 is then converted to the carbamate 6 which can be isolated as the DCHA salt. Carbamate 6 is also used in the ring-closing metathesis (RCM) route for the synthesis of 1. The allyl group in 6 is cleaved to yield the hydroxy carbamate 70 which can be isolated as the diisopropylammonium (DIPA) or DCHA salts.

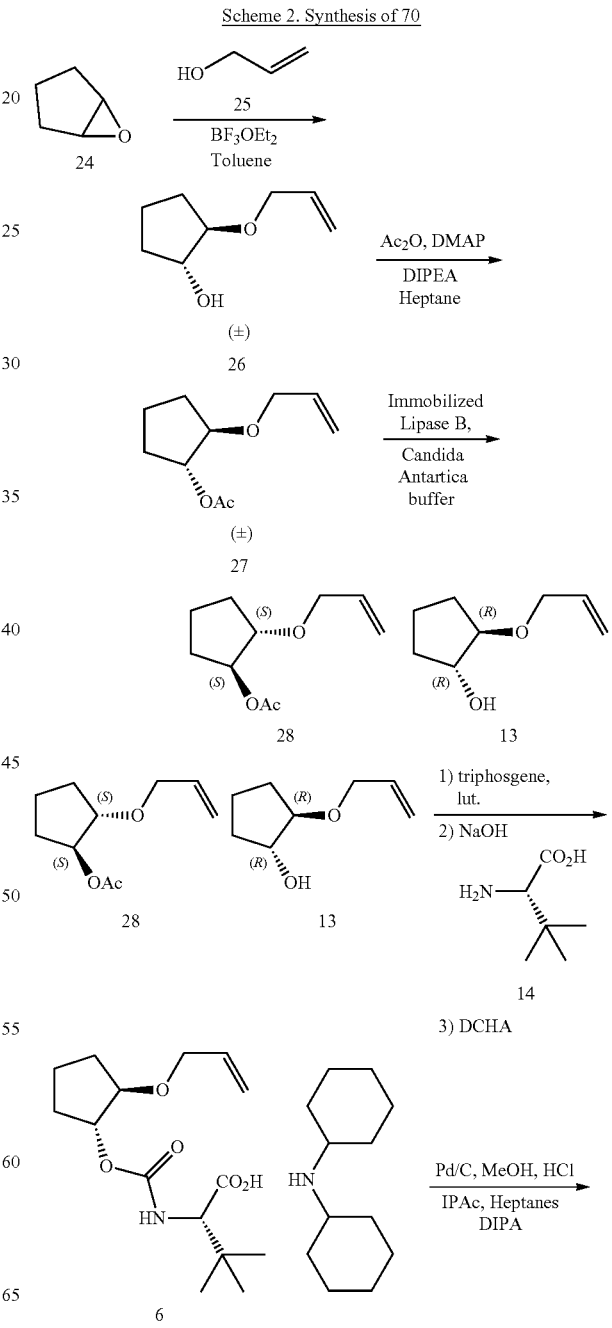

Scheme 2. Synthesis of 70

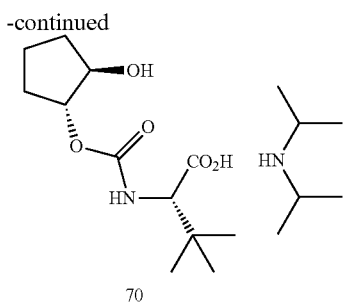

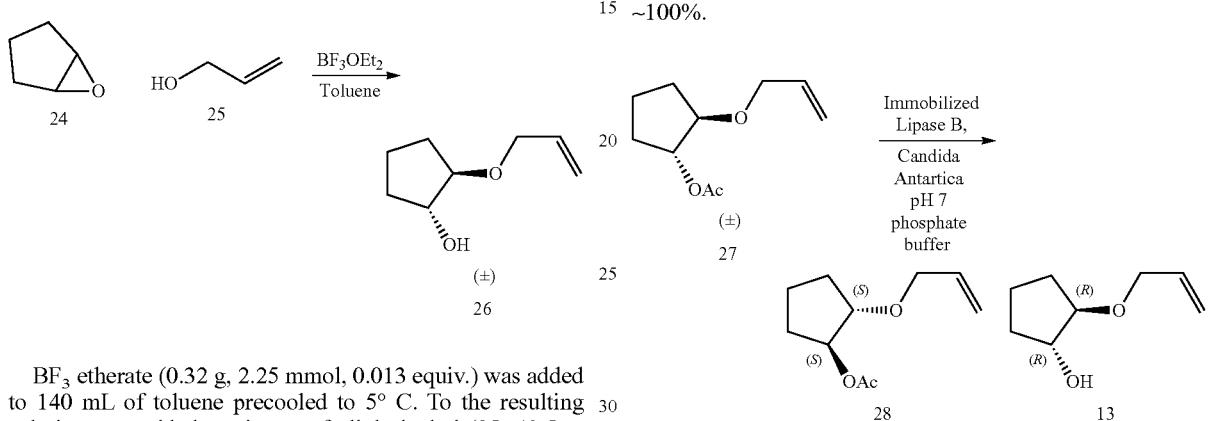

BF$_3$ etherate (0.32 g, 2.25 mmol, 0.013 equiv.) was added to 140 mL of toluene precooled to 5° C. To the resulting solution was added a mixture of allyl alcohol (25, 43.5 g, 750 mmol, 4.4 equiv.) and cyclopentene oxide (24, 14.5 g, 172 mmol) in toluene (40 mL) over 2 h at 0 to 5° C. The mixture was warmed to r.t. over approximately 3 h and mixed overnight. The mixture was cooled to 10° C. and quenched with 50 mL of 10% K$_2$CO$_3$ added in one portion. The mixture was stirred for 20 min at 10 to 15° C. and then the aqueous layer was separated. The toluene layer was washed again with 50 mL of 10% K$_2$CO$_3$. The toluene layer was concentrated by rotary evaporation to 26.6 g of oil which was assayed for 18.9 g (77% yield) of product 26. A 25 g sample was separated and distilled under vacuum. The main fraction (16.0 g, 69% adjusted yield) was collected at 62 to 67° C. and ~3 mm Hg.

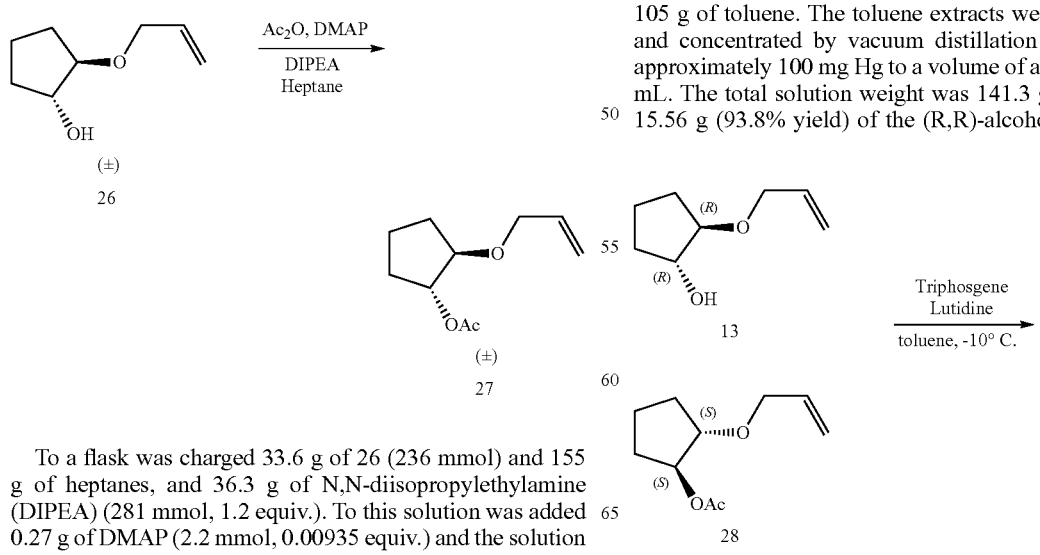

To a flask was charged 33.6 g of 26 (236 mmol) and 155 g of heptanes, and 36.3 g of N,N-diisopropylethylamine (DIPEA) (281 mmol, 1.2 equiv.). To this solution was added 0.27 g of DMAP (2.2 mmol, 0.00935 equiv.) and the solution was then cooled to −5° C. To this solution was then added 25.8 g of acetic anhydride (253 mmol, 1.07 equiv.) over approximately 30 minutes maintaining the temperature below 10° C. Another 16.2 g of heptanes was added and the reaction mixed at 0° C. After mixing for 11 h, the reaction was quenched with 397 g of 2.5% H$_3$PO$_4$ while maintaining the temperature at below 10° C. and mixture was then warmed to r.t. and the layers were mixed, settled and separated. The aqueous layer was re-extracted with 40 g of heptanes and this was combined with the first heptane extract. The heptane layer was then successively washed with 68 g of 20% brine, 81 g of 5% H$_3$PO$_4$, and then 2×116 g of 20% brine. The solution was concentrated until near completion and the final volume was 50 mL. A final sample was taken for analysis and showed 97.1% peak area purity with no starting material detected. The typical yield of 27 is ~100%.

To the acetate 27 (theory 43.5 g, 236 mmol) described above was charged a phosphate buffer solution at pH 7 prepared from 550 g of water, 25.0 g of K$_2$HPO$_4$ (144 mmol, 0.61 equiv.) and 12.0 g of KH$_2$PO$_4$ (88.2 mmol, 0.37 equiv.). To this mixture was charged 1.33 g of Lipase Acrylic Resin, *Candida Antartica* (Novozyme 435), (3 wt % relative to 27) and the mixture stirred at 20° C. After mixing for 25 h, 140 g of solid sodium chloride was added followed by 5 g of Hyflo and the mixture was stirred for 1 h. The mixture was filtered through a bed of Hyflo. The flask was rinsed with 200 g of toluene and the rinse was transferred through the filter setup collecting with the first filtrate. The mixture was stirred, settled and the aqueous layer separated. The aqueous layer was then re-extracted with 175 g of toluene, and then 105 g of toluene. The toluene extracts were then combined and concentrated by vacuum distillation at a pressure of approximately 100 mg Hg to a volume of approximately 150 mL. The total solution weight was 141.3 g and assayed for 15.56 g (93.8% yield) of the (R,R)-alcohol 13.

-continued

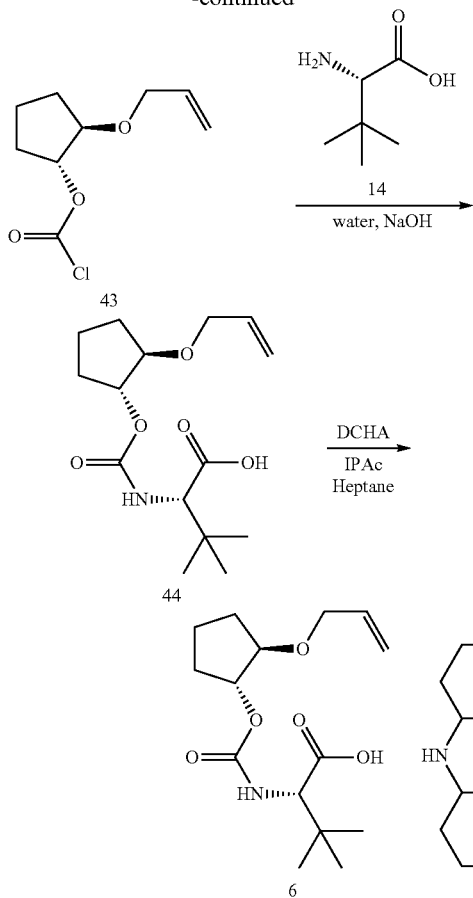

To a flask was charged triphosgene (6.45 g, 21.75 mmol, 0.4 equiv.), and a solution of alcohol 13 (70.66 g, containing 7.73 g of alcohol, 54.4 mmol, 1.0 equiv.) in toluene. The solution also contained 10.5 g of the (S,S)-acetate 28. To this mixture was added 106.6 g of toluene and the solution mixed and then cooled to −10° C. The 2,6-lutidine (8.85 g, 83 mmol, 1.52 equiv.), was added keeping the temperature below 0° C. After mixing for 25 min, formation of the chloroformate 43 was complete. A quench solution was prepared using 130 g of 5% NaH$_2$PO$_4$ and adjusted to pH 2 with phosphoric acid (3.13 g, 27.2 mmol) and the solution cooled to −2° C. The reaction mixture was transferred into the quench solution maintaining the temperature below 5° C. The layers were mixed at 0° C. and aqueous layer was separated and the toluene layer was washed with 150 g of cold 20% brine. The toluene solution of the chloroformate 43 was used directly in the next reaction.

To a flask was charged t-Leucine 14 (8.56 g, 65 mmol, 1.2 equiv.) and water (163 mL) and NaOH (4.77 g, 119 mmol, 2.2 equiv.) and the solution mixed and cooled to 0° C. To this solution mixing at high rpm was added the toluene solution of the chloroformate 43 over 5 minutes, rinsing with 10 g of toluene, and keeping the temperature below 5° C. The reaction temperature was held at 1° C. for 2 h, and then warmed to 20° C. After mixing for 16 h the mixing was stopped and the layers were allowed to settle. The aqueous layer containing the product was separated, and the toluene layer was washed with 10 g of water and the aqueous layers were combined. To the aqueous product solution was added 7.5 g of sodium chloride and mixed to dissolve the solids. The aqueous layer was then diluted with 31.7 g of IPAc and 141 g of heptanes. The pH of the aqueous layer was adjusted to 2.5 using phosphoric acid, and the layers were mixed settled and separated. The IPAc/heptane layer was then washed with 201 g of 20% brine. The IPAc/heptane layer was dried with magnesium sulfate and then filtered through a pad of Hyflo filter aid, and rinsed with 12.8 g of heptanes. The filtrate weight was 197 g, and assayed for 14.05 g (46.9 mmol) of acid 44.

To this solution was added 1.025 g (56.9 mmol, 1.2 equiv. relative to 44) of water and 8.575 g (47.3 mmol, 1.008 equiv. relative to 44) of dicyclohexylamine. After mixing at r.t. for 2 h, the product crystallized and a white slurry was obtained. The slurry was filtered and rinsed with 30 g of heptane. The solid was dried in a vacuum oven and the product assayed for an 83% yield of 6.

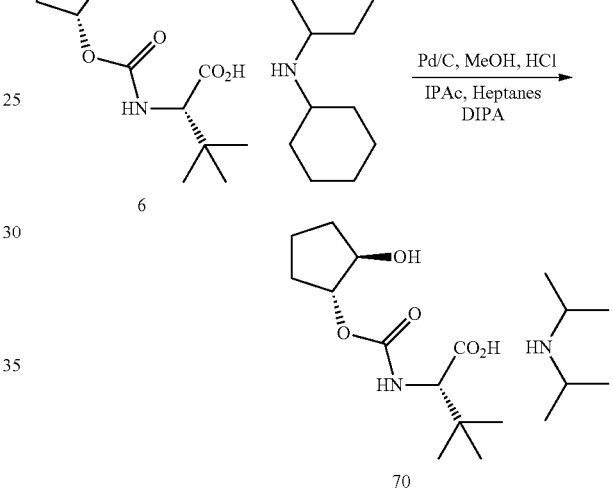

The compound 6 (10 g, 1.0 equiv) is dissolved in 2-methyltetrahydrofuran (82 g). A 20% HCl solution (15 g) is charged and the resulting thick white slurry is mixed, filtered, and the wet cake rinsed with 2-methyltetrahydrofuran (13 g). The aqueous layer in the filtrate is separated and the organic layer is washed with 10% HCl (20 g) and then water (20 g). The organic layer is concentrated to approximately 16 mL and then transferred to a nitrogen flushed flask containing 0.8 g of 5% Pd/C (dry basis). Then 26 g of methanol and 27 g of a 0.6% HCl solution are charged to the flask. The temperature of the reaction is adjusted to 60±5° C. and mixed for at least 8 h until completion. The reaction is cooled to r.t. and the slurry filtered through a bed of hyflo, rinsing with a solution of methanol:water. The filtrate is concentrated ~39 mL and sodium phosphate monobasic (0.5 g) is charged and mixed until dissolution. The solution is extracted twice with IPAc (61 g total) and the combined IPAc extracts are concentrated to a volume of ~23 mL. The solution is chased with IPAc to remove water, maintaining the volume at ~23 mL. The solution is heated to 45° C. and diisopropylamine (1.3 g) is charged while maintaining the temperature at 45° C. The crystallization is seeded and then diisopropylamine (0.5 g) is added followed by heptanes (38 g). The slurry is cooled to r.t., filtered, rinsing with IPAc/heptanes. The product 70 is dried under vacuum and the typical yield is 85-90%.

Example 2—Synthesis of 69

The synthesis of 69 shown in the scheme below begins with the addition of allyl alcohol 25 to trifluoropyruvate 60 and chlorination to yield 61. The zinc reduction of 61 yields the enol ether 62 which upon heating undergoes Claisen rearrangement to the keto ester 63. Condensation with diaminobenzene 18 yields the quinoxaline 64, which is subjected to chlorination to product 65. The displacement of the chloride with Boc-Hyp-OH 21 yields the acid 66 which can be isolated as the DIPA salt. The alkene in compound 66 is epoxidized to yield 67 which undergoes epoxide ring opening with strong base to yield the allylic alcohol 68. Removal of the Boc protecting group of 68 is accompanied with esterification to yield the ester 69. The methyl ester is shown but alternate esters can be formed, as well as alternate salts.

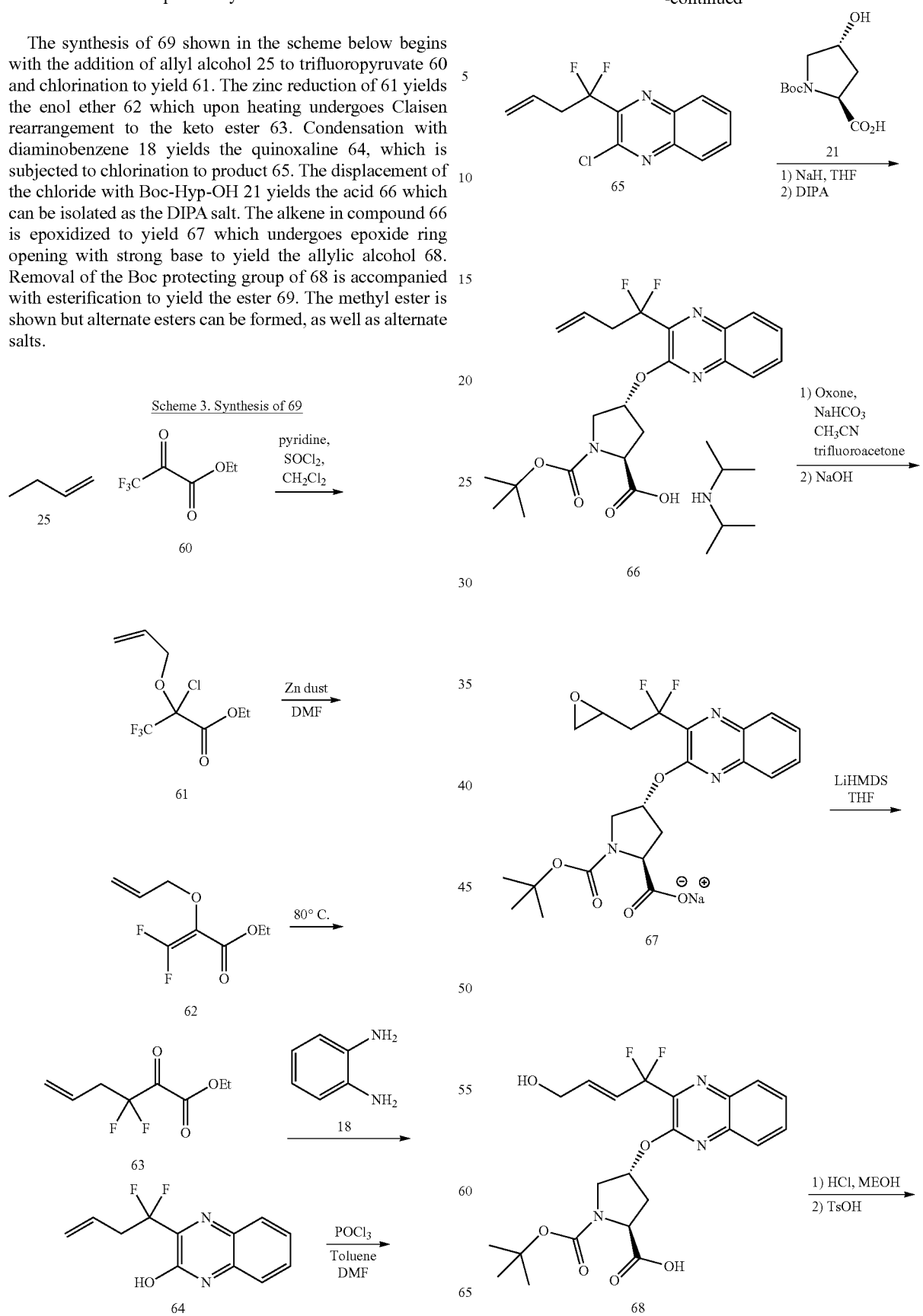

Scheme 3. Synthesis of 69

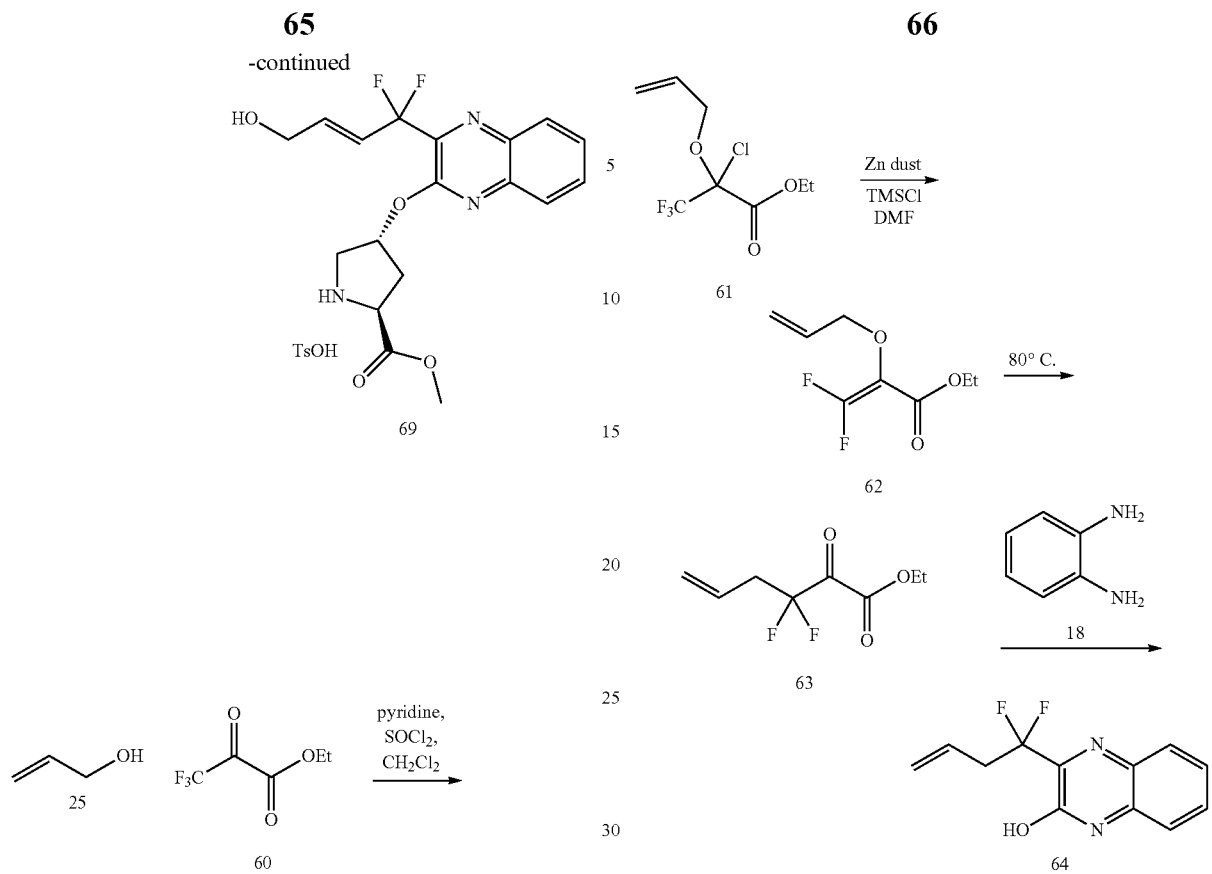

To a flask is charged dichloromethane (30 mL) followed by pyridine (1.30 equiv) and then by ethyl 3,3,3-trifluoro-2-oxopropanoate 60 (10.0 g, 1.0 equiv). The temperature of the solution is adjusted to 0° C. and allyl alcohol 25 (1.05 equiv) is charged while maintaining the temperature below 15° C. This solution is transferred to a cold solution of thionyl chloride (1.30 equiv.) in dichloromethane (30 mL) while maintaining the temperature below 15° C. A rinse of dichloromethane (10 mL) is used to complete the transfer. Upon reaction completion, the crude product solution is quenched into cold 20 wt % aqueous potassium phosphate tribasic (60 mL) maintaining the temperature below 25° C. The layers are mixed, settled and separated. The dichloromethane layer is washed with 5 wt % hydrochloric acid (50 mL) and then 20 wt % aqueous potassium phosphate tribasic (30 mL). The dichloromethane layer is dried with sodium sulfate rinsing the solids with dichloromethane. DMF (7 g) is charged and the solution concentrated to remove most of the dichloromethane, then diluted with DMF (7 g). The yield of 61 is typically 80-90% with >98 PA % purity as determined by gas chromatographic (GC) analysis.

The solution of 61 (10 g, 1.0 equiv) in DMF is charged to a flask and sparged with nitrogen and cooled to 0° C. To another flask is charged Zn dust (1.30 equiv) and DMF (20 mL) and the slurry is sparged with nitrogen. The Zn slurry is cooled to 15° C. and chlorotrimethylsilane (0.10 equiv) is added with vigorous mixing of the slurry for approximately 90 minutes. The zinc slurry is cooled to 0° C. and then transferred to the solution of 61 in portions while maintaining the temperature of below 15° C. Upon reaction completion, the reaction is filtered through celite, rinsing with DMF (10 mL) to wash the solids.

The DMF solution of 62 is heated to 80° C. to complete the Claisen rearrangement. Upon completion, the reaction is cooled to 0° C. A solution of benzene 1,2-diamine 18 (0.90 equiv) in DMF (7.5 mL) is sparged with nitrogen and then charged to the reaction maintaining a temperature below 25° C.; rinsing with DMF (2.5 mL) to complete the transfer. The temperature is adjusted to 20° C. and mixed until reaction completion. The temperature is adjusted to 40° C. and a 10 wt % aqueous ammonium chloride solution (~95 mL) is slowly charged to crystallize the product 64. The slurry is cooled and filtered, washing the wet cake aqueous DMF and then water. The wet cake is dried to remove residual water. The crude product 64 can be recrystallized from toluene or toluene/heptane. The typical yield of 64 is 65%.

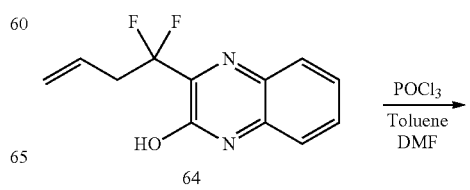

-continued

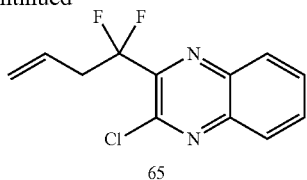

65

To a flask was charged 64 (22 g, 1.0 equiv.), toluene (132 mL) and DMF (7.15 g, 1.05 equiv.). Then POCl$_3$ (15.9 g, 1.1 equiv.) was added and the reaction mixture heated to 45° C. Upon reaction completion, the mixture was cooled to −5° C. and cold water (88 mL) was slowly added to quench the reaction. The mixture was warmed to r.t. and stirred for 1 hour. The lower aqueous layer was separated and the toluene layer was washed with water (110 mL), 10% aqueous K$_2$HPO$_4$ solution (110 g), and 25% brine solution (110 g). The toluene layer was dried with magnesium sulfate, filtered, rinsing with toluene, and the filtrate was concentrated. The crude product was solvent switched to isopropyl alcohol (IPA) and crystallized from IPA/water. The dry weight of 65 was 22.6 g for a 94% yield.

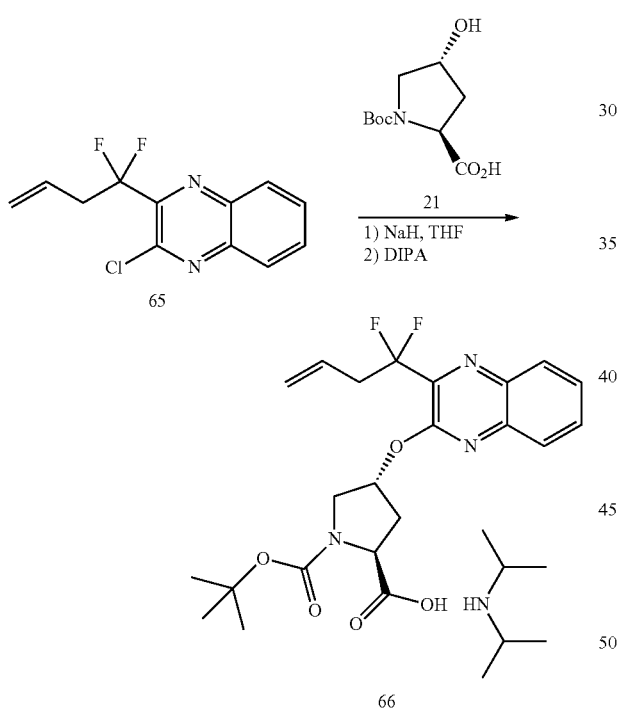

A solution of 65 (10 g, 1.0 equiv) in THF (19 g) is cooled below 10° C. To a flask is charged sodium hydride (60% in mineral oil, 2.2 equiv) and THF (34 g) and the mixture cooled to 15° C. A solution of Boc-L-Trans-Hydroxyproline 21 (1.10 equiv) in THF (30 g) is cooled to 15° C. and then slowly charged to the NaH slurry maintaining the temperature below 25° C. The mixture is stirred at 20° C. for approximately 20 minutes and is then cooled to less than 10° C. The solution of 65 is slowly charged to the slurry of 21 maintaining the temperature below 10° C. The reaction is adjusted to 20° C. and mixed until completion of the reaction. The reaction is cooled below 10° C., and cold water (63 g) is slowly charged to the reaction while maintaining the temperature below 25° C. The quenched reaction is adjusted to 22° C. and heptane (47 g) is charged, mixed, and then the product-containing aqueous layer is separated. MTBE (34 g) and heptane (16 g) are added to the product-containing aqueous layer, mixed, and then separated. MTBE (39 g) is added to the product containing aqueous layer and the pH lowered to approximately 2-3 using concentrated phosphoric acid (85%, approximately 6 g). The layers are separated and the product-containing organic layer is washed twice with water (2×20 g). The product solution is concentrated and the diisopropylamine salt 66 is crystallized from MTBE/heptane. The typical yield is 90%.

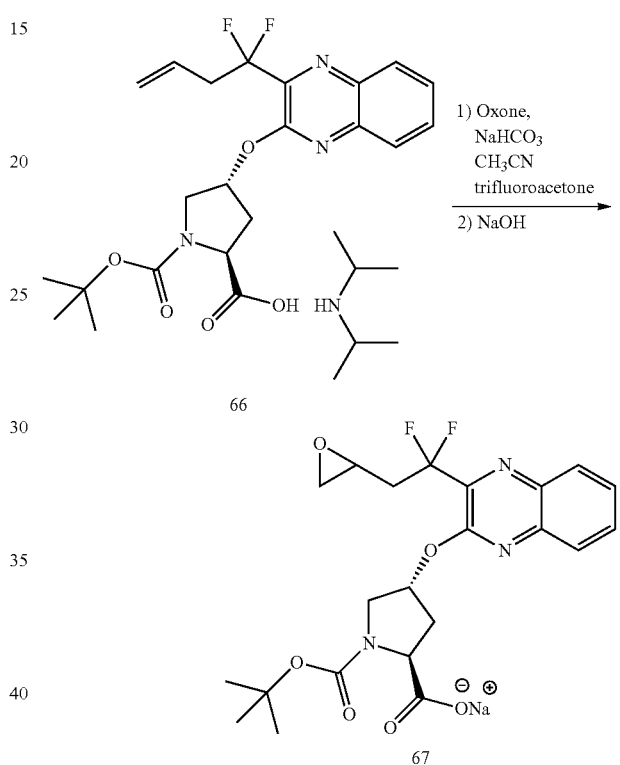

To a separatory funnel was added 66 (12.4 g, 22.3 mmol), and ethyl acetate (EtOAc or EA) (89.3 g). The mixture was washed sequentially with 1 M HCl (2×34 g) and then brine (39 g). The organic layer was concentrated to ~20 g and then chased with CH$_3$CN (3×24 g) and then diluted with CH$_3$CN to afford 33.6 g of a solution of the free acid of 66. To this solution was added water (110 mL), then NaHCO$_3$ (18.7 g) in portions at a rate to control the gas evolution. The resulting mixture was cooled in an ice bath and 1,1,1-trifluoroacetone (4.0 mL, 44.4 mmol, 2.0 equiv) was added. To the reaction mixture was added Oxone® (34.1 g, 55.5 mmol, 2.5 equiv) in approximately 3 g portions over 1.5 hours. After 3.25 hours, the reaction mixture was filtered and the solids were washed with cold EtOAc (90 g). To the combined filtrates were quenched with 25% sodium bisulfite, pH adjusted to 2.8. The layers were separated and the aqueous layer was back extracted twice with EtOAc (50 g, 30 g). The combined organic layers were then washed with brine (40 g). To the organic layer was added 50% NaOH (1.78 g). The resulting solution was chased with EtOAc (135 g). The resulting mixture was diluted with EtOAc (150 g), filtered and rinsed with EtOAc (14.7 g). The resulting solution was concentrated to 27 g and chased with 2-MeTHF (190 g) then diluted with THF (20 g) to afford 56.44 g of a 14.7 wt % solution of 67 in 2-MeTHF/THF (8.05 g, 74% yield). This solution was used directly in the next step.

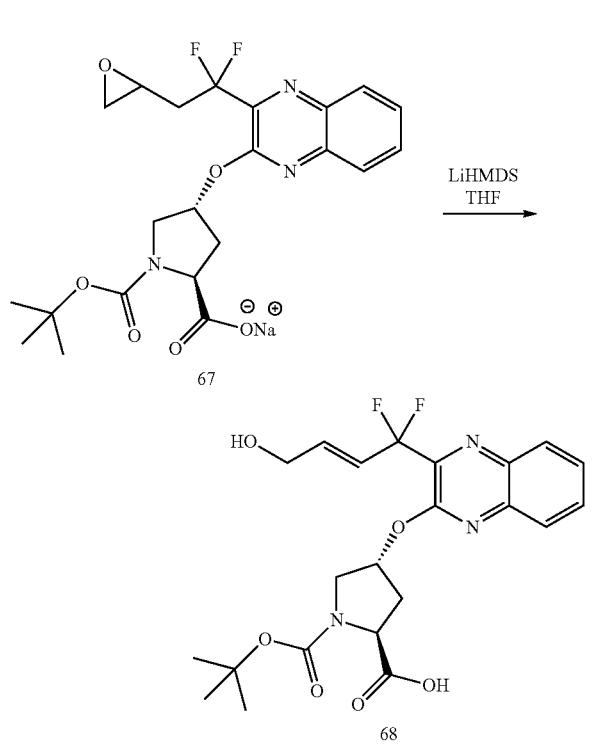

67

68

A solution of epoxide 67 (14.6 g, 1.0 eq) in THF (258 mL) was cooled to 0° C. A solution of 1 M lithium hexamethyldisilazide (LiHMDS) in THF (65.8 mL, 2.2 eq) was added maintaining temperature below 5° C. The reaction was mixed for 22 h until complete. The reaction was quenched with a 3.5% mono-potassium phosphate solution (117 g) followed by adjustment to pH 10.5 with phosphoric acid. The reaction was extracted with MTBE (143 mL) and the resulting aqueous product layer was extracted with MTBE (2×72 mL) to remove impurities, followed by adjustment to pH 5.5 with phosphoric acid. The product was extracted from the aqueous layer with MTBE (290 mL total), and the organic layer was concentrated to an oil. The crude product was purified by silica gel chromatography using dichloromethane-MeOH. The product fractions were concentrated and dissolved in MTBE to give an isolated assay yield of 9.4 g product (68%).

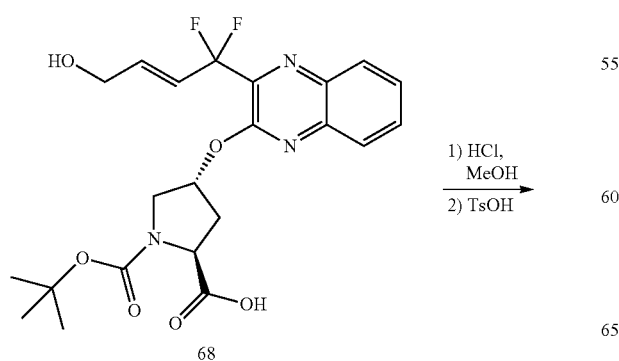

68

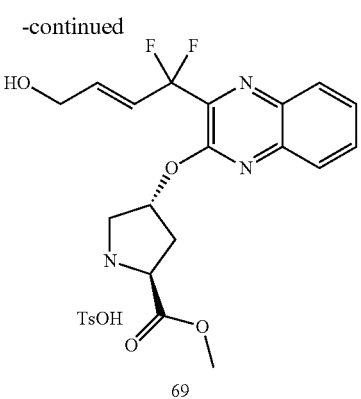

69

A solution of 68 (20.82 g, 1.0 eq) was concentrated and chased with MeOH to ~35 g and then dissolved in MeOH (84 mL). A MeOH solution of HCl (14.5% w/w, 90 g) was slowly added and the reaction was stirred at r.t. overnight. The reaction mixture was concentrated to remove most of the solvent and chased with MeOH (375 mL) to near completion. Toluene (46 mL) was added and the mixture concentrated to ~66 mL and the mixture diluted with 72 g of 2-MeTHF. This mixture was added to a cold 30 wt % $K_2HPO_4$ solution (200 g), using 20 mL of 2-MeTHF to complete the transfer. The mixture was diluted with toluene (100 g) and mixed for 30 min. The lower aqueous layer was separated and re-extracted twice with a mixture of toluene (100 g) and 2-MeTHF (20 g). The combined organic extracts were washed with brine (180 g), dried over $Na_2SO_4$, filtered, and concentrated to give 28.32 g of crude product as the free amine. The product was crystallized as the tosylate salt 69 from toluene and 2-MeTHF. The yield was 82%. Alternatively, the product can be crystallized as the HCl salt.

Example 3—Synthesis of 1 Via Etherification (Scheme 1)

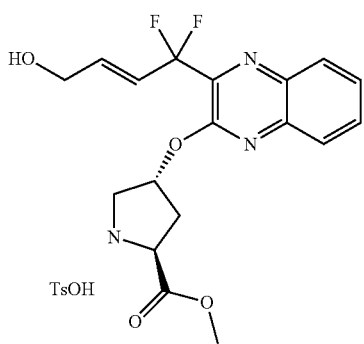

69

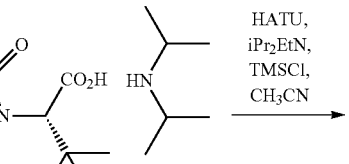

70

71

-continued

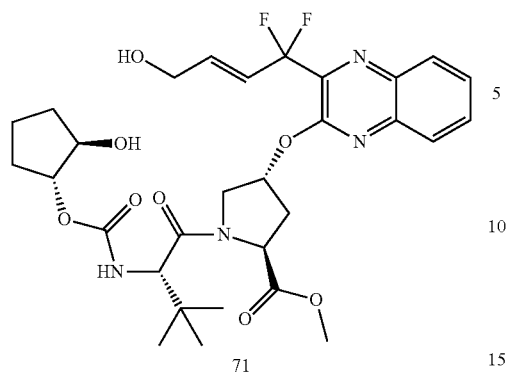
71

72

-continued

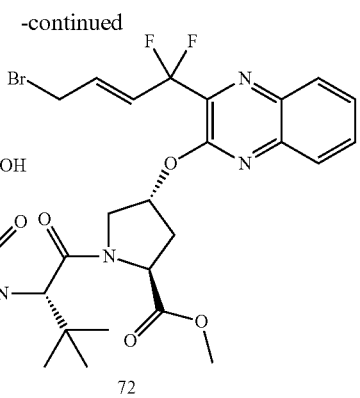
72

To a flask was charged 69 (1.9 g, 3.4 mmol, 1.0 equiv.) and CH₃CN (10 mL) followed by DIPEA (1.8 mL, 10. mmol, 3.0 equiv.) and the resulting solution stirred at r.t. for 10 min. and was then cooled to 0° C. Chlorotrimethylsilane (0.57 mL, 4.5 mmol, 1.3 equiv.) was added and the solution stirred at 0° C. To a separate flask was added 70 (1.73 g, 4.81 mmol, 1.44 equiv) and 1-[bis(dimethylamino)methylene]-1H-1,2,3-triazolo[4,5-b]pyridinium 3-oxid hexafluorophosphate (HATU) (1.83 g, 4.81 mmol, 1.4 equiv) and CH₃CN (12.5 mL). The resulting yellow solution was stirred at r.t. for 20 min. and was then added dropwise to the solution of 69 at 0° C., using a 1 mL CH₃CN rinse to complete the transfer. The reaction was warmed to 20° C. and stirred overnight. Toluene (15 mL) and 5 wt % formic acid (15 mL) were added to the reaction. The lower aqueous layer was separated and extracted with toluene (10 mL). The combined organic layers were washed with water (15 mL), saturated sodium bicarbonate solution (15 mL), and water (15 mL). The toluene solution of assayed for 2.15 g of 71 for a 100% yield.

A solution of 71 (25.0 g, 40.3 mmol) in toluene (12 g) was dissolved in dichloromethane (250 mL) and cooled to −5° C. A solution of triphenylphosphine (15.85 g, 60.4 mmol) in dichloromethane (210 mL) was cooled to 0° C., and then a solution of bromine (3.11 mL, 60.4 mmol) in dichloromethane (30 mL) added maintaining the temperature below 10° C. The Br₂/PPh₃ mixture was added to the solution of 71 maintaining the temperature below 0° C., rinsing with 10 mL dichloromethane. The reaction mixture was quenched into a cold 5 wt % aqueous sodium bicarbonate solution (365 g), rinsing with 10 mL dichloromethane. The mixture was stirred for 12 h at 0° C., then warmed to r.t. and mixed for 4 h. The layers were separated and the aqueous layer was re-extracted with 44 mL of dichloromethane. The combined dichloromethane extracts were concentrated and solvent switched to THF. The THF solution of 104.2 g assayed at 26.0 wt % of 72 for 98.4% yield.

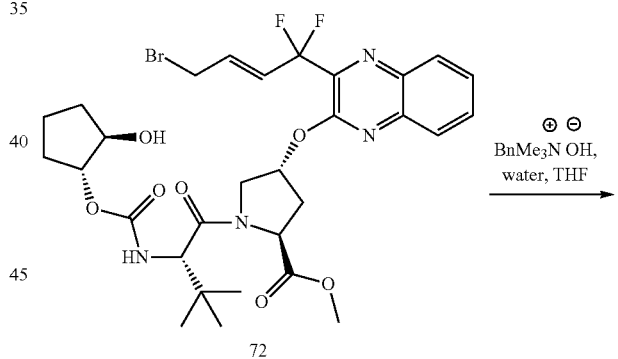
72

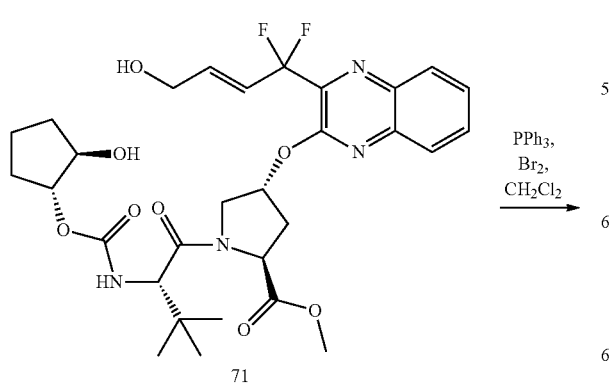
71

PPh₃, Br₂, CH₂Cl₂
→

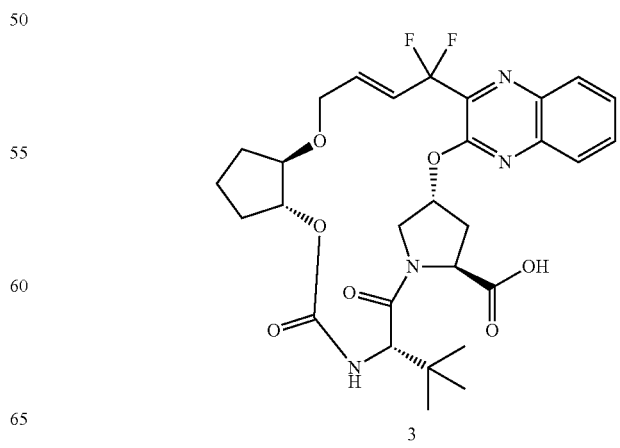
3

To a flask was added a 26.0 wt % solution 72 in THF (96 g, 36.6 mmol). To this was added THF (104 g) and H₂O (92.5 mL) then cooled to 1° C. Using an addition funnel, 40 wt % Triton-B (benzyltrimethylammonium hydroxide) (57.8 mL, 146 mmol) was added dropwise over 2 hours. The resulting solution was stirred overnight at 0° C. After 20 hours the reaction warmed to 7° C. and then 2-MeTHF (225 mL) and 6 M HCl (25 mL) were added and the resulting two layers were stirred for 10 min. This was transferred to a separatory funnel, the lower aqueous layer was removed and the upper organic layer was washed with 10% NaCl (112.5 mL). The organic layer was concentrated to 107 g and transferred to a separatory funnel with toluene (175 mL). To this was added 1% KOH (275 mL). The lower product aqueous layer was removed and the upper organic layer was washed with 1% KOH (100 mL). The two KOH product layers were combined and washed with toluene (2×125 mL). To the aqueous layer was added 2-MeTHF (225 mL) and 6 M HCl (12.5 mL). The layers were mixed and separated. The upper organic layer was washed with 5% NaCl (75 mL). This afforded 181.7 g of a solution containing 9.7 wt % of 3 for an 81.5% yield. An aliquot of the solution (36.2 g, 3.51 g net 3) was crystallized from MeOH/water/2-MeTHF to afford 4.08 g of a light brown solid. This solid was reslurried in heated toluene (40 mL) to afford 3.55 g of an off-white solid. This solid was recrystallized from 2-MeTHF/heptane to afford 3.21 g of a white solid, 88.6 wt %, for an 81.3% crystallization yield.

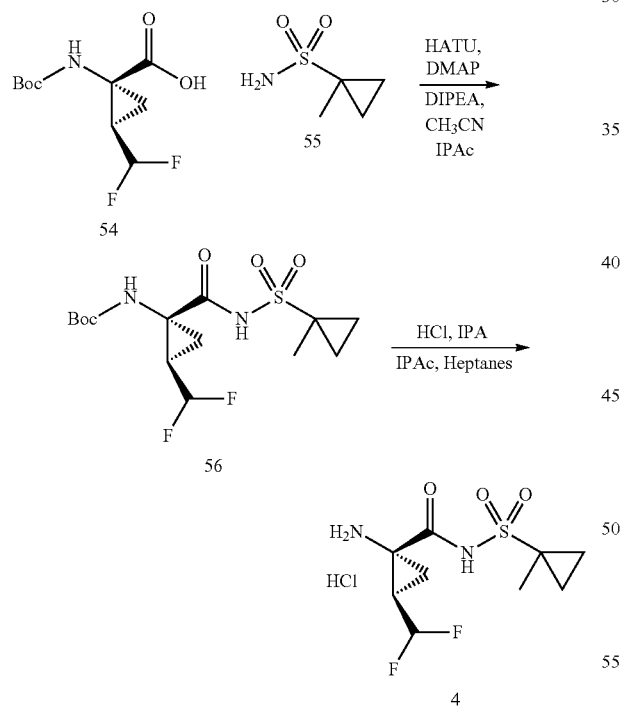

The acid 54 (10.0 g, 39.8 mmol, 1.0 equiv.), 1-methyl-cyclopropane-1-sulfonamide 55 (6.49 g, 48.0 mmol, 1.20 equiv), and HATU (17.86 g, 47.0 mmol, 1.18 equiv) were charged to a 250 ml flask followed by 120 mL of acetonitrile. Then 2,6-lutidine (5.5 mL, 51.5 mmol, 1.29 equiv.) was added dropwise maintaining an internal temperature below 25° C. The solution was stirred for 30 minutes and then cooled to 10° C. DMAP (19.45 g, 159.2 mmol, 4.0 equiv) was added in several portions over 6 minutes maintaining an internal temperature below 15° C. The resulting slurry was stirred overnight at 20° C. The reaction was filtered and the solids were washed with 30 mL of IPAc. IPAc (76 mL) was added to the filtrate and the solution washed with 20 wt % phosphoric acid (3×80 mL), 2 wt % phosphoric acid (1×80 mL), and water (5×80 mL). The IPAc solution of 56 was used directly in the next reaction.

The IPAc solution was concentrated under vacuum to an approximate volume of 114 mL, and chased with IPAc (2×60 mL) to an approximate volume of 114 mL. The slurry was cooled to 0° C. and anhydrous HCl in IPA (26.56 g at 20.56 wt %, 5.46 g of HCl, 150 mmol, 3.76 equiv.) was added. The slurry was warmed to 32° C. for 14 h. Upon completion of the reaction heptanes (98 mL) was added dropwise and the slurry cooled to 20° C. The solids were filtered, washed with heptanes (24 mL), and dried under vacuum to give 8.9 g of compound 4 (two step yield of 70%).

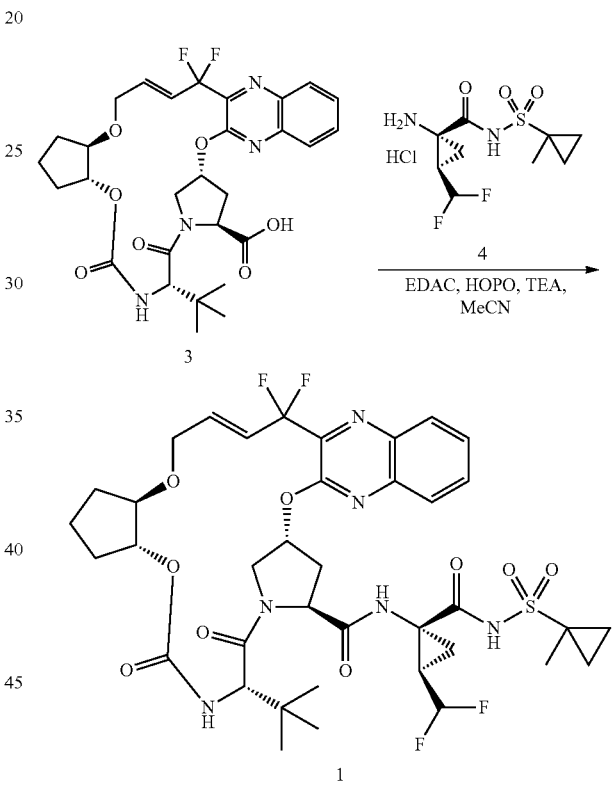

To a flask was charged acid 3 (45 g, 76 mmol), 2-Hydroxypyridine N-oxide (11.47 g, 103 mmol), and 1-ethyl-3-(3-dimethylaminopropyl)carbodiimide (EDAC) (19.05 g, 99 mmol) followed by MeCN (180 mL) and the mixture stirred at 22° C. until all the solids had dissolved. Into another flask was charged sulfonamide 4 (25.6 g, 84 mmol), followed by MeCN (180 mL) and triethylamine (17.0 g, 168 mmol) and the mixture stirred at 22° C. The activated acid solution from the first flask was charged to the sulfonamide solution over ~15 min at 22° C. The transfer was completed with a MeCN rinse of 45 mL. The reaction was mixed overnight at 22° C. The reaction was quenched water (45 mL) and then heated to 45° C. A solution of 210 g of water and acetic acid (11.5 mL) was prepared and then added to the reaction while maintaining the temperature at 45° C. Seed crystals were then charged and the mixture stirred until a slurry was formed. Water (338 g) was charged to the reaction over 1 h maintaining the temperature at 45° C. The slurry was cooled to r.t., filtered and the product washed with a mixture of MeCN/water. The crude product was recrystallized from MeOH/water for an overall yield of 94%.

Example 4—Syntheses of 23

Two alternate syntheses of the macrocycle 23 are shown in Scheme 4. The coupling of amine 80 with acid 81 yields the alkyne 82 which can be converted to macrocycle 23 by two methods. In one approach the Ru(Bipy)$_3$Cl$_2$ catalyzed hydro-alkylation of 82 yields macrocycle 23. In another approach the hydroboration of 82 yield the boronic acid 83 which can then undergo intramolecular Suzuki reaction to yield the macrocycle 23. These syntheses of 23 are based on the construction of two key structural fragments of the molecule, in particular compounds 80 and 81.

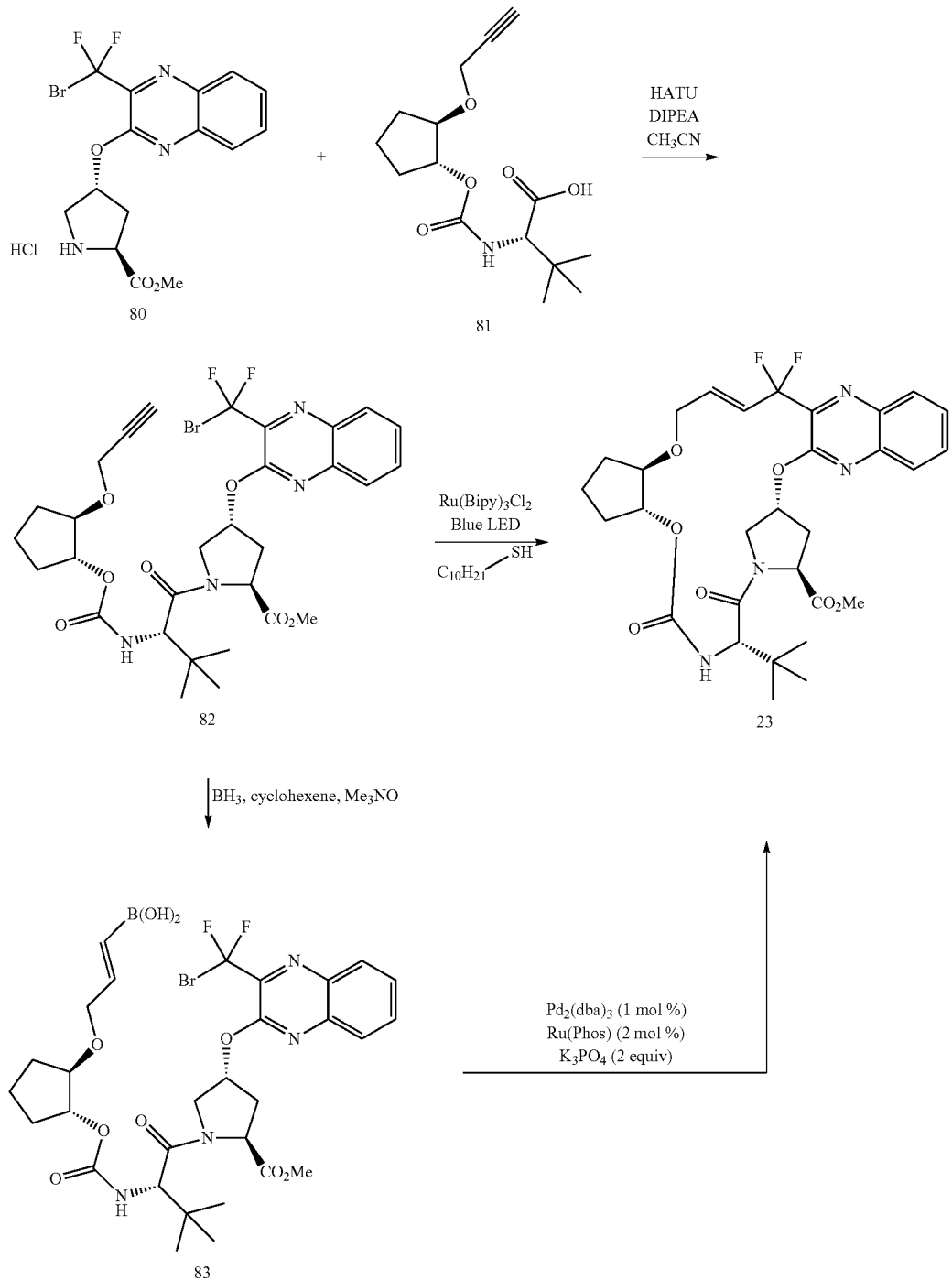

Scheme 4. Alternate Syntheses of 23

The synthesis of compound 81 is outlined in Scheme 5, and is very similar to the synthesis of compound 6. The main difference is the use of propargyl alcohol 84 instead of allyl alcohol for the opening of cyclopentenoxide 24. The subsequent steps follow the same sequence as in the synthesis of 6, however the final acid 81 is converted from the DCHA salt to the free acid for the coupling with amine 80. Detailed experimental examples are not included due to the similarity of the route to the synthesis of 6.

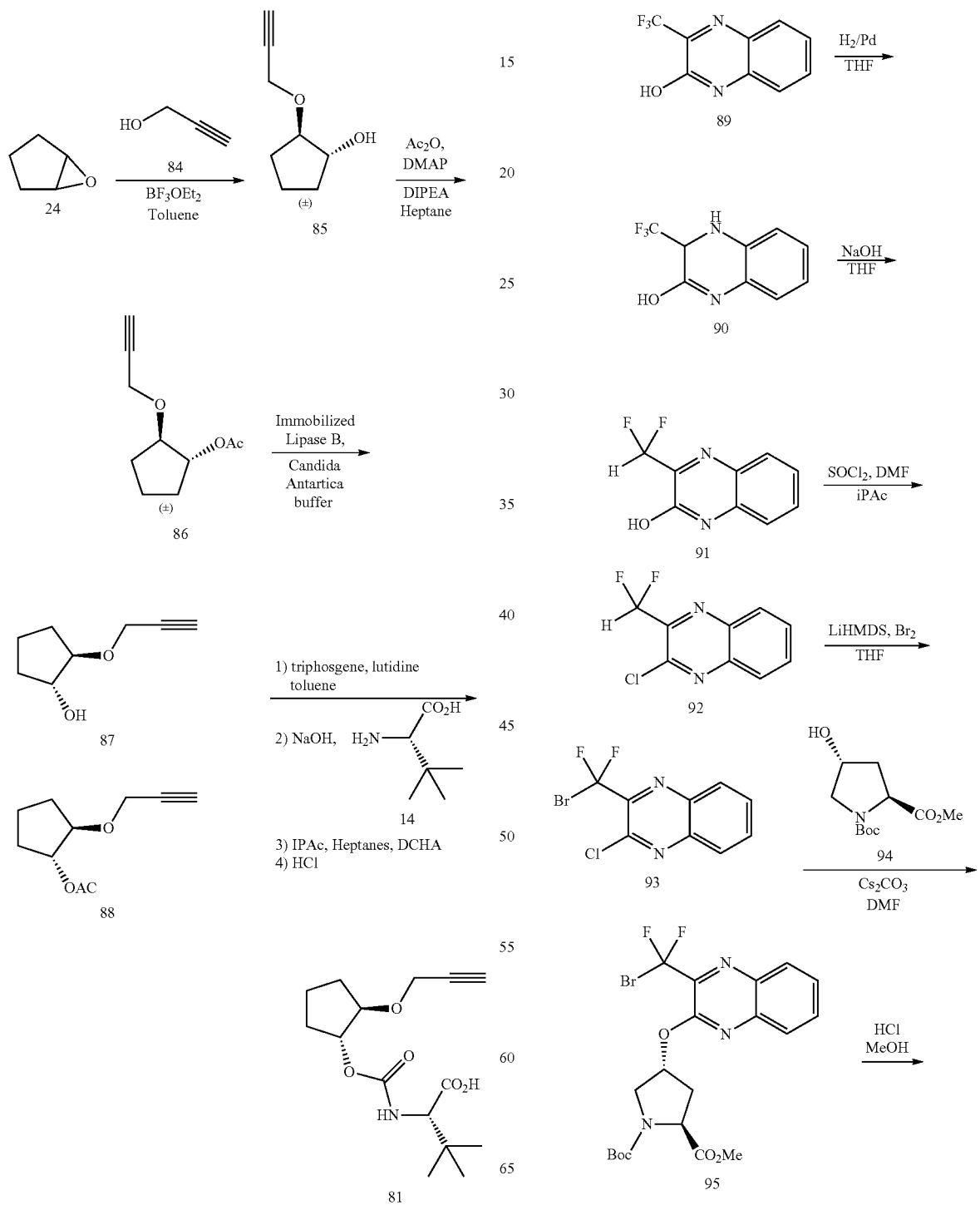

-continued

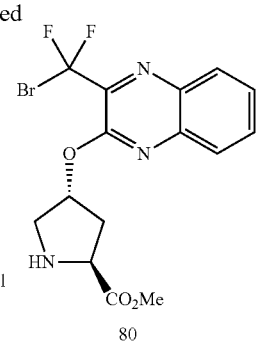

80

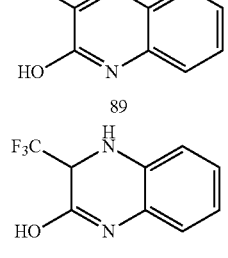

60 + 18

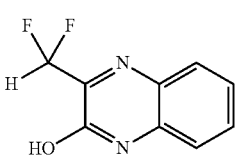

89

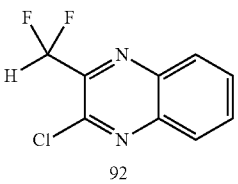

90

91

To a 2-gallon pressure reactor was charged o-phenylenediamine 18 (253.6 g, 2.345 mol, 1.0 equiv), THF (4.9 L). To this solution was added ethyl trifluoropyruvate 60 (406.5 g, 2.390 mol, 1.02 equiv) over 30 minutes while maintaining an internal temperature below 40° C. followed by THF (0.1 L). The reaction was heated 40-50° C. until the reaction was complete. The reaction solution was cooled to r.t. The reaction solution was sparged with $N_2$ and 21.2 g of 5% Pd/C was charged. The reactor was pressurized with 40 psi of $H_2$ and the reaction was heated to 50° C. until the reaction was complete. The reaction mixture was cooled to rt, the solids were removed by filtration under an $N_2$ atmosphere and washed with THF (0.5 L). To the filtrate was added 25% NaOH (1.12 kg). The reaction mixture was heated to 50° C. under an $N_2$ atmosphere until reaction was complete. After cooling the reaction mixture to 40° C., 3 M HCl (2.58 kg) was added. The lower layer was removed and the product containing upper layer was concentrated to approximately 3 L. To the product solution was added MeOH (0.25 L) and this was heated to 50° C. To this was charged $H_2O$ (3.75 L). The resulting mixture was cooled to 0° C., held at 0° C. for 2 hours. The solid was collected by vacuum filtration, washed with a cold solution of THF/$H_2O$ (0.3 L/0.5 L). The product was dried in the vacuum oven to afford 447 g (97%)

of 3-difluoromethylquinoxalin-2-ol 91 as a light yellow solid. $^1$H NMR (400 MHz, DMSO-$d_6$) δ 12.81 (s, 1H), 7.86 (dd, J=7.7, 1.6 Hz, 1H), 7.64 (td, J=7.7, 1.4 Hz, 1H), 7.42-7.30 (m, 2H), 7.04 (t, J=53.2 Hz, 1H).

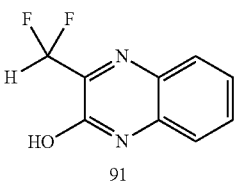 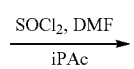

91

92

To a flask was charged 3-difluoromethylquinoxalin-2-ol 91 (38.0 g, 0.194 mol, 1.0 equiv.), isopropylacetate (300 mL) and DMF (1.8 mL). To this solution was charged thionyl chloride (19.0 mL, 0.260 mol, 1.34 equiv) over 5 minutes. The reaction was heated to 60° C. until the reaction was complete. The reaction was cooled to 0° C. and diluted with isopropyl acetate (380 mL). To the solution, $H_2O$ (228 mL) was added. The resulting mixture was warmed to rt and the lower layer was removed. The upper product layer was washed with 10% aqueous $KH_2PO_4$ (2×228 g) and 20% aqueous NaCl (249 g). The upper product layer was concentrated, chased with heptane (2×330 mL), heated to 50° C. then cooled to 10° C. The solid was collected by vacuum filtration, washed with heptane (80 mL) and dried in the vacuum oven to afford 37.0 g (89%) of 2-chloro-3-(difluoromethyl)quinoxaline 92. $^1$H NMR (400 MHz, CDCl$_3$) δ 8.24 (dd, J=8.1, 1.7 Hz, 1H), 8.12 (dd, J=8.1, 1.6 Hz, 1H), 8.01-7.85 (m, 2H), 7.05 (t, J=53.4 Hz, 1H).

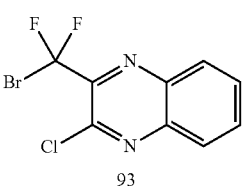

92

93

To a flask was charged 2-chloro-3-(difluoromethyl)quinoxaline 92 (35.0 g, 0.163 mol, 1.0 equiv) and THF (700 mL). The solution was cooled to 0° C. and bromine (16.8 mL, 0.326 mol, 2.0 equiv) was added. To the solution was charged 1.0 M LiHMDS in THF (490 mL, 0.490 mol, 3.0 equiv) over 55 min. The reaction was stirred at 0° C. until complete. To the reaction was charged 1.0 M aqueous citric acid (175 mL). The lower layer was removed and the upper product layer was washed with 10% aqueous sodium bisulfite (175 mL, 150 mL) and 20% aqueous sodium chloride (2×175 g). The organic layer was concentrated to an oil, chased with heptane (700 mL) then diluted with heptane (560 mL). The solution was washed with 10% aqueous sodium chloride (125 g). The upper product layer was filtered. This solution was concentrated to an oil and compound 93 was used directly in the next step.

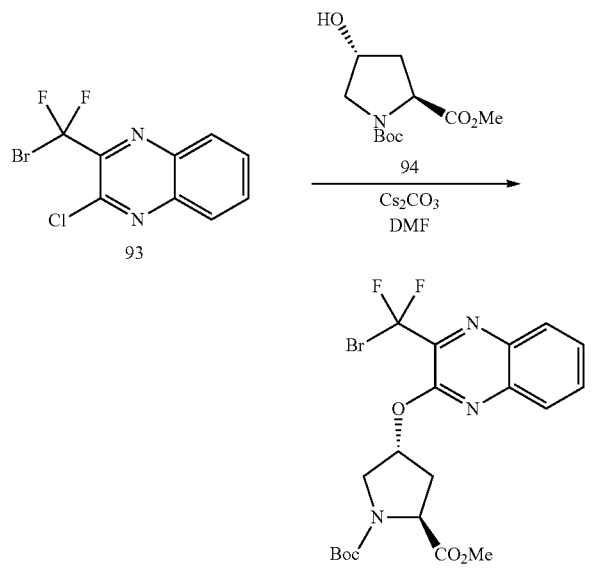

To a flask was charged Boc-Hyp-OMe 94 (46.8 g, 0.191 mol, 1.27 equiv) and cesium carbonate (140.0 g, 0.430 mol, 2.87 equiv). The 2-chloro-3-(bromodifluoromethyl)quinoxaline 93 (44.0 g, 0.150 mol, 1.0 equiv) was dissolved in DMF (200 mL), transferred into the flask, and rinsed into the flask with DMF (90 mL). The reaction was heated to 38° C. until complete. The reaction mixture was cooled to 20° C. and MTBE (460 mL) and H$_2$O (520 mL) were added. The layers were separated and the upper organic layer was washed with H$_2$O (230 mL) and 20% aqueous sodium chloride (230 g). To the upper organic layer was charged activated carbon (6.0 g). This mixture was stirred for 1 hour then filtered using MTBE (60 mL) as a wash. The filtrate was concentrated and chased with EtOH (220 mL). To the residue was added EtOH (350 mL) and H$_2$O (180 mL). The mixture was cooled to 0° C., filtered and washed with a cold EtOH/H$_2$O solution (120 mL/80 mL). The solid was dried in a vacuum oven to afford 62.2 g (83%) of compound 95.

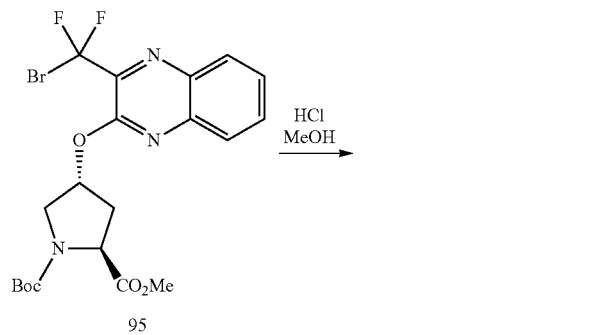

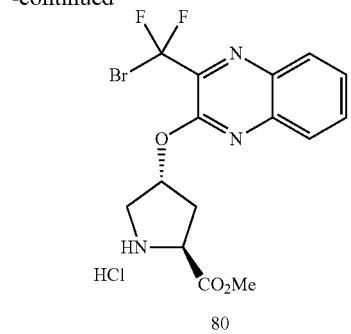

To a flask containing 95 (13.06 g, 26.0 mmol) was added MeOH (65 mL). This was stirred for 5 minutes, and then HCl, 4.0 M in dioxane (32.5 mL, 130 mmol) was added over 1 minute. The resulting yellow solution was stirred at r.t. under N$_2$. After 4.5 hours the solution was concentrated, chased with IPAc (50 mL), and the solid was slurried with MeOH (17 mL) and IPAc (40 mL). This mixture was heated to 50° C. for 20 min and then added IPAc (57 mL). The mixture was cooled in an ice bath. The solid was collected by filtration, washed with IPAc (40 mL) and dried in the vacuum oven to afford 10.63 g (93%) of compound 80 as an off-white solid.

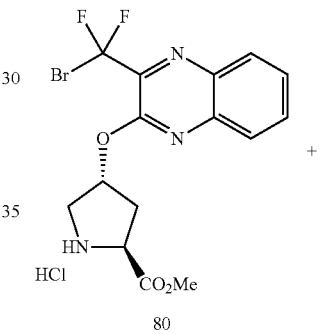

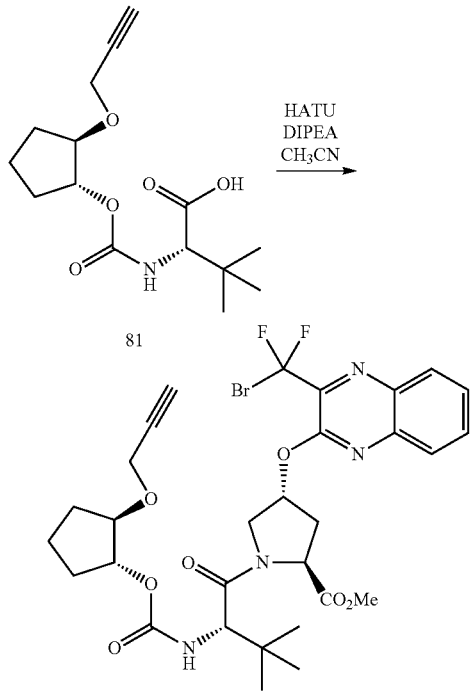

83

To a flask containing acid 81 (4.19 g, 11.27 mmol) and HATU (4.53 g, 11.92 mmol) was added $CH_3CN$ (30 mL). This solution was stirred at rt for 10 min. To another flask was charged amine 80 (4.85 g, 10.84 mmol), $CH_3CN$ (25 mL), and DIPEA (7.57 ml, 43.3 mmol). To this solution, the solution of acid 81 and HATU was added, rinsing with $CH_3CN$ (3 mL). After 3 hours the reaction was diluted with toluene (60 mL). The solution was concentrated to remove most of the $CH_3CN$ and then washed with 1 M HCl (50 mL), $H_2O$ (30 mL) and brine (25 mL). The organic layer was dried over $Na_2SO_4$, and filtered. The organic layer was concentrated and purified by silica gel chromatography to give a 90% yield of alkyne 82.

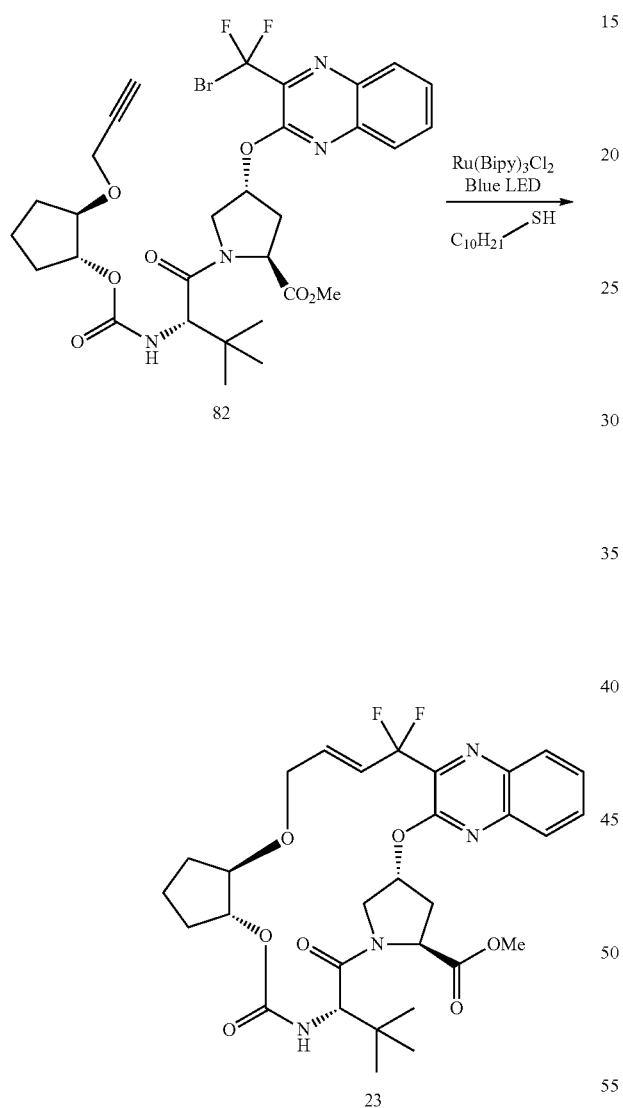

To a flask was added alkyne 82 (0.102 g, 0.138 mmol), $Ru(Bipy)_3Cl_2 \cdot 6H_2O$ (1.031 mg, 1.377 μmol, "Bipy" is 2,2'-bipyridine), and toluene (2.0 mL). After mixing until dissolution, DIPEA (0.048 mL, 0.275 mmol) and 1-dodecanethiol (0.049 ml, 0.207 mmol) were added. The solution was sparged under vacuum/$N_2$ three times. The stirred solution was exposed to blue-LED light at ~30° C. After 6 hours, 0.5 mL of $CH_3CN$ was added. After 23 h the reaction was complete and a modest yield of 23 and confirmed by HPLC analysis.

84

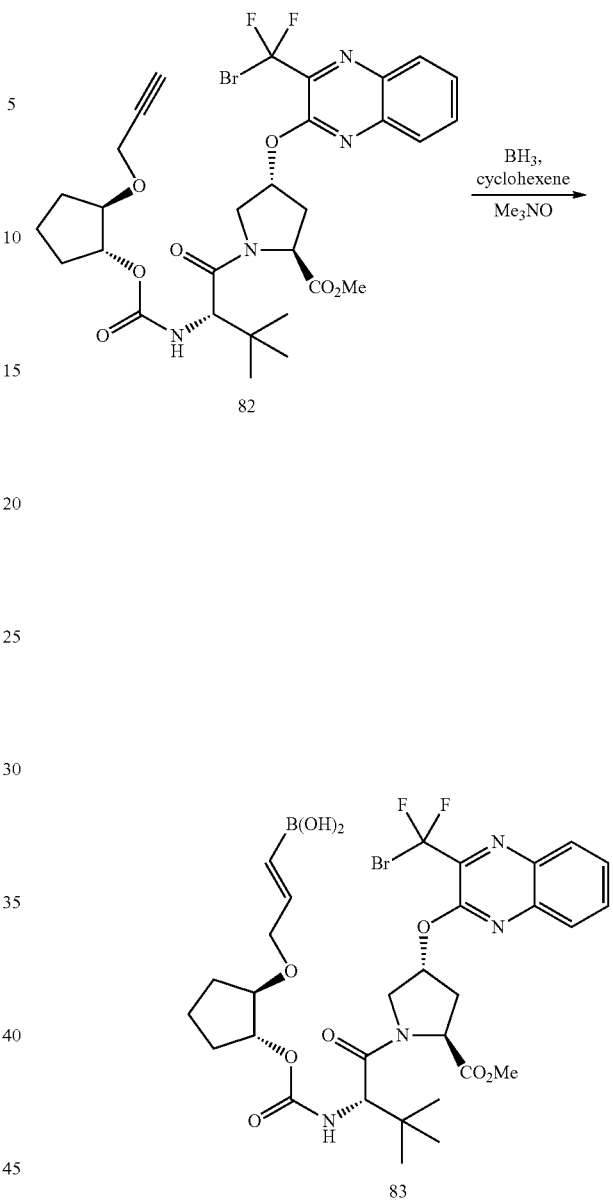

In a flask $Et_2O$ (1.7 mL) and cyclohexene (0.643 ml, 6.35 mmol) were added. This was cooled in an ice bath and 5.0 M $BH_3$ DMS (borane dimethyl sulfide) in $Et_2O$ (0.620 ml, 3.10 mmol) was added in one portion. This mixture was stirred in the ice bath for 3 hours under $N_2$. The solvent was removed by vacuum and the white solid was diluted with THF (1.4 mL). To this mixture cooled in the ice bath, a solution of alkyne 82 (1.10 g, 1.549 mmol) in THF (2.6 mL) was added then rinsed in with THF (1.0 mL). After 1.3 hours, the reaction was diluted with THF (5.0 mL) and trimethylamine oxide dihydrate (0.517 g, 4.65 mmol) was added. After 2.5 hours, water (5 mL) was added to the reaction mixture. This was stirred for 5 min and then MTBE (7 mL) and brine (2 mL) were added. The layers were separated and the organic layer was washed with brine. The organic solution assayed for 89% yield of 83 which could be further purified by silica gel chromatography.

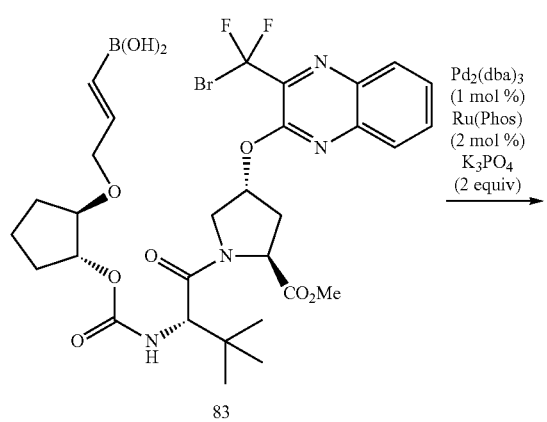

To a flask was charged K₃PO₄ (0.044 g, 0.206 mmol), Ru(Phos) (2.89 mg, 6.19 μmol, "Phos" is 2-dicyclohexylphosphino-2',6'-diisopropoxybiphenyl) and Pd₂(dba)₃ (1.416 mg, 1.547 μmol, "dba" is dibenzylideneacetone), and 1,2-dimethoxyethane (DME) (0.2 mL) and the resulting mixture was stirred at 50° C. for 20 min for catalyst activation. To this mixture was added a solution of 83 (75 mg, 0.103 mmol) in DME (0.2 mL) and water (0.02 mL). The reaction mixture was heated at 50° C. for 2.5 h and modest yield of 23 was confirmed by HPLC analysis.

Example 5—Synthesis of 54 Via Cyclopropanation

The cyclopropanation route for the synthesis of compound 54 is outlined in Scheme 7. The synthesis starts with the Knoevenagel condensation of diethylmalonate 74 with hemi-acetal 73 followed by cyclopropanation to give diester 76. The Knoevenagel condensation of malonate esters with the aldehyde hemiacetal 73 can be conducted with Lewis acids such as TiCl₄, Ti(OEt)₄, TiCl(OEt)₃, CeCl₃, Ce₂(SO₄)₃, MgCl₂, CaCl₂ and the like. Two methods were developed for the conversion of the racemic diester 76 into the enantiomerically pure acid 54. The first method involves simulated moving bed resolution of the racemic ester 78 to give the resolved (R,R) ester 79. The second method utilizes enzymatic resolution of 76 to prepare the resolved (R,R) acid 96. Both methods converge at the last step in the saponification of the resolved ester 79 to the acid 54.

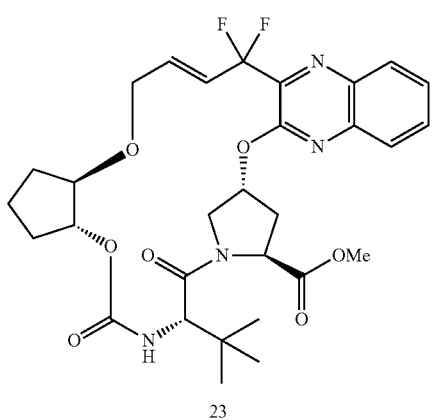

Scheme 7. Cyclopropanation Route for the Synthesis of 54

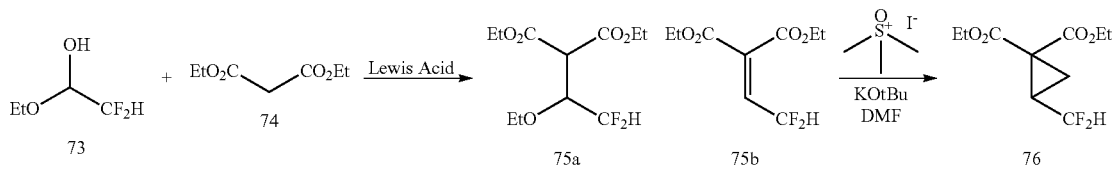

Simulated Moving Bed Resolution

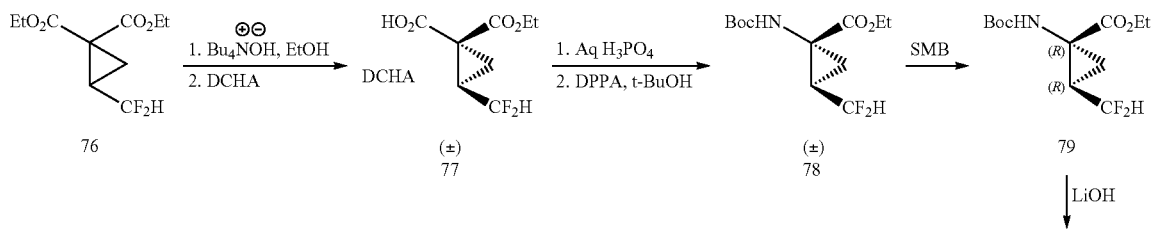

Enzymatic Resolution

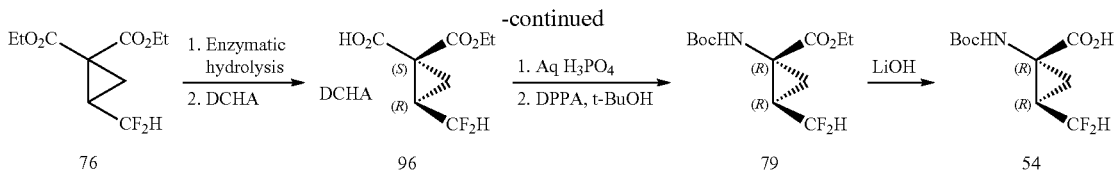

Knoevenagel Condensation with Catalytic CeCl$_3$/NaI

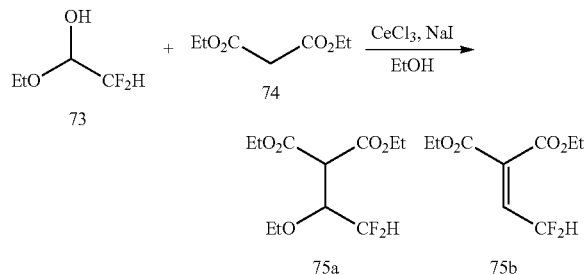

To a flask was charged CeCl$_3$ (1.54 g, 6.25 mmol, 0.05 equiv), NaI (0.94 g, 6.25 mmol, 0.05 equiv) and ethanol (80 mL) and the mixture was stirred with heating to 65° C. At reaction temperature of 65° C. a pre-mixed solution of diethyl malonate (20 g, 125 mmol) and 21.0 g difluoroacetaldehyde ethyl hemiacetal (90% w/w, 150 mmol, 1.2 equiv) was charged. The resulting mixture was stirred at 60-65° C. Upon completion the reaction was cooled to ambient temperature and inorganic solids were filtered off. The filtrate was concentrated under vacuum to near completion, diluted with dimethylformamide (DMF) (74 g), and concentrated under vacuum to remove the residual ethanol. The DMF solution is used directly in the next step as both 75a and 75b are converted to product in the cyclopropanation step.

Knoevenagel Condensation with Catalytic MgCl$_2$

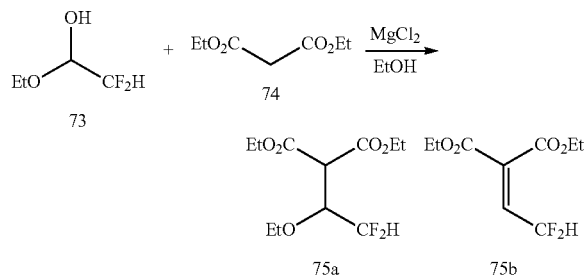

To a flask was charged MgCl$_2$ (1.189 g, 12.49) and EtOH (140 mL, 200 proof) and to this solution at ambient temperature, difluoroacetaldehyde ethyl hemiacetal (38.5 g, 90% w/w, 275 mmol, 1.1 equiv) was charged, followed by addition of diethyl malonate (40.0 g, 250 mmol). The resulting mixture was stirred at 60-65° C. Upon completion the reaction mixture was cooled to ambient temperature and concentrated under vacuum to remove most of the ethanol. The mixture was filtered to remove inorganic salts, DMF (74 g) was added to the filtrate, and concentrated under vacuum to remove the residual ethanol. The DMF solution is used directly in the next step.

Alternatively the reaction mixture can be worked up by concentration under vacuum to remove most of the ethanol, addition of methyl tert-butyl ether (MTBE) (300 mL) and washing with 150 mL 1 M HCl and then 150 mL brine. The MTBE solution is dried with MgSO$_4$, filtered, concentrated under vacuum, diluted with DMF, and concentrated under vacuum to remove the residual MTBE. The DMF solution is used directly in the next step.

Other Lewis acids catalysts which have been tested include CaCl$_2$ and Ce$_2$(SO$_4$)$_3$.

Knoevenagel Condensation with TiCl(OEt)$_3$

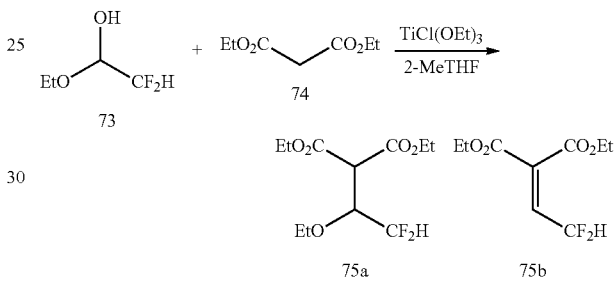

Titanium (IV) ethoxide (3.6 kg, 15.7 mol) and 2-MeTHF (18.5 kg) were charged to a flask. Acetyl chloride (1.2 kg, 15.7 mol) was added, rinsing with 2-MeTHF (2.0 kg). The mixture heated to reflux for 2 h and then cooled to 20° C. and held overnight. The mixture was cooled to −3° C. and diethyl malonate (1.2 kg, 7.5 mol) was added, rinsing with 2-MeTHF (1.7 kg). The difluoroacetaldehyde ethyl hemiacetal (1.0 kg, 7.5 mol) was added, rinsing with 2-MeTHF (1.7 kg). Then triethylamine (1.6 kg, 15.7 mol) was added and the mixture stirred at 0° C. for 4 h. The mixture was gradually heated to 50-57° C. and mixed for 2 h and then cooled to 20° C. and held overnight. The mixture was cooled to 3° C. and quenched with 1 M HCl (10.9 kg), mixed at 15° C., and the layers separated. The organic layer was wash with 1 M HCl (6.2 kg) and then 20% brine (6.8 kg). The product solution was dried with MgSO$_4$, filtered, rinsing with 2-MeTHF. The filtrate was concentrated under vacuum to near completion, DMF (4.7 L) was added, and the concentration continued to remove the 2-MeTHF. The DMF solution is used directly in the next reaction.

Cyclopropanation

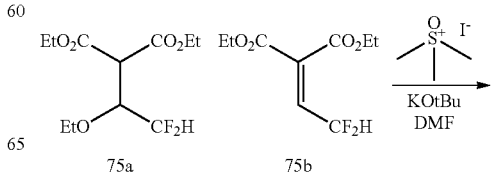

-continued

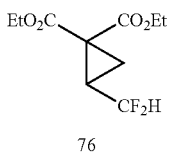

76

To a flask was charged potassium tert-butoxide (1.0 kg, 9.0 mol, 1.2 equiv), trimethylsulfoxonium iodide (2.0 kg, 9.0 mol, 1.2 equiv), and DMF (7.0 L). The mixture was stirred for 2 h, and then a solution of 75a and 75b (7.5 mol theoretical) mixture in DMF was added. The reaction was heated to 55° C. for 3.5 h and then cooled to 5° C. and mixed overnight. The reaction was quenched with a cold mixture of MTBE (14.4 L) and water (14.4 L), then mixed and warmed and the layers separated. The aqueous layer was re-extracted with MTBE (14.4 L) and the combined organic layers were washed with 20% brine (2×6.8 kg), and then with water (2×6 kg). The product solution was concentrated and solvent switched to EtOH and assayed for 80% yield of 76.
Chemical Hydrolysis

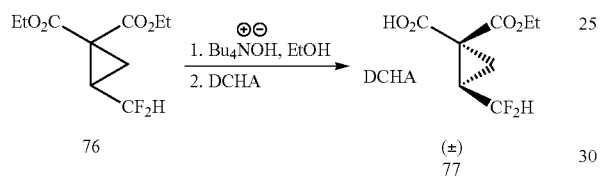

Tetrabutylammonium hydroxide (40 wt % aqueous, 4.3 kg) was added to the EtOH solution of compound 76 (7.5 mol theoretical from 74) and mixed at 20° C. Upon reaction completion, MTBE (14.4 L) was added and the mixture was cooled and 0.5 M HCl (14.4 L) was added. The mixture was warmed to 20° C.; the aqueous layer was separated and re-extracted with MTBE (6 L). The combined organic layers were washed with 20% brine solution (6.8 kg), and then water (6 L). The product was crystallized as the dicyclohexylamine salt from MTBE/heptanes. After filtration and drying a total of 1124 g of compound 77 was isolated (38% yield from 74).
Curtius Rearrangement

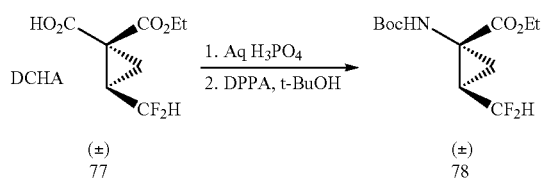 [SMILES: CCOC(=O)[C@@]1(C(=O)O)C[C@H]1C(F)F ; CCOC(=O)[C@@]1(NC(=O)OC(C)(C)C)C[C@H]1C(F)F]

To a flask was charged compound 77 dicyclohexylammonium (DCHA) salt (1.1 kg) and MTBE (11 L) and the mixture was washed twice with 7% phosphoric acid (11 L, 5.2 L), once with 20% brine (3.1 kg), and once with water (2.8 L). The organic layer was diluted with heptane (5.5 L) and concentrated under vacuum to a volume of ~4 L. Then tert-butanol (1.1 kg) and heptane (4 L) were added followed by triethylamine (437 g). The mixture was heated to reflux (76° C.) and then diphenylphosphorylazide (757 g) was added over 1.5 h. After heating for 10 h, the mixture was cooled to 20° C. and concentrated under vacuum to a volume of ~4 L. The mixture was diluted with MTBE (5.8 L) and successively washed with 5% aqueous citric acid (5.8 L), 8% aqueous NaHCO$_3$ (3.2 kg), 20% brine (3.4 kg), and water (3 L). The product solution in MTBE was solvent switched to acetonitrile (CH$_3$CN or MeCN or ACN) and the final solution assayed for 542 g of 78 for a 68% yield.
Simulated Moving Bed Resolution

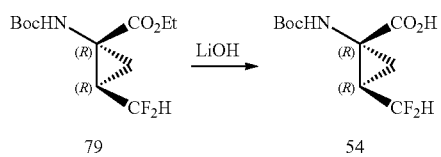

Racemic Boc amino acid ethyl ester 78 was subjected to simulated moving bed chromatography (SMB) to yield the (1R,2R) enantiomer 79.
Saponification

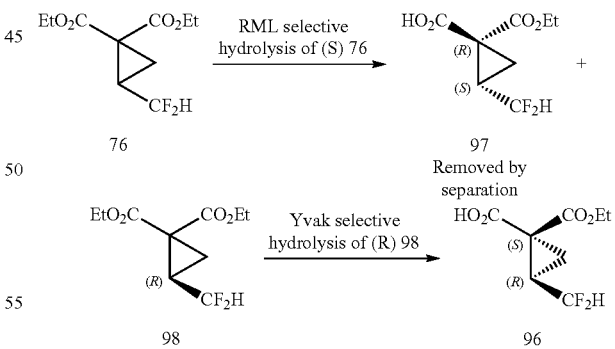

A solution of the Boc amino ethyl ester 79 (2 g, 7.16 mmol) in acetonitrile (10 mL) was treated with a solution of LiOH (193 mg, 7.88 mmol 1.1 equiv) in water (10 mL). The mixture was stirred at ambient temperature overnight. Upon reaction completion, 15% aqueous citric acid was added to achieve a pH of 4-4.5. The mixture was concentrated under vacuum to remove the acetonitrile and the resulting mixture was diluted with 5 mL water. The resulting slurry was mixed overnight at ambient temperature, filtered and washed with 4 mL water. The wet cake was dried in a vacuum oven to give an isolated yield of 80%.
Enzymatic Resolution The racemic diester 76 (1 g) was dissolved in 300 mL of 0.5 M sodium phosphate buffer, pH 7.0. To the reaction was added 15.3 mL of 3× dialyzed RML enzyme. The reaction was incubated at 30° C. and 125 revolutions per minute (rpm) for 96 hrs. Upon reaction completion, the desired unreacted (R) diester 98 was recovered from the aqueous reaction phase by extraction into MTBE (2×60 mL). The (S) acid 97 remained in the aqueous layer. The combined MTBE extracts were dried using magnesium sulfate, concentrated in vacuo and the recovered diester 98 was then dissolved in 0.5 M 150 mL sodium phosphate, pH 7.0 for use in the second resolution step.

YvaK clarified cell lysate (10 mL) was added to the solution of diester 98 in the sodium phosphate buffer. The reaction was incubated at 30° C. and 125 rpm for 96 hrs. Upon reaction completion, the pH was adjusted to 3 by addition of 5 N HCl. The acid product 96 was recovered from reaction aqueous phase by repeated extraction with MTBE (3×60 mL). The combined MTBE extracts were dried using magnesium sulfate and evaporated in vacuo to remove MTBE. The final recovered product (1S,2R) acid 96 in MTBE was filtered through Celite.

The acid 96 can be converted into the DCHA salt as described for compound 77. The acid 96, or its DCHA salt, can be converted into acid 54 by following the procedures described for the Curtius rearrangement (converting 77 to 78) and saponification (converting 79 to 54).

RML Dialysis Procedure: *Mucor miehei* lipase (RML, 6 mL) was placed in ~10 inches of 6-8 kDa molecular weight cut-off (MWCO) dialysis membrane and dialyzed for 4 hours in 2 liters of 0.1M sodium phosphate buffer, pH 7.0 at 4° C. and approx. 125 rpm. After 4 hours, the buffer was exchanged for 2 L of fresh 0.1M sodium phosphate buffer, pH 7.0 for an additional 24 hours. After 24 hours, the buffer was exchanged a third time for 2 L of fresh 0.1 M sodium phosphate buffer, pH 7.0 for an additional 24 hours. The final dialysis product results in ~18 mL of 3× dialyzed RML.

YvaK Clarified Cell Lysate-Enzyme Preparation Procedure: *Bacillus subtilis* esterase 'yvaK' (Gene ID-BSU33620) was inserted into pET21b vector at MCS between NdeI and BamHI restriction sites and transformed into BL21(DE3) competent cells. The yvaK esterase was subsequently expressed by growing the culture at 30° C., 225 rpm until an OD$_{600}$ of 0.5-0.8. Protein expression was induced with isopropyl β-D-1-thiogalactopyranoside (IPTG) to 0.1 mM and incubated for another for 18 hours. The resulting cell culture was pelleted by centrifugation at 3750 rpm, 30 min, 4° C. and stored at −80° C. until use. Cell pellets were resuspended in 0.5 M sodium phosphate buffer, pH 7.0 at a ratio of 1:10 resuspension buffer volume to expression culture volume. Resuspended culture was sonicated on ice three times for 30 s and centrifuged at 3750 rpm, 30 min, 4° C. The resulting supernatant was used as the clarified cell lysate solution.

Example 6—Synthesis of 54 Via Fluorination

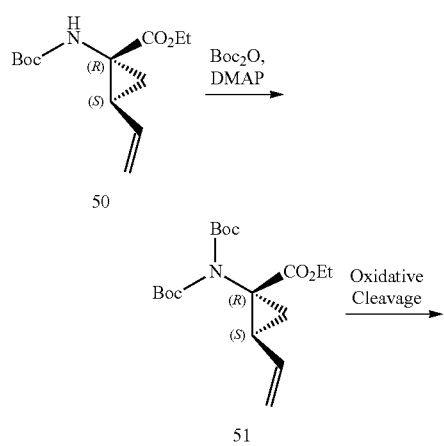

Scheme 8. Fluorination Route for the Synthesis of 54

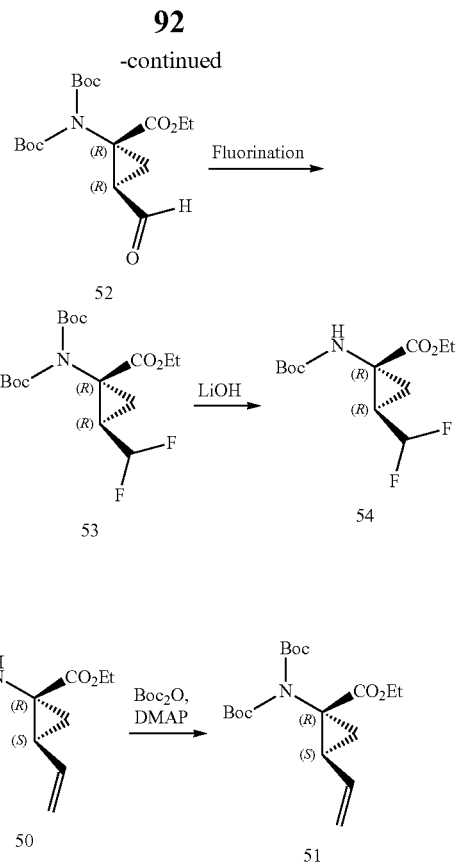

Into a round bottom flask was charged 50 (11.2 g, 43.9 mmol) dissolved in tetrahydrofuran (THF) (16 mL). To this solution was charged 4-dimethylaminopyridine (DMAP) (5.62 g, 46.1 mmol). To the resulting slurry was added a solution of Boc$_2$O (14.36 g, 66.0 mmol) in THF (10 mL) via a syringe, over 45 minutes at room temperature. The reaction mixture was quenched after 4.5 hours by addition of N,N-dimethylethylenediamine (3.87 g, 44 mmol) in one portion. The quenched reaction was mixed 30 minutes, then poured into heptanes (50 g) and 1 M H$_3$PO$_4$ (120 g). The layers were separated and the upper layer was washed with 23% brine (50 mL). The upper product-containing layer was concentrated in vacuo to afford 16.98 g of a light orange oil. Typical assay yield is 100%.

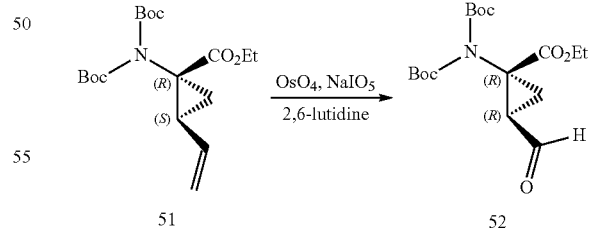

Into a round bottom flask was charged NaIO$_4$ (42.28 g, 198.0 mmol, 4.5 equiv.), water (90 g), 2,6-lutidine (2.14 g, 20 mmol) and OsO$_4$ (5.57 mL of a 4 wt % solution in water (0.88 mmol) and 1,4-dioxane (200 mL). The starting material 51 (15.59 g, 43.9 mmol) was dissolved in 1,4-dioxane (70 mL) and 2,6-lutidine (7.25 g, 67.8 mmol) and charged slowly over 4 hours while maintaining an internal temperature of <30° C., via an addition funnel. Additional NaIO$_4$ (4.7 g, 22.0 mmol, 0.5 equiv.) was charged in one portion to the reaction mixture (slurry). The reaction mixture was cooled and a solution of 10% aq. sodium thiosulfate (125 mL) was charged over 15 minutes. The precipitated $NaIO_3$ was filtered off and was washed with 1,4-dioxane (3×25 mL). The filtrate was extracted with heptane (200 mL). The layers were separated and the aqueous layer was re-extracted with a 4:1 heptane-MTBE solution (200 mL). The combined organic layers were washed sequentially with 7% aqueous $NaHCO_3$ solution (100 mL); 1 M $H_3PO_4$ (100 mL); an aqueous solution comprised of 20 mL of 10% aqueous $NaH_2PO_4$ solution and 80 mL 20% aqueous NaCl; 7% aq. $NaHCO_3$ solution (100 mL) and finally washed with 20% aqueous NaCl solution (50 mL). The organic layer was then concentrated in vacuo and chased with heptane (40 g), concentrating in vacuo to 15.8 g. The product was crystallized from heptane (16 g) at −25° C., filtered and washed twice with 5 mL of −20° C. heptane, and dried to constant weight to afford 11.78 g, for a 75% yield of 52. The aldehyde 52 can alternatively be crystallized from IPA/water with cooling to 0° C. for filtration.

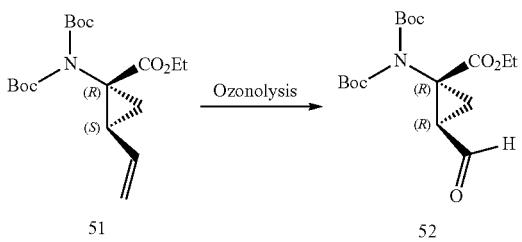

The starting material 51 (500 mg, 1.407 mmol, 1.0 equiv) was dissolved in 10 mL of dichloromethane and cooled in a −78° C. bath. Ozone was bubbled through the solution for approximately 5 min, until the solution became blue in color. The solution was mixed for 5 min and then purged with a stream of nitrogen until the color of the solution dissipated. Triphenylphosphine (406 mg, 1.547 mmol, 1.10 equiv) was added in one portion to the solution at −78° C. The bath was removed and the resulting solution was allowed to warm to rt, stirring overnight. The assay yield for the reaction was 93%.

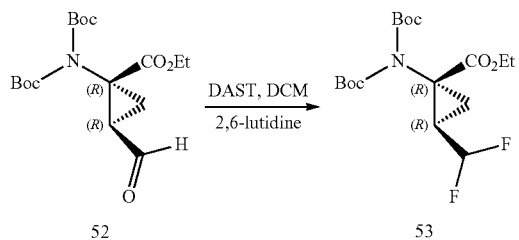

To a flask is charged 9.02 g of diethylaminosulfur trifluoride (DAST) (2.5 eq) and 45 g of dichloromethane. To this solution is added 0.48 g of 2,6-lutidine (0.2 eq) and the solution is cooled to 10° C. A solution of the aldehyde 52 (8.0 g, 1.0 eq) in 10 g of dichloromethane is added, rinsing with 2 g of dichloromethane. The reaction is mixed at room temperature (RT or rt or r.t., about 23° C.) for at least 12 h. The reaction mixture is transferred into a cold mixture of heptanes (40 g) and 18% aq. $K_2HPO_4$ (100 g), rinsing with dichloromethane. The lower (aqueous) layer is separated, and the upper layer is washed with mixture of 20% brine and 18% aq. $K_2HPO_4$. The upper product containing layer is concentrated to approximately 20 mL and then diluted with 3 g heptanes and 33 g of 5% aq. $KH_2PO_4$ solution. The biphasic mixture is stirred vigorously for at least 15 min during which time the starting aldehyde 52 is reformed. To the reaction is charged 8 g of 18% aq. $K_2HPO_4$ and 5 g of 33% aq. sodium bisulfite solution. The reaction is stirred until the aldehyde 52 is converted to the bisulfite complex, and then diluted with 24 g of heptanes and the layers are separated. The upper product containing layer is washed with 20% brine solution and then concentrated and used in the next step. The typical assay yield of 53 in the heptane solution is 45%.

The aqueous layer containing the starting aldehyde as the bisulfite complex is treated with 4.2 g of sodium carbonate. The aldehyde crystallizes out of the mixture and is cooled to 0° C. and filtered, washing with water. The typical recovery of 52 is 35%.

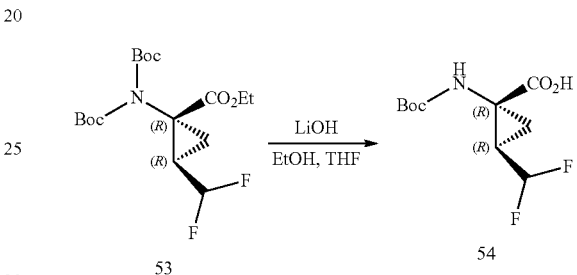

The starting material 53 as a solution in heptane is concentrated, chased with EtOH, and then dissolved in EtOH (6 mL/g of 53) and THF (6 mL/g of 53). The solution is heated to 50° C. and then a 5.5% aqueous solution of LiOH (5 eq) is added and the mixture stirred at 50° C. until the reaction is complete by high-performance liquid chromatographic (HPLC) analysis (approximately 10 h). The mixture is cooled to rt and formic acid (3.5 eq) is added and the mixture concentrated to approximately 7 mL/g. To this mixture is added isopropyl acetate (IPAc) (10 mL/g of 53) and formic acid (2.5 eq) to adjust the pH to ~4.5. The mixture is filtered, rinsing with IPAc and the aqueous layer is separated. The upper product containing layer is washed with water, and then brine. The IPAc solution is concentrated and the product crystallized from IPAc/heptanes. The yield of 54 is typically 80%.

Example 7—Overview of a Synthesis of 1 Via RCM

The RCM route for the synthesis of 1, shown in Scheme 9, utilizes a ring closing metathesis reaction as the key step in the synthesis of the macrocycle 3. The synthesis of 1 begins with the coupling of amine 5 with acid 6 to yield the diene 22. The diene 22 is subjected to ring closing metathesis to yield the macrocycle ester 23. The ester 23 is then saponified to the macrocycle acid 3. The final step is the same as the etherification route as the acid 3 is then coupled to amine 4 to yield 1. The synthesis is based on the construction of three key structural fragments of the molecule, in particular compounds 4, 5, and 6. The experimental examples for the syntheses of compounds 4 and 6 are described in the etherification route to 1. The experimental examples for the synthesis of compound 5 will be followed by the experimental examples for the final assembly of macrocycle acid 3.

Scheme 9. RCM Route for the Synthesis of 1
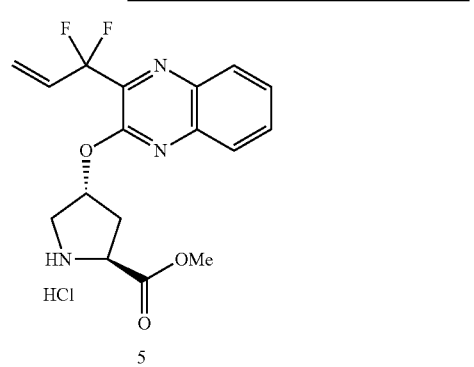
5
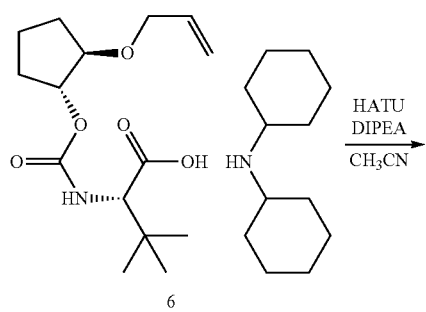
6
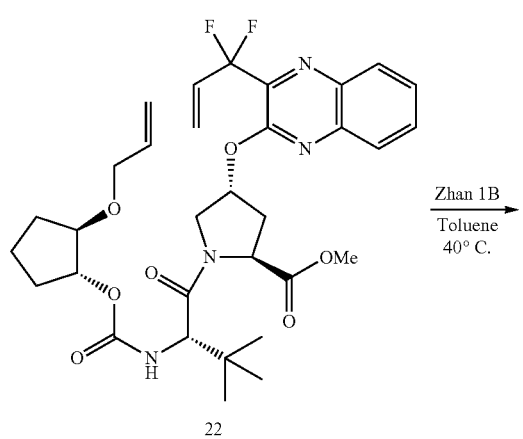
22
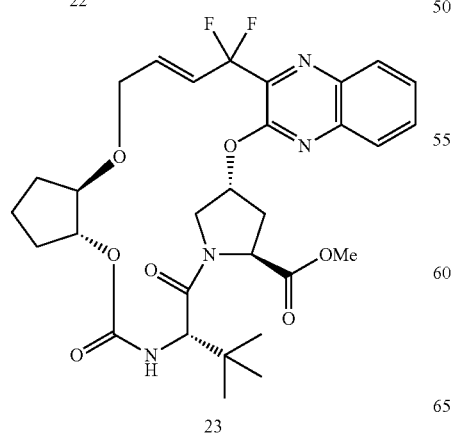
23
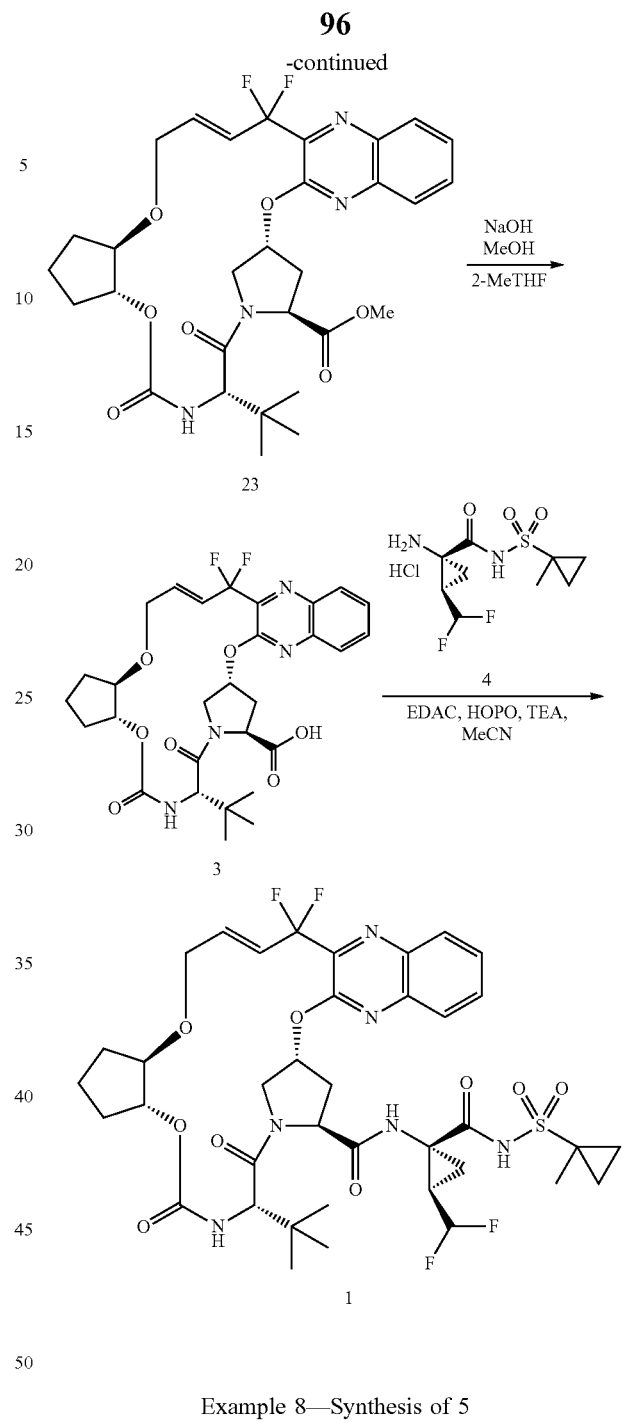
23
3
1
Example 8—Synthesis of 5
Scheme 10. Synthesis of 5
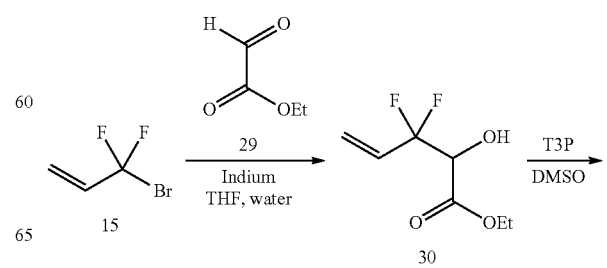
15  30

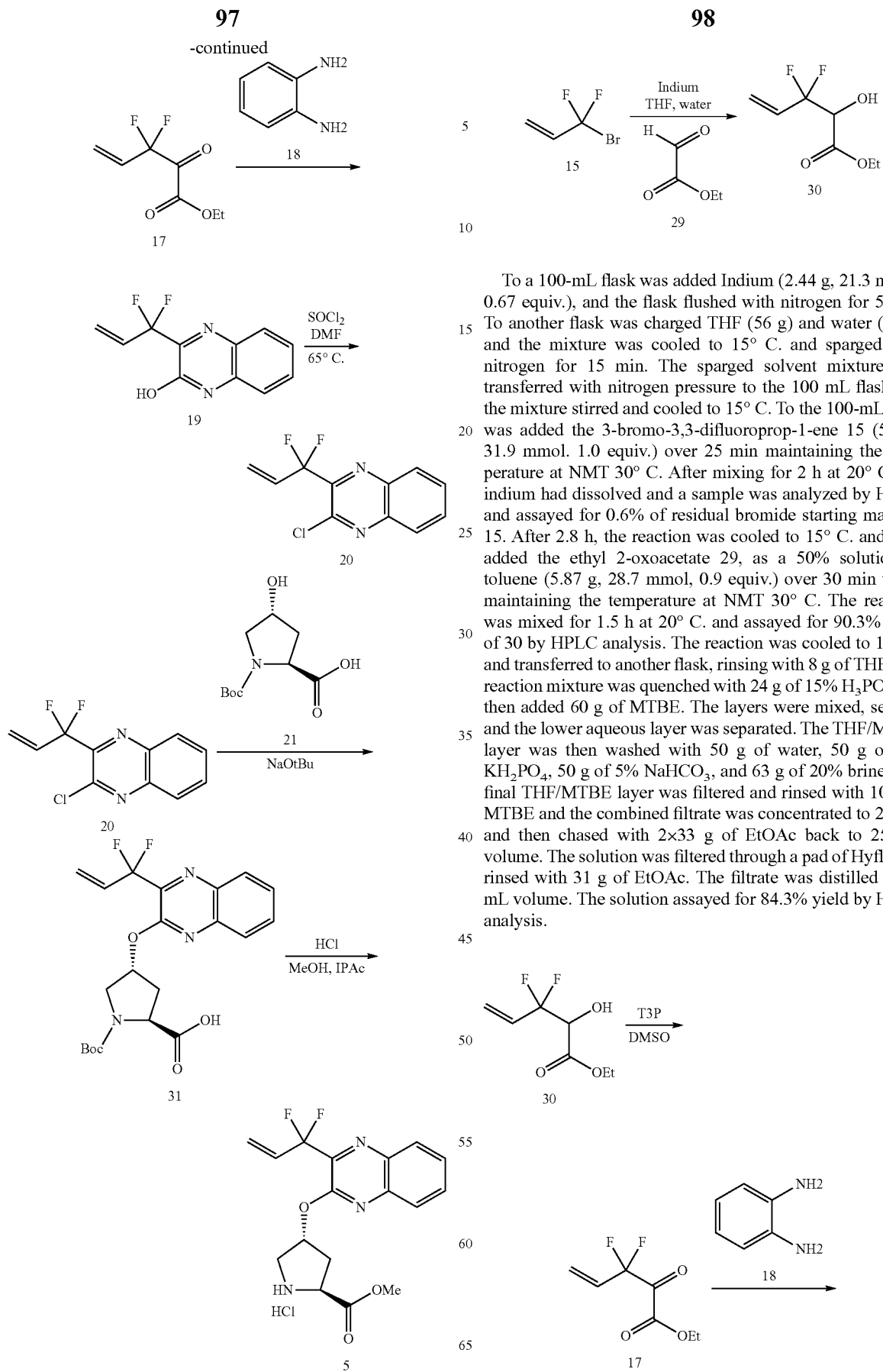

To a 100-mL flask was added Indium (2.44 g, 21.3 mmol, 0.67 equiv.), and the flask flushed with nitrogen for 5 min. To another flask was charged THF (56 g) and water (20 g) and the mixture was cooled to 15° C. and sparged with nitrogen for 15 min. The sparged solvent mixture was transferred with nitrogen pressure to the 100 mL flask and the mixture stirred and cooled to 15° C. To the 100-mL flask was added the 3-bromo-3,3-difluoroprop-1-ene 15 (5.0 g, 31.9 mmol. 1.0 equiv.) over 25 min maintaining the temperature at NMT 30° C. After mixing for 2 h at 20° C. the indium had dissolved and a sample was analyzed by HPLC and assayed for 0.6% of residual bromide starting material 15. After 2.8 h, the reaction was cooled to 15° C. and then added the ethyl 2-oxoacetate 29, as a 50% solution in toluene (5.87 g, 28.7 mmol, 0.9 equiv.) over 30 min while maintaining the temperature at NMT 30° C. The reaction was mixed for 1.5 h at 20° C. and assayed for 90.3% yield of 30 by HPLC analysis. The reaction was cooled to 15° C. and transferred to another flask, rinsing with 8 g of THF. The reaction mixture was quenched with 24 g of 15% $H_3PO_4$ and then added 60 g of MTBE. The layers were mixed, settled, and the lower aqueous layer was separated. The THF/MTBE layer was then washed with 50 g of water, 50 g of 5% $KH_2PO_4$, 50 g of 5% $NaHCO_3$, and 63 g of 20% brine. The final THF/MTBE layer was filtered and rinsed with 10 g of MTBE and the combined filtrate was concentrated to 25 mL and then chased with 2×33 g of EtOAc back to 25 mL volume. The solution was filtered through a pad of Hyflo and rinsed with 31 g of EtOAc. The filtrate was distilled to 10 mL volume. The solution assayed for 84.3% yield by HPLC analysis.

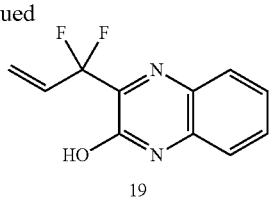

T3P (1.2 eq as a 50% solution in ethyl acetate) is added to a solution of alcohol 30 (1 eq., in dimethyl sulfoxide/ethyl acetate (DMSO/EA) (3 mL of each per g of 30) over 1.5 h while maintaining the reaction temperature at 0 to 5° C. Mixing is continued at 0° C. for 1 h, then the reaction mixture is allowed to warm to RT over 1 h. Mixing is further continued at RT (typically 12 to 17 h) until less than 5% peak area of 30 is detected by GC relative to product 17. The mixture is then cooled to 2° C. and triethylamine (TEA) (2.5 eq.) is added over 30 min while maintaining the temperature at less than 10° C. The pH of the reaction mixture is adjusted to 4.5 to 5.5 with acetic acid. The mixture is then cooled to ~2° C. and the phenylenediamine 18 solution (0.95 eq, in 1 mL/g ethyl acetate and 1 mL/g DMSO) is added over 20 min while maintaining LT 15° C. internal temperature. The mixing is continued for ~1 h until the reaction is complete (less than 5% ketone 17 by GC).

The mixture is then cooled to 5° C. and quenched by water addition (9 g/g of 30) over 1 h while maintaining the internal temperature at LT 25° C. The pH is then adjusted to 6 with 50% NaOH. The reaction mixture is then concentrated in vacuo to remove ethyl acetate and TEA (the residual volume target is approximately 15-17 mL/g of 30). Product precipitation is observed at this point. The mixture is then further diluted with water (9 g/g of 30) to precipitate remaining product. The product is then filtered off and the cake is washed with 4:1 water-ACN (2.5 g/g of 30). The product is dried at 45° C. to less than 0.5% water content by Karl Fischer (KF). Typical yield of 19 is 80-85%.

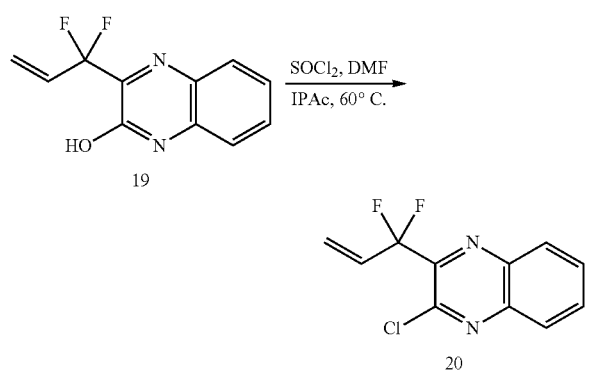

To a flask was charged 19, 20.35 g (95.9% potency, 92 mmol, 1.0 eq.), and then DMF, (1.355 g, 18.5 mmol, 0.2 eq), and then isopropyl acetate (89 g, of 19). The mixture was stirred at rt and then added thionyl chloride, (15.8 g, 133 mmol, 1.45 equiv.) was added over 5 minutes. The reaction mixture was then heated to 60° C. for 16 h and then cooled to 20° C. over the weekend. The reaction was cooled to 0° C. and then quenched with 120 g of water and the mixture was diluted with 125 g of heptanes and mixed at rt for 10 minutes. The reaction was then filtered, rinsing with 10 g of heptanes. The mixture was transferred to a separatory funnel and the lower aqueous layer separated. The IPAc/heptane layer was then washed with 120 g of water, 2 times with 120 g of 10% K$_2$HPO$_4$, and 150 g of 20% brine. The IPAc/heptane layer was then filtered through a pad of magnesium sulfate, and rinsed with 2×10 g of heptanes. The solution was concentrated to near completion and diluted with 155 g heptanes and concentrated to a volume of ~120 mL. The solution was diluted with 47 g heptanes and filtered through a pad of silica gel. The filtration was completed by rinsing with 20 g of heptanes, in portions, through the silica gel bed. A sample of the filtrate was analyzed by HPLC and assayed for 20.34 g, or 96.2% yield.

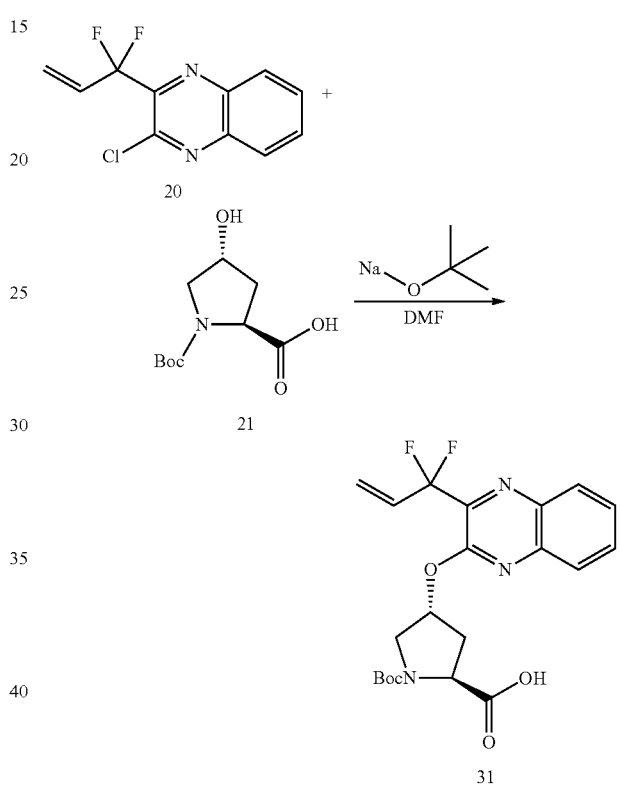

Into a 250-mL round bottom flask was added chloro quinoxaline 20 (5.07 g, 21.07 mmol) as a heptane solution, and DMF (10 mL). The solution was concentrated to ~15 mL to remove the heptane, and was then transferred into a nitrogen flushed, three necked flask containing 21 (5.26 g, 22.75 mmol, 1.08 equiv). The transfer was completed by rinsing the 250-mL flask with DMF (25.5 mL) and transferring the rinse into the three necked flask. The reaction mixture in the three neck flask was cooled to 0° C. Then a solution of NaOtBu (4.80 g, 48.5 mmol, 2.3 equiv) in DMF (30.4 mL) was added over 20 min while maintaining the temperature below 10° C. DMF (4 mL) was used to rinse the NaOtBu container and then added into the reaction mixture. The reaction was mixed at 0° C. for 2 h and then a sample was analyzed by HPLC and the starting material 20 was not detected. The reaction was quenched by slowly adding 50 g of water while maintaining the temperature at below 10° C. Then MTBE (67.5 mL) was added and the mixture was warmed to rt and stirred for 5 min. The mixture was transferred to a separatory funnel, rinsing with 25 g of water. The layers were mixed, settled and the lower aqueous layer containing the product was separated. The MTBE layer was extracted with water (25 mL) and the aqueous layers were combined. The aqueous solution was extracted with EtOAc (125 mL), and the pH adjusted to 2-3 by adding ~8.25 g of H₃PO₄ (71.6 mmol, 3.4 equiv.). The layers were mixed, settled, and separated. The EtOAc layer was washed with water (3×50 mL), saturated brine (50 mL), and dried over Na₂SO₄. The product solution assayed for 8.72 g of 31, for a 95.1% yield. The EtOAc solution was filtered, concentrated to near completion, and solvent switched to MeOH by chase distillation (3×38 mL). The final product was dissolved in 44 mL of MeOH and was used in the next reaction.

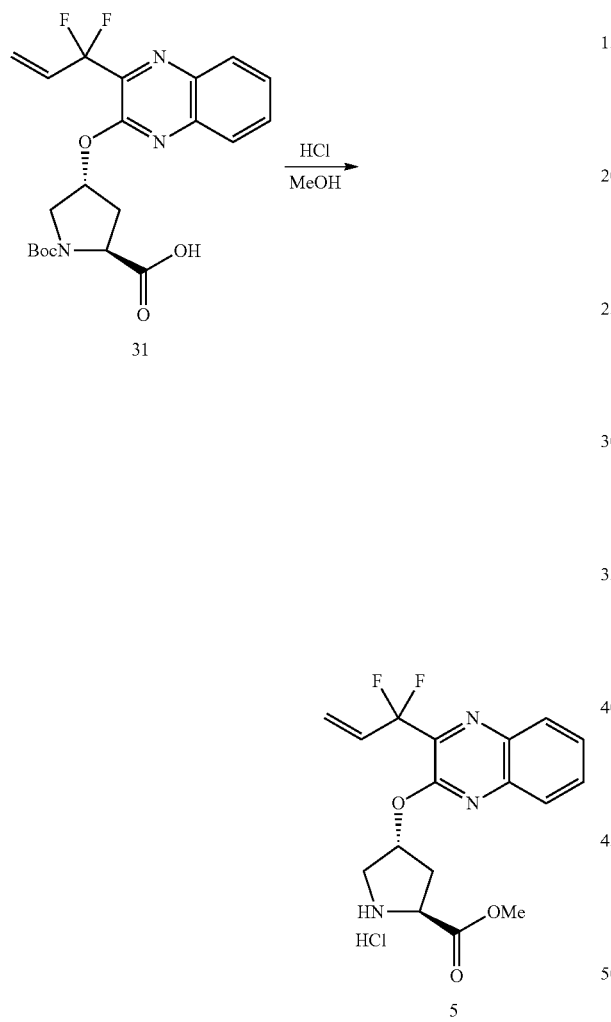

Into a 100-mL round bottom flask was added a solution of 31 in MeOH (10 g, 20.44% potency, 4.69 mmol). Then the HCl in MeOH solution (9.24 g, 13.9 wt %, 35.2 mmol, 7.5 equiv) was added slowly. The reaction solution was allowed to stir at r.t. over the weekend. The reaction was concentrated to ~5 mL and a constant volume distillation was performed charging NLT 30 mL of MeOH to maintain the volume at ~5 mL. To this mixture was slowly added 10 mL of IPAc to give a slurry. A constant volume distillation was performed maintaining the volume at ~15 mL while charging 40 mL of IPAc. The slurry was mixed at rt for 3 h and the product was filtered, washed with IPAc (3×2 mL), dried in oven at 40° C. for 16 h to give 1.51 g product 5 at 98% potency for an 82% yield.

Example 9—Synthesis of 3 Via RCM

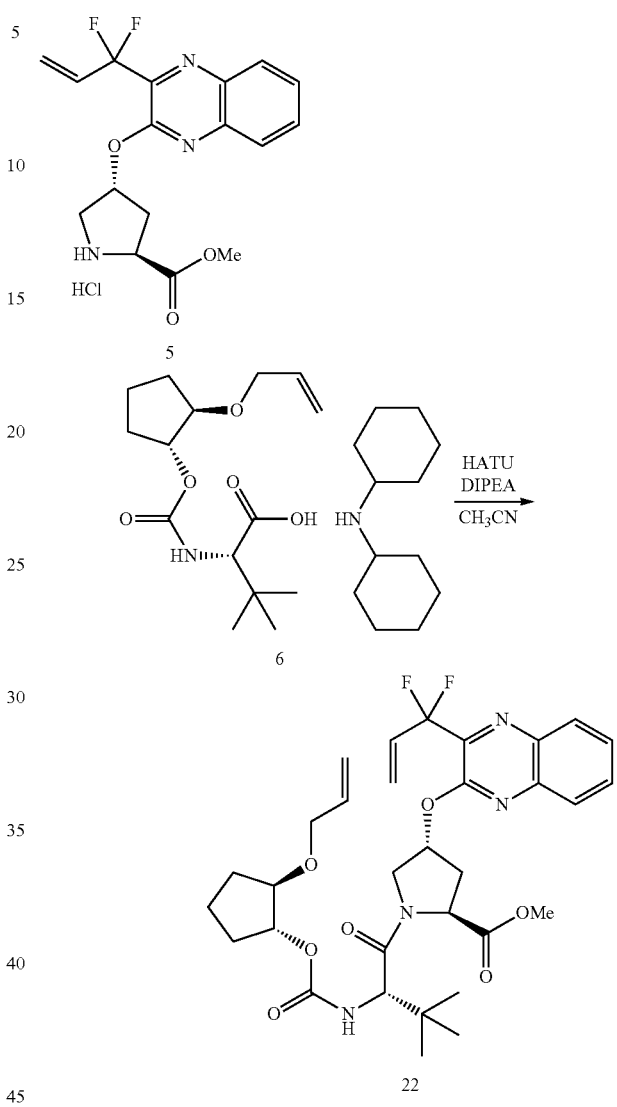

Dicyclohexylamine salt 6 (1.02 eq.) and HATU (1.1 eq.) are slurried in acetonitrile (6 g/g of 6) at ambient temperature. Formation of a clear solution is observed within 30 min. The solution is then transferred to a vessel containing 5 (1 eq) followed by an acetonitrile rinse (2 g/g of 6). The internal temperature is adjusted to ~15° C. and diisopropylethylamine (3.0 eq) is then added while maintaining the temperature below 25° C. The mixing is continued at 20 to 25° C. for typically 7 to 10 h. The mixture is then diluted with toluene (4.7 g/g of 6) and filtered to remove dicyclohexylamine hydrochloride. The cake is washed with toluene (2.5 g/g of 6) and the combined filtrate and wash are further diluted with water (6.25 g/g of 6). The pH of the mixture is adjusted to ~3.5 with conc. HCl while maintaining NMT 30° C. internal temperature. The aqueous layer is separated. The organic layer is washed subsequently with water and 5% potassium carbonate solution (6.25 g/g of 6 each). The organic layer is concentrated in vacuo to a volume of ~7.5 mL/g of 6 and purified by silica plug filtration eluting with EtOAc/heptanes. The product solution is solvent switched to toluene and the resulting solution typically assays for 100% yield of 22 and is used directly in the next step.

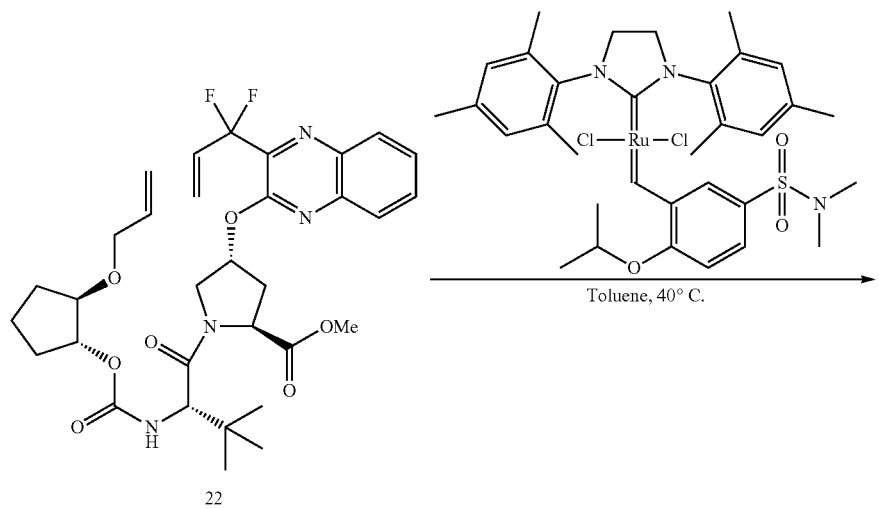

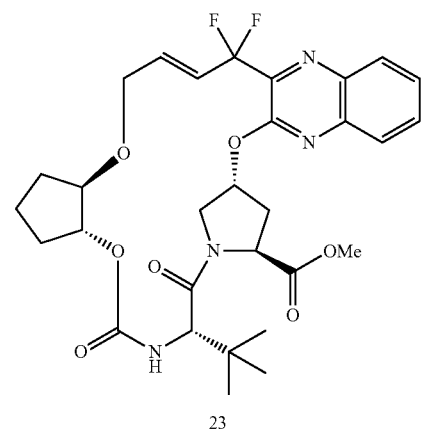

The Zhan 1B catalyst (340 mg, 0.463 mmol, 7 mole %) was dissolved in dichloromethane (DCM) (2 mL) and toluene (12 mL). To a 500 mL flask was charged 308 mL of toluene and the solvent sparged with nitrogen and heated to 40° C. To the heated toluene solution was added over 6 hours a solution of 22 (4 g, 6.34 mmol) in toluene (~10 mL) and the solution in of the catalyst at the same rate. After the addition was complete, the reaction was allowed to stir at 40° C. for 16 h. Another catalyst charge was prepared (47 mg, dissolved in 0.4 mL of DCM and 2 mL of toluene), and then added to the reaction mixture. After mixing for another 4 h, imidazole (0.426 g) and F1 Filtrol (4 g) were added to the reaction and the mixture was stirred at rt overnight. The reaction mixture was filtered through a silica gel plug (10 g), eluting with 50% ethyl acetate in heptanes. The crude product was further purified by silica gel chromatography and the product fractions were combined, concentrated, and assayed for 2.58 g of 23 for a 67.8% assay yield.

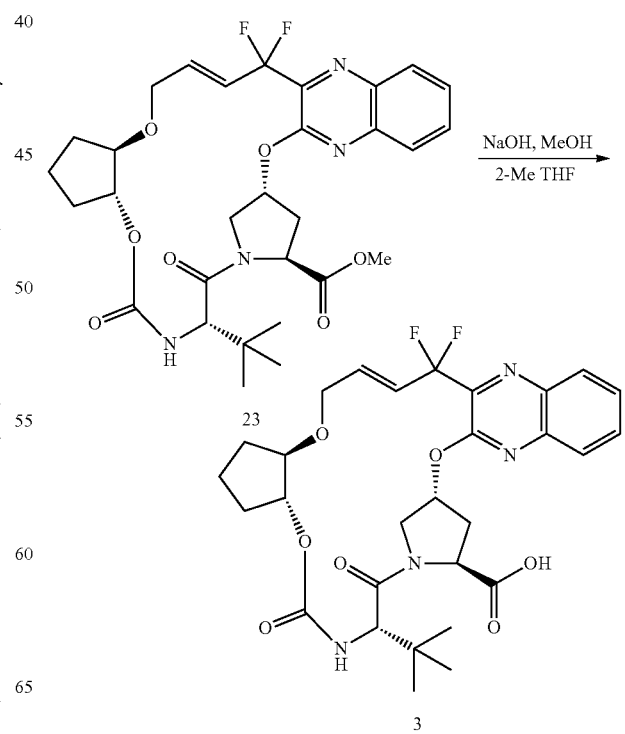

To a solution of 25.5 g of 23 (42.3 mmol) in 77 mL of MeOH was added 102 g of 2-MeTHF and the solution cooled below 15° C. To the solution was then added a solution of NaOH (2.5 g, 62.5 mmol, 1.5 equiv.) in 62.5 g of water and the reaction was mixed at 20° C. After 6 h the reaction was deemed complete by HPLC analysis. The mixture was cooled to below 15° C. and then 242 g of water was added, followed by 81 g of heptanes and 102 g of 2-MeTHF. The pH of the lower layer was adjusted to ~10 with $H_3PO_4$. The mixture was stirred for 10 min and then filtered, rinsing with 20 g of water. The filtrate was mixed, settled and the lower aqueous layer separated. The upper layer was washed with 20 g of water and this was combined with the first aqueous layer. The combined aqueous layers were diluted with 308 g of 2-MeTHF and acidified to pH 3 by charging $H_3PO_4$. The layers were mixed, settled and separated. The upper 2-MeTHF layer was then washed twice with 10% brine. The 2-MeTHF layer was then dried with magnesium sulfate and filtered, rinsing with 2-MeTHF. The filtrate was concentrated to approximately 90 mL, and diluted with 50 mL of 2-MeTHF. The solution was diluted with 48 g of heptanes and mixed until crystallization occurred and a slurry was formed, and then 271 g of heptanes was added. The slurry was filtered and rinsed with 50 mL of an 80/20 mixture v/v of heptanes/2-MeTHF. The crude product 3 was re-crystallized from 2-MeTHF/heptanes for an 83.9% yield.

Example 10—Alternative Synthesis of 69

The synthesis of compound 69 is shown in Scheme 11. In the first step, the alkene of compound 65 is dihydroxylated to yield the diol, compound 99. The diol 99 is then converted into the cyclic carbonate 100 by reaction with CDI or an equivalent reagent. The cyclic carbonate 100 is treated with base (NaHMDS) to induce elimination forming the open carbonate, compound 101, which then undergoes coupling with 21 to yield compound 68. Compound 68 can be isolated as a crystalline salt, and in this example the benzhydrylamine salt is shown. Compound 68 is then converted into compound 69 using thionyl chloride as the reagent, instead of HCl as shown in the previous example. Compound 69 is isolated as the HCl salt in this example, instead of the TsOH salt as shown in the previous example. The HCl salt of compound 69 may be used in the coupling reaction with compound 70 to form compound 71.

Scheme 11. Alternative Synthesis of 69

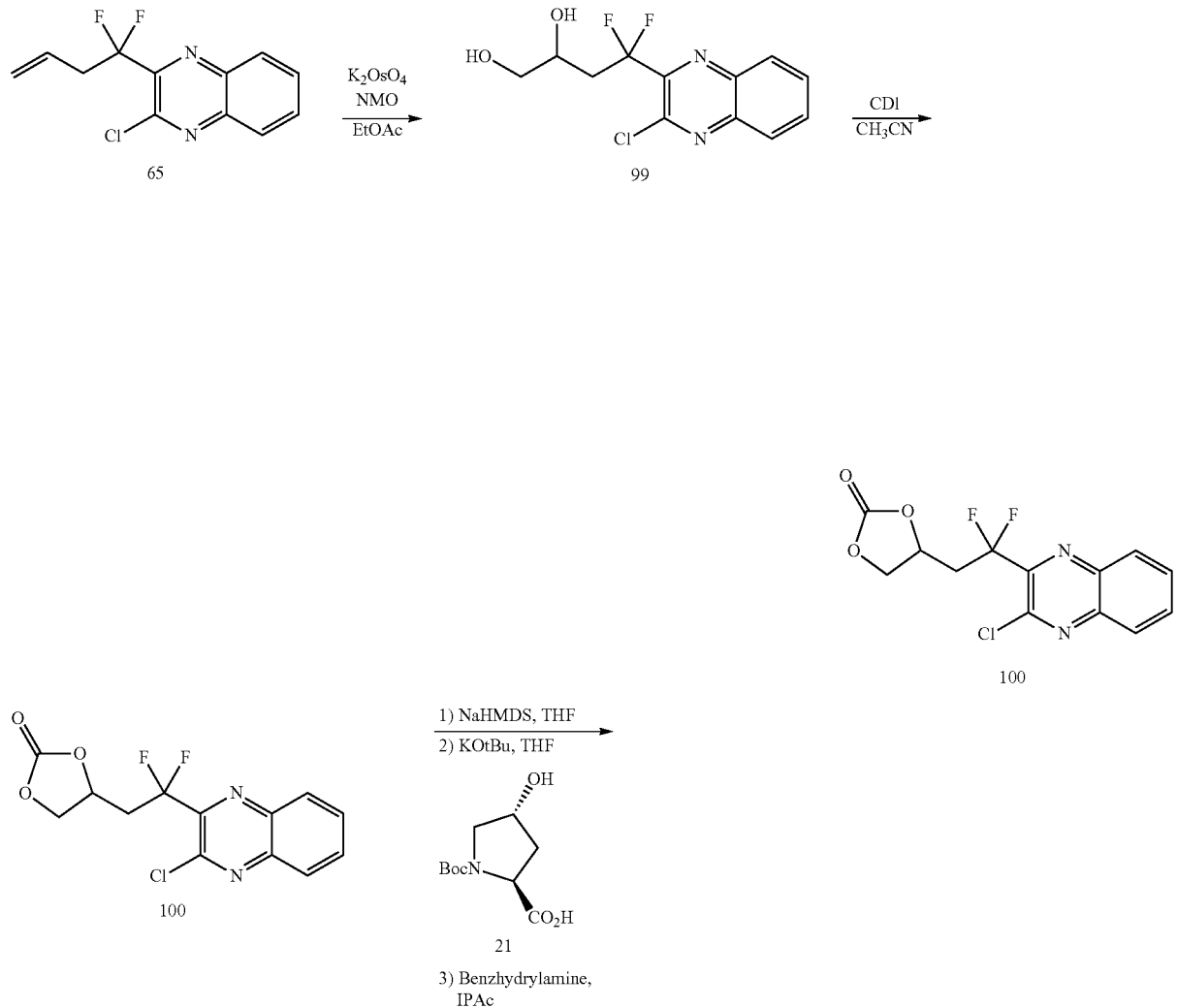

-continued

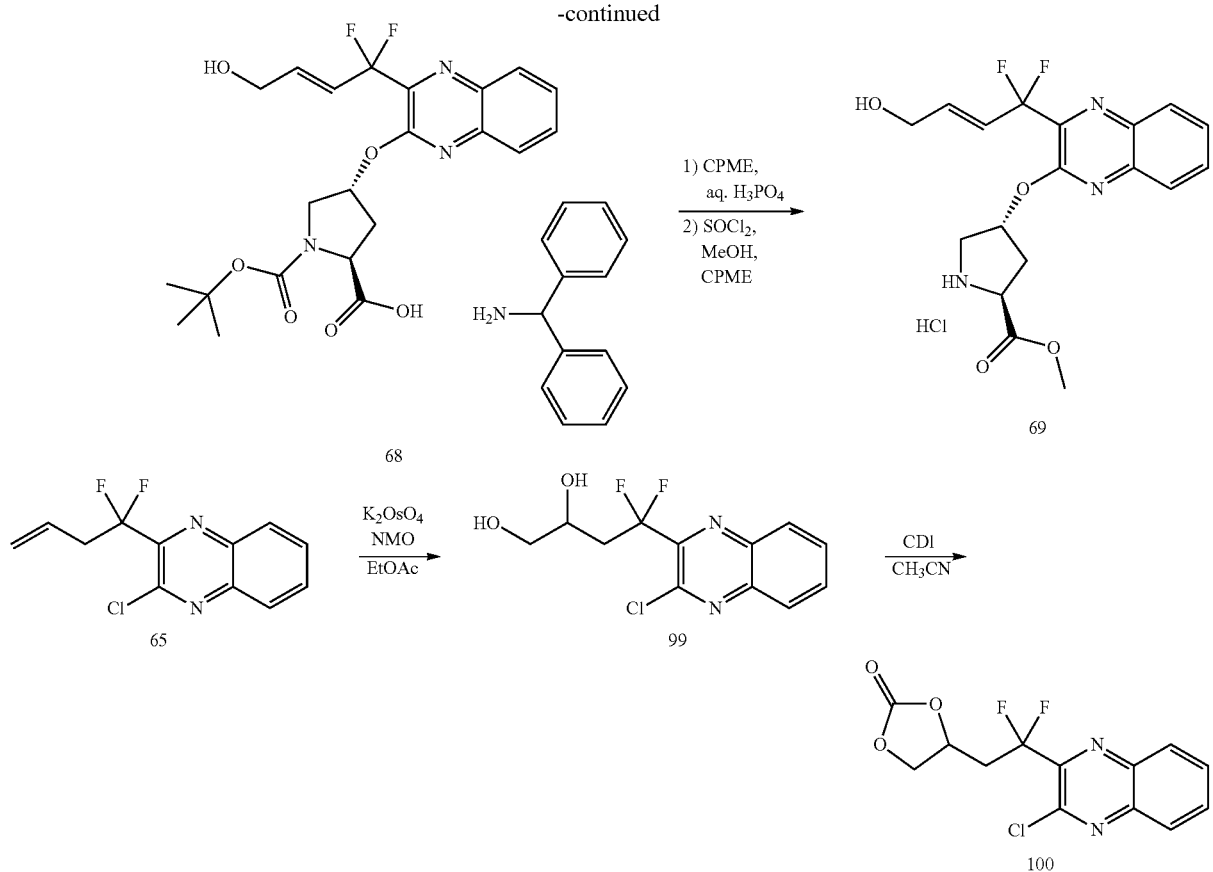

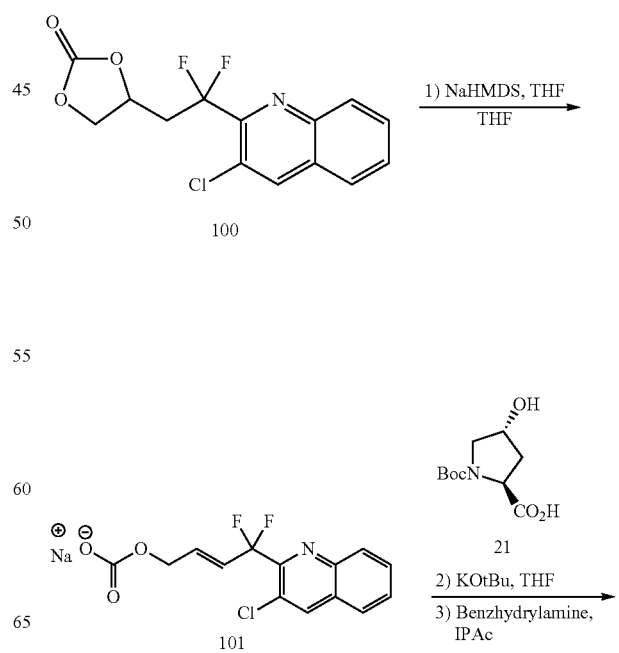

To a 1-L round bottom flask was added 2-chloro-3-(1,1-difluorobut-3-en-1-yl)quinoxaline, compound 65 (40.66 g, 157 mmol, 1.00 equiv.) followed by ethyl acetate (124 g), $K_2OsO_4 \cdot 2H_2O$ (0.088 g, 0.24 mmol, 0.0015 equiv.), and 50% aqueous N-methylmorpholine-N-oxide (42.32 g, 181 mmol, 1.15 equiv.). The biphasic mixture was stirred for 22.5 h at 40° C. After cooling to 23° C., an aqueous solution of 15% sodium sulfite (144 g) was added followed by ethyl acetate (124 g). After two hours the biphasic mixture was transferred to a separatory funnel, settled, and the aqueous layer separated. The organic layer was washed sequentially with a 10% aqueous solution of sodium chloride (145 g), a 13% aqueous solution of phosphoric acid (128 g), and a 10% aqueous solution of sodium chloride (144 g). The organic layer was transferred to a 1-L round bottom flask and concentrated to approximately 120 mL. Acetonitrile (80 g) was added and the solution distilled to approximately 120 mL. This chase distillation was repeated two more times. To this solution at 40° C. was added a solution of CDI (28.48 g, 173 mmol, 1.10 equiv.) over 1 h. The solution was cooled to 23° C. and concentrated to approximately 210 mL. To this solution at 40° C. was added water (537 g) over 1 h. The slurry was cooled to 23° C. and stirred for 5 h. The slurry was filtered and the wet cake washed twice with equal portions of a 20% solution of aqueous acetonitrile (80 g).

The wet cake was dried in a vacuum oven at 45° C. with a nitrogen sweep to give 4-(2-(3-chloroquinoxalin-2-yl)-2,2-difluoroethyl)-1,3-dioxolan-2-one, compound 100 (47.16 g, 95.5% yield).

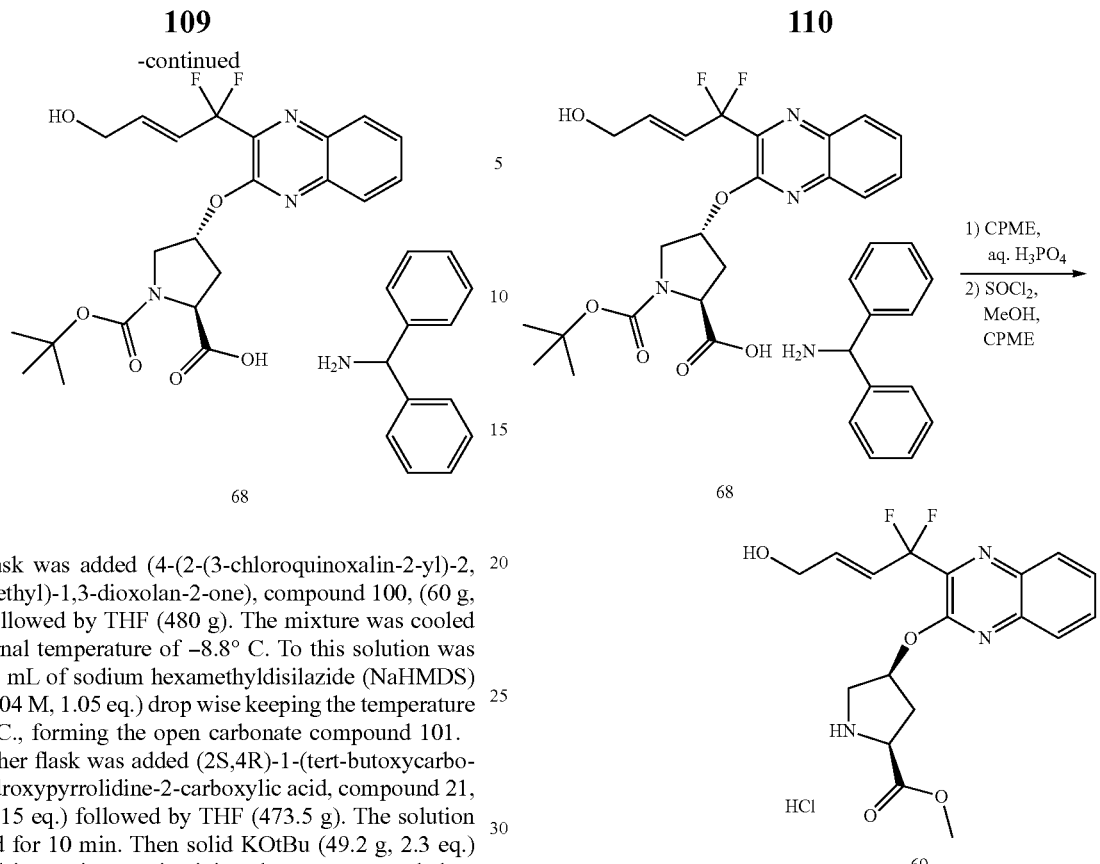

To a flask was added (4-(2-(3-chloroquinoxalin-2-yl)-2,2-difluoroethyl)-1,3-dioxolan-2-one), compound 100, (60 g, 1.0 eq.) followed by THF (480 g). The mixture was cooled to an internal temperature of −8.8° C. To this solution was added 193 mL of sodium hexamethyldisilazide (NaHMDS) in THF (1.04 M, 1.05 eq.) drop wise keeping the temperature below 0° C., forming the open carbonate compound 101.

To another flask was added (2S,4R)-1-(tert-butoxycarbonyl)-4-hydroxypyrrolidine-2-carboxylic acid, compound 21, (50.7 g, 1.15 eq.) followed by THF (473.5 g). The solution was mixed for 10 min. Then solid KOtBu (49.2 g, 2.3 eq.) was added in portions maintaining the temperature below 40° C. The resulting slurry was cooled below 30° C. and then water (1.72 g, 0.5 eq.) was added. The slurry was cooled to an internal temperature of 10° C. and then added to the flask containing compound 101. The flask containing the slurry of compound 21 was rinsed with 48 g of THF and the rinse was added to the flask containing compound 101. The mixture was stirred for 2 h at 0° C., and then quenched with 150 g of water.

The quenched reaction mixture was stirred for 30 min while warming to ambient temperature. The mixture was allowed to settle, and then the lower aqueous layer (along with solids) was removed. The solution was concentrated via rotovap to approximately 250 mL. The thick oil was diluted with 432 g of water. The aqueous product solution was extracted twice with isopropyl acetate (2×230 g). Then isopropyl acetate was added (270 g) to the aqueous product solution and, while mixing, 32 g of 85% phosphoric acid were added. After mixing, the bi-phasic solution was allowed to settle, the layers were separated, and the upper product layer was retained. The lower aqueous layer was extracted with an additional 270 g of isopropyl acetate to recover additional product. The isopropyl acetate layers were combined and then washed three times with 10% aqueous sodium phosphate monobasic (3×380 g), and then once with water (240 g). The product containing isopropyl acetate layer was heated to 45° C. and then treated with 4.5 g of activated carbon. The solution was concentrated and chased with isopropyl acetate to dry the solution. The product was crystallized from isopropyl acetate by the addition of 30.7 g (0.88 eq.) of benzhydrylamine, followed by cooling to 0° C. The slurry was filtered and washed with cold isopropyl acetate. The product was dried under vacuum at 45° C. overnight to yield 89.5 g of compound 68 as the benzhydrylamine salt (72%).

Compound 68 as the benzhydrylamine salt (23.4 g, 36 mmol) was combined with cyclopentyl methyl ether (CPME, 180 mL) and water (72 mL). Phosphoric acid (50 mL, 10%) was added and the contents were mixed for 10 min. The CPME layer was separated and washed with phosphoric acid (50 mL, 10%), then with water (50 mL) and concentrated in vacuo to ~40 g weight. The residue was diluted with methanol (67 mL), cooled to 0° C. and thionyl chloride (8.4 g, 72 mmol) was added slowly, maintaining the temperature below 15° C. Mixing was continued for 15 h at ambient temperature. Water (0.4 g) was added to the reaction mixture and mixing was continued for 1 h. The mixture was then diluted with CPME (72 mL) and concentrated in vacuo to ~85 mL volume while maintaining the internal temperature below 35° C. The mixture was re-diluted with CPME (72 mL) and concentrated in vacuo to ~85 mL volume while maintaining the internal temperature below 35° C. The product slurry was agitated at ambient temperature and filtered. The filter cake was washed with CPME and dried in vacuo at less than 40° C. to give 14.2 g of compound 69 as the HCl salt (95% yield).

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents, and published patent applications, and patent applications cited throughout this application are incorporated herein by reference.

We claim:

1. A method comprising one or more of steps A, C, D, E, E', F, F', G, G', H, I, J, K, L, M, and N:

(A)

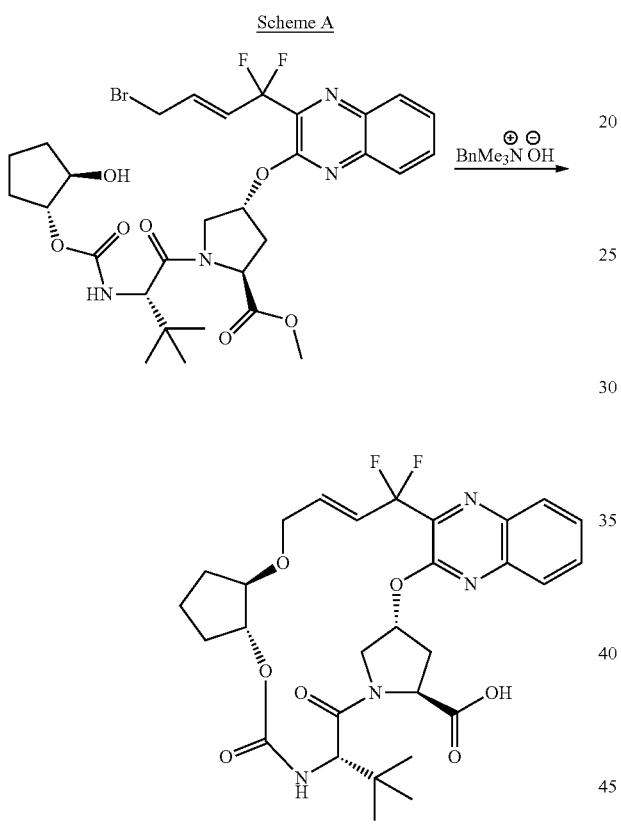

wherein the reaction takes place in a sixteenth solvent, thereby forming a thirteenth product mixture comprising (C)

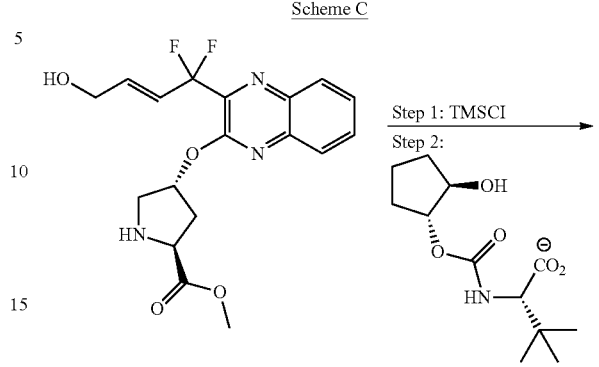

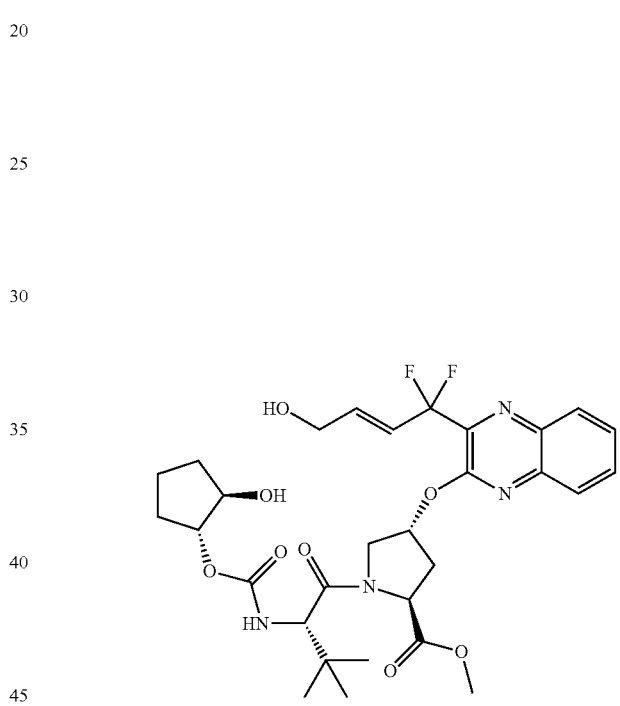

wherein Step 1 of the reaction takes place in a thirteenth solvent in the presence of a seventh base; and Step 2 of the reaction takes place in a fourteenth solvent, thereby forming an eleventh product mixture comprising

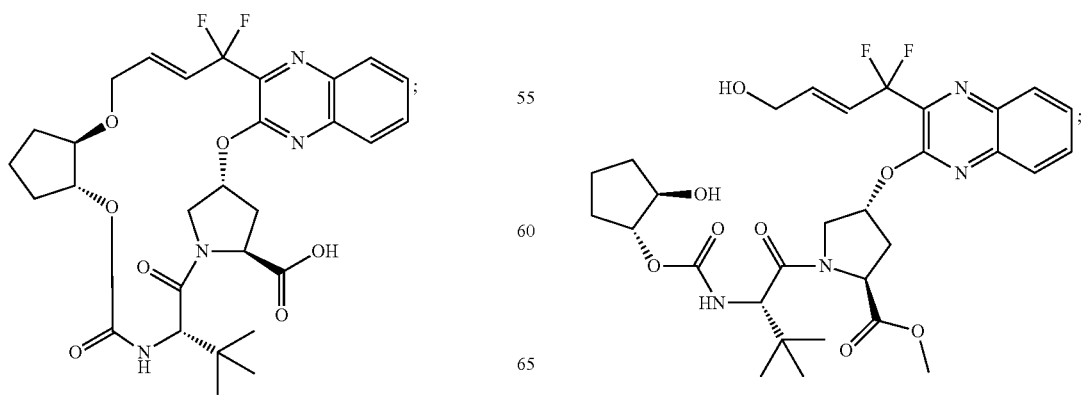

(D)

Scheme D

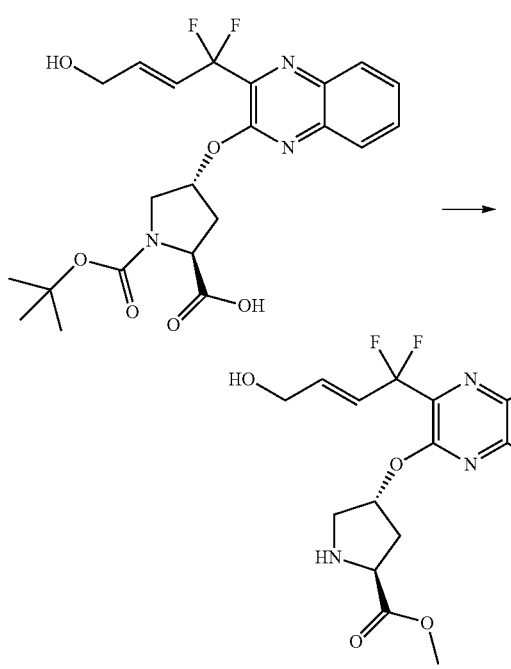

wherein the reaction takes place in a twelfth solvent in the presence of a second acid, thereby forming a tenth product mixture comprising

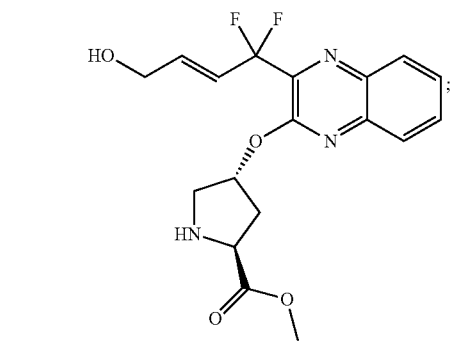 [SMILES: COC(=O)[C@@H]1C[C@@H](Oc2nc3ccccc3nc2C(F)(F)/C=C/CO)CN1]

(E)

Scheme E

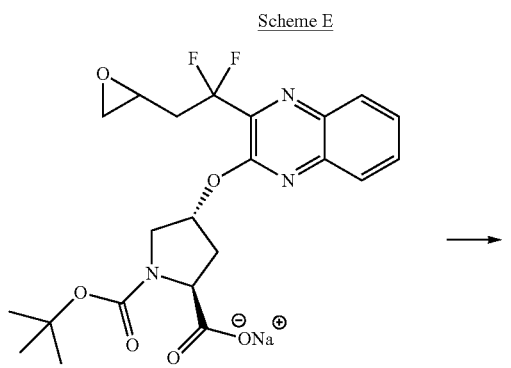

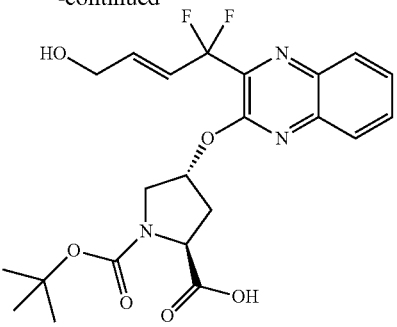

wherein the reaction takes place in an eleventh solvent in the presence of a sixth base, thereby forming a ninth product mixture comprising

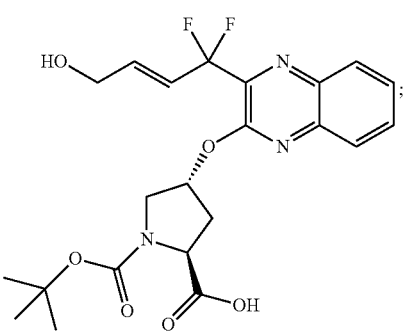 [SMILES: CC(C)(C)OC(=O)N1C[C@H](Oc2nc3ccccc3nc2C(F)(F)/C=C/CO)C[C@H]1C(=O)O]

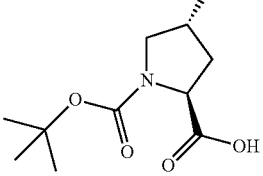

(E')

Scheme E'

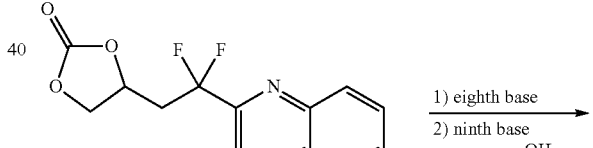

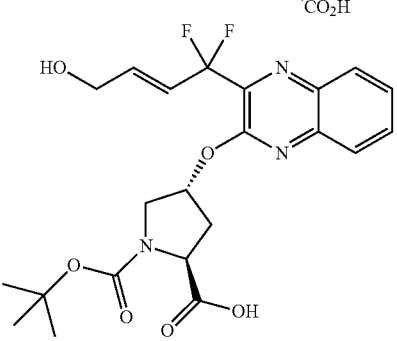

wherein step (1) takes place in a nineteenth solvent in the presence of an eighth base, and step (2) takes place in a twentieth solvent in the presence of a ninth base, thereby forming a sixteenth product mixture comprising

115

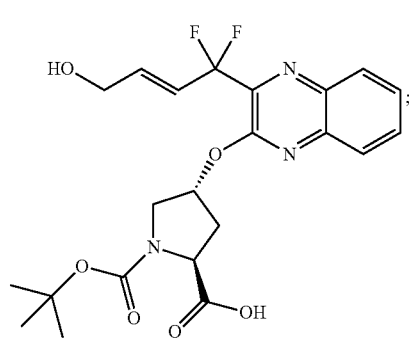 [SMILES: CC(C)(C)OC(=O)N1C[C@H](Oc2nc3ccccc3nc2C(F)(F)/C=C/CO)C[C@H]1C(=O)O]

(F)

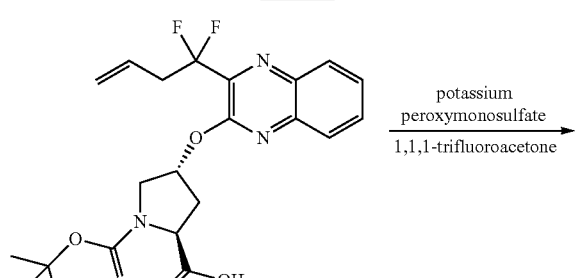

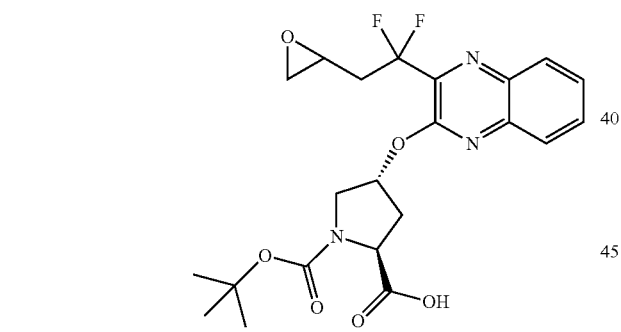

wherein the reaction takes place in a tenth solvent in the presence of a fifth base, thereby forming an eighth product mixture comprising

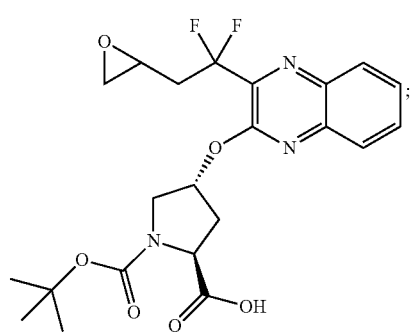 [SMILES: CC(C)(C)OC(=O)N1C[C@H](Oc2nc3ccccc3nc2C(F)(F)CC2CO2)C[C@H]1C(=O)O]

116

(F')

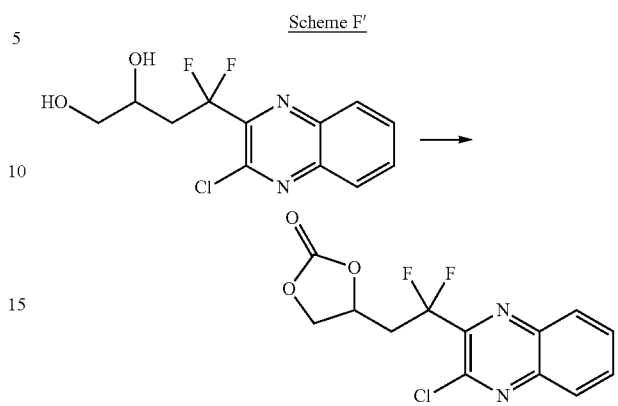

wherein the reaction takes place in a eighteenth solvent in the presence of a reagent, thereby forming an fifteenth product mixture comprising

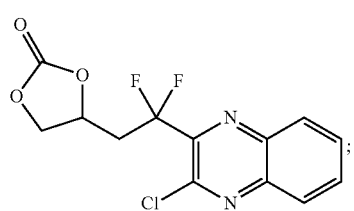 [SMILES: O=C1OCC(CC(F)(F)c2nc3ccccc3nc2Cl)O1]

(G)

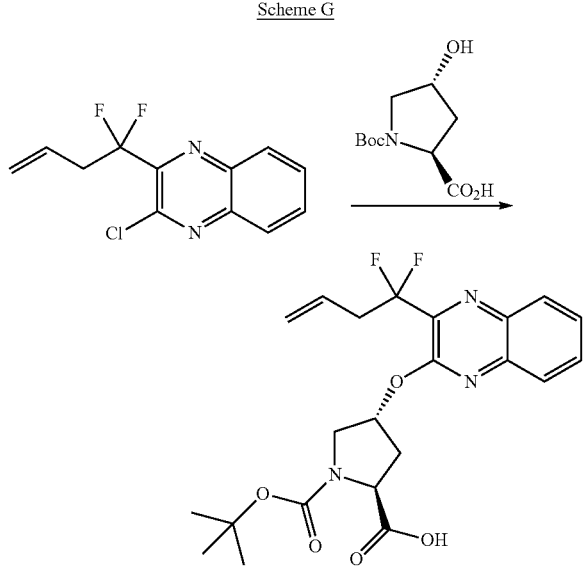

wherein the reaction takes place in a ninth solvent in the presence of a fourth base, thereby forming a seventh product mixture comprising

117

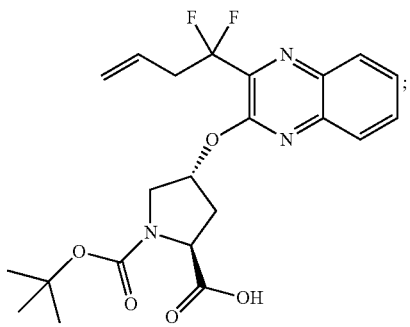 [SMILES: C=CCC(F)(F)c1nc2ccccc2nc1O[C@@H]1C[C@@H](C(=O)O)N(C(=O)OC(C)(C)C)C1]

(G')

Scheme G'

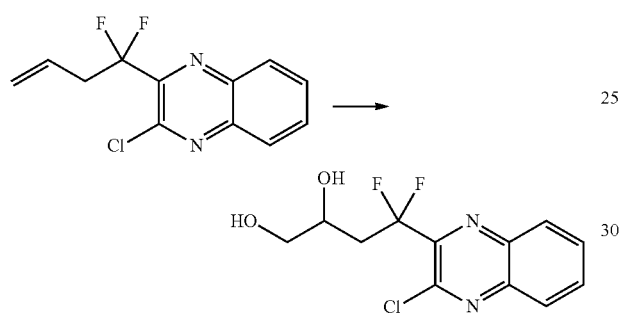

wherein the reaction takes place in a seventeenth solvent in the presence of an oxidant, thereby forming a fourteenth product mixture comprising

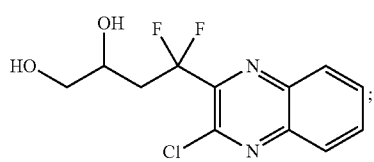 [SMILES: OCC(O)CC(F)(F)c1nc2ccccc2nc1Cl]

(H)

Scheme H

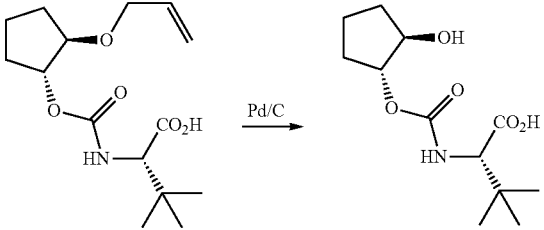

wherein the reaction takes place in an eighth solvent, thereby forming a sixth product mixture comprising

118

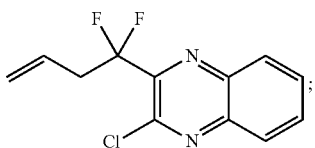 [SMILES: C=CCC(F)(F)c1nc2ccccc2nc1Cl]

(I)

Scheme I

Step 1: Sixth Temp.
Step 2:

wherein Step 1 of the reaction takes place in a sixth solvent at a sixth temperature to effect a Claisen rearrangement, and Step 2 of the reaction takes place in a seventh solvent at a seventh temperature, thereby forming a fifth product mixture comprising

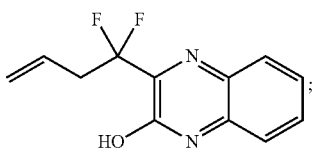 [SMILES: C=CCC(F)(F)c1nc2ccccc2nc1O]

(J)

Scheme J wherein the reaction takes place in a fifth solvent in the presence of a first acid and a hydrogen source, thereby forming a fourth product mixture comprising

119

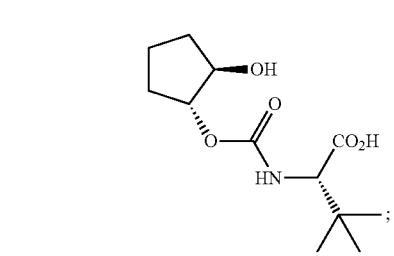 [SMILES: CC(C)(C)[C@H](NC(=O)O[C@@H]1CCC[C@H]1O)C(=O)O]

(K)

Scheme K

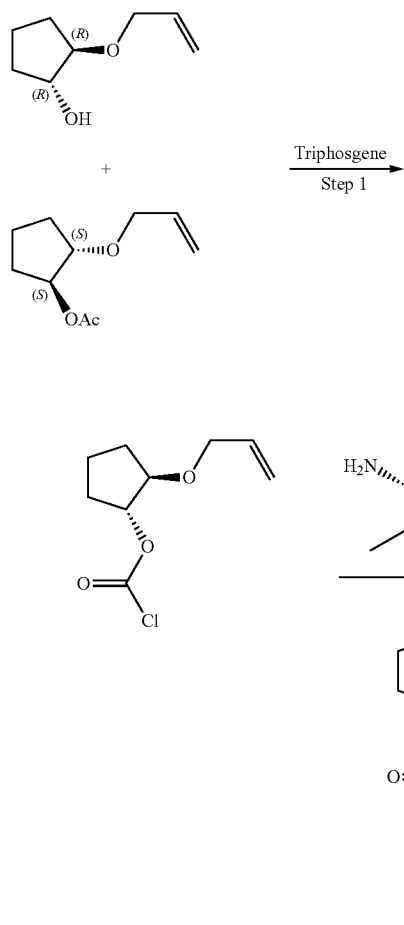

wherein Step 1 of the reaction takes place in a third solvent in the presence of a second base; and Step 2 of the reaction takes place in a fourth solvent in the presence of a third base, thereby forming a third product mixture comprising

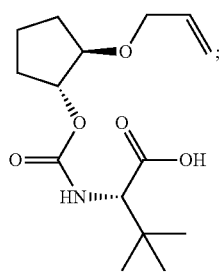 [SMILES: C=CCO[C@@H]1CCC[C@H]1OC(=O)N[C@H](C(=O)O)C(C)(C)C]

120

(L)

Scheme L

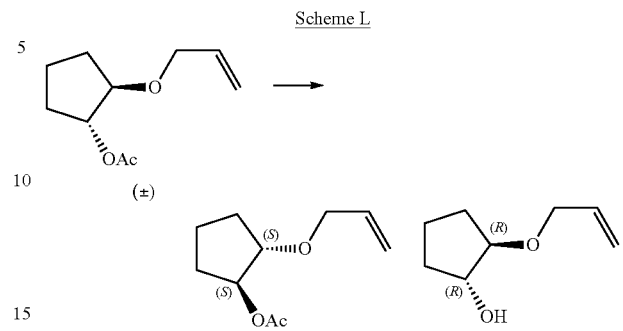

wherein the reaction takes place in a second solvent in the presence of a first enzyme, thereby forming a second product mixture comprising

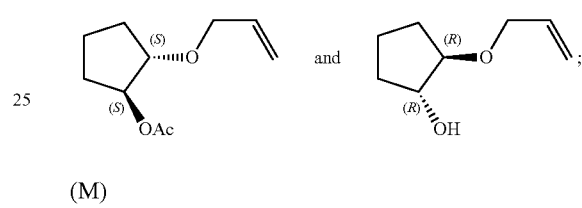

(M)

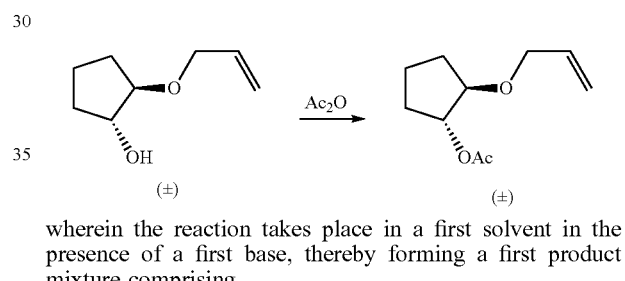

wherein the reaction takes place in a first solvent in the presence of a first base, thereby forming a first product mixture comprising

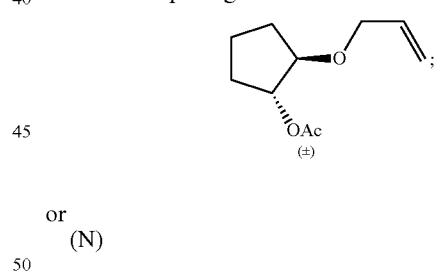

or
(N)

Scheme N

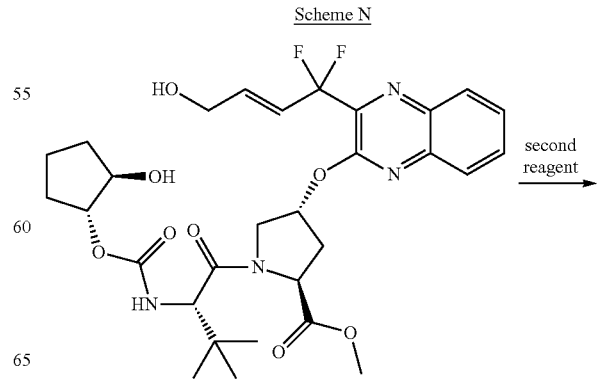

wherein:
LG is a leaving group; and
the second reagent comprises one or more reagents sufficient to replace the OH with group LG.

2. The method of claim 1, comprising the reaction of Scheme N, wherein LG is Br, and the second reagent comprises PPh$_3$ and Br$_2$.

* * * * *